US009059414B2

(12) United States Patent
Inoue et al.

(10) Patent No.: US 9,059,414 B2
(45) Date of Patent: Jun. 16, 2015

(54) PHOSPHORESCENT ORGANOMETALLIC IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoka Nakagawa, Kanagawa (JP); Tomoya Yamaguchi, Kanagawa (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/539,377

(22) Filed: Nov. 12, 2014

(65) Prior Publication Data

US 2015/0073144 A1  Mar. 12, 2015

Related U.S. Application Data

(62) Division of application No. 13/860,858, filed on Apr. 11, 2013, now Pat. No. 8,889,858.

(30) Foreign Application Priority Data

Apr. 20, 2012 (JP) ................................. 2012-096275
Mar. 12, 2013 (JP) ................................. 2013-049025

(51) Int. Cl.
*C07D 239/00* (2006.01)
*C07D 213/04* (2006.01)
*H01L 51/00* (2006.01)
*H01L 51/50* (2006.01)

(52) U.S. Cl.
CPC ........ *H01L 51/0085* (2013.01); *H01L 51/0067* (2013.01); *H01L 51/5016* (2013.01)

(58) Field of Classification Search
USPC .......................................... 544/242; 546/255
See application file for complete search history.

(56) References Cited

U.S. PATENT DOCUMENTS

| | | | |
|---|---|---|---|
| 6,097,147 A | 8/2000 | Baldo et al. |
| 6,830,828 B2 | 12/2004 | Thompson et al. |
| 6,902,830 B2 | 6/2005 | Thompson et al. |
| 7,001,536 B2 | 2/2006 | Thompson et al. |
| 7,291,406 B2 | 11/2007 | Thompson et al. |
| 7,537,844 B2 | 5/2009 | Thompson et al. |
| 7,807,839 B2 | 10/2010 | Inoue et al. |
| 7,883,787 B2 | 2/2011 | Thompson et al. |
| 7,993,494 B2 | 8/2011 | Inoue et al. |
| 8,084,145 B2 | 12/2011 | Inoue et al. |
| 2005/0221123 A1 | 10/2005 | Inoue et al. |
| 2007/0129545 A1 | 6/2007 | Inoue et al. |
| 2007/0244320 A1 | 10/2007 | Inoue et al. |
| 2008/0149923 A1 | 6/2008 | Ohsawa et al. |
| 2008/0233432 A1 | 9/2008 | Inoue et al. |
| 2008/0286604 A1 | 11/2008 | Inoue et al. |
| 2008/0305361 A1 | 12/2008 | Inoue et al. |
| 2008/0312437 A1 | 12/2008 | Inoue et al. |
| 2009/0015143 A1 | 1/2009 | Inoue et al. |
| 2009/0039776 A1 | 2/2009 | Yamada et al. |

(Continued)

FOREIGN PATENT DOCUMENTS

| | | |
|---|---|---|
| JP | 2007-137872 A | 6/2007 |
| JP | 2008-069221 A | 3/2008 |
| JP | 2012-004526 A | 1/2012 |
| TW | I231157 | 4/2005 |
| WO | WO 00/70655 A2 | 11/2000 |
| WO | WO 2008/035664 A1 | 3/2008 |
| WO | WO 2009/011447 A2 | 1/2009 |

OTHER PUBLICATIONS

Niu, Y.-H. et al., "Highly Efficient Red Electrophosphorescent Devices Based on an Iridium Complex with Trifluoromethyl-Substituted Pyrimidine Ligand," Applied Physics Letters, Aug. 30, 2004, vol. 85, No. 9, pp. 1619-1621.

(Continued)

*Primary Examiner* — James O Wilson
*Assistant Examiner* — Oluwafemi Masha
(74) *Attorney, Agent, or Firm* — Husch Blackwell LLP

(57) ABSTRACT

As a novel substance having a novel skeleton, provided is a novel phosphorescent organometallic iridium complex that can emit phosphorescence in a blue green to red wavelength region and has high emission efficiency. The phosphorescent organometallic iridium complex has a ligand having a pyridyl pyrimidine skeleton, i.e., the phosphorescent organometallic iridium complex has a ligand having a structure represented by the following general formula (G0).

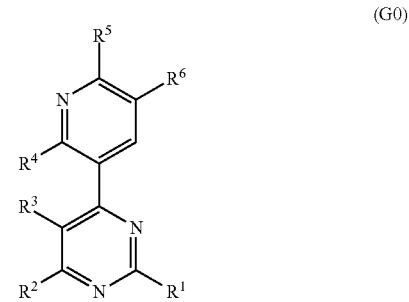

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

16 Claims, 24 Drawing Sheets

(56) References Cited

U.S. PATENT DOCUMENTS

| | | |
|---|---|---|
| 2010/0105902 A1 | 4/2010 | Inoue et al. |
| 2010/0145044 A1 | 6/2010 | Inoue et al. |
| 2010/0181905 A1 | 7/2010 | Inoue et al. |
| 2010/0219407 A1 | 9/2010 | Kamatani et al. |
| 2011/0082296 A1 | 4/2011 | Inoue et al. |
| 2011/0112296 A1 | 5/2011 | Thompson et al. |
| 2011/0187265 A1 | 8/2011 | De Cola et al. |
| 2011/0245495 A1 | 10/2011 | Inoue et al. |
| 2012/0098417 A1 | 4/2012 | Inoue et al. |
| 2012/0264936 A1 | 10/2012 | Inoue et al. |
| 2013/0048964 A1 | 2/2013 | Takeda et al. |

OTHER PUBLICATIONS

Caygill, G.B. et al., "Cyclometallated Compounds IV. Cyclopalladation of Phenylpyrimidines and X-ray Structure of a Doubly Cytopalladated Derivative of 4,6-diphenylpyrimidine," Journal of Organometallic Chemistry, Feb. 13, 1990, vol. 382, No. 3, pp. 455-469.

Kawanishi, Y. et al., "Dependence of Spectroscopic, Electrochemical, and Excited-State Properties of tris Chelate Ruthenium(II) Complexes on Ligand Structure," Inorganic Chemistry, 1989, vol. 28, No. 15, pp. 2968-2975.

Kozhevnikov, V.N. et al., "Highly Luminescent Mixed-Metal Pt(II)/Ir(III) Complexes: Bis-Cyclometalation of 4,6-Dihenylpyrimidine As a Versitile Route to Rigid Multimetallic Assemblies," Inorganic Chemistry, 2011, vol. 50, No. 13, pp. 6304-6313.

Bredereck, H. et al., "Formamide Reactions, VIII. A New Pyrimidine-Synthesis," Chemische Berichte, 1957, vol. 90, pp. 942-952.

Mydlak, H. et al., "Positively Charged Iridium(III) Triazole Derivatives as Blue Emitters for Light-Emitting Electrochemical Cells," Advanced Functional Materials, 2010, vol. 20, No.11, pp. 1812-1820.

PHOSPHORESCENT ORGANOMETALLIC IRIDIUM COMPLEX, LIGHT-EMITTING ELEMENT, LIGHT-EMITTING DEVICE, ELECTRONIC DEVICE, AND LIGHTING DEVICE

This application is a divisional of copending application Ser. No. 13/860,858 filed on Apr. 11, 2013, which is incorporated herein by reference.

BACKGROUND OF THE INVENTION

1. Field of the Invention

One embodiment of the present invention relates to a phosphorescent organometallic iridium complex that is capable of converting a triplet excited state into luminescence. In addition, one embodiment of the present invention relates to a light-emitting element, a light-emitting device, an electronic device, and a lighting device each including the phosphorescent organometallic iridium complex.

2. Description of the Related Art

A light-emitting element having a structure in which a light-emitting layer containing an organic compound that is a light-emitting substance is provided between a pair of electrodes has attracted attention as a next-generation flat panel display element in teams of characteristics such as being thin and light in weight, high speed response, and direct current low voltage driving. Further, a display including this light-emitting element is superior in contrast, image quality, and wide viewing angle.

Some of organic compounds which can be used for a light-emitting layer are capable of emitting phosphorescence from an excited state. Phosphorescence refers to luminescence generated by transition between energies of different multiplicity. In an ordinary organic compound, phosphorescence refers to luminescence that is generated at the time of relax from a triplet excited state to a singlet ground state (in contrast, fluorescence refers to luminescence that is generated at the time of relax from a singlet excited state to a singlet ground state). When such a compound capable of emitting phosphorescence, i.e., converting a triplet excited state into luminescence (hereinafter referred to as phosphorescent compound), is used as a light-emitting substance in a light-emitting layer, internal quantum efficiency can be increased; thus, a highly efficient light-emitting element can be obtained.

A phosphorescent organometallic iridium complex that contains iridium or the like as a central metal is particularly attracting attention as a phosphorescent compound because of its high phosphorescence quantum yield (refer to Patent Document 1, Patent Document 2, and Patent Document 3, for example).

REFERENCE

Patent Document

[Patent Document 1] Japanese Published Patent Application No. 2007-137872
[Patent Document 2] Japanese Published Patent Application No. 2008-069221
[Patent Document 3] International Publication WO 2008/035664 Pamphlet

SUMMARY OF THE INVENTION

While blue or green phosphorescent materials have been developed as reported in Patent Documents 1 to 3, what is also important in view of extension of the range of light-emitting materials is development of materials having novel skeletons.

Thus, as a novel substance having a novel skeleton, one embodiment of the present invention provides a novel phosphorescent organometallic iridium complex that can emit phosphorescence in a blue green to red wavelength region and has high emission efficiency. Further, an object of one embodiment of the present invention is to provide a light-emitting element, a light-emitting device, an electronic device, or a lighting device each having high emission efficiency.

One embodiment of the present invention is a phosphorescent organometallic iridium complex with a ligand having a pyridyl pyrimidine skeleton. A phosphorescent organometallic iridium complex with a ligand having a pyrimidine skeleton having a pyridyl group at the 4-position is preferable, and a phosphorescent organometallic iridium complex with a ligand having a 4-(3-pyridyl)pyrimidine skeleton or a 4-(4-pyridyl)pyrimidine skeleton is more preferable. Further, a structure of one embodiment of the present invention is a phosphorescent organometallic iridium complex with a ligand having a structure represented by the following general formula (G0).

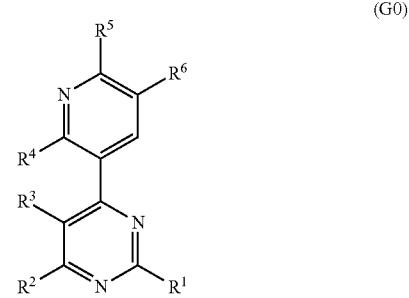

(G0)

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Another embodiment of the present invention is a phosphorescent organometallic iridium complex having a structure represented by the following general formula (G0').

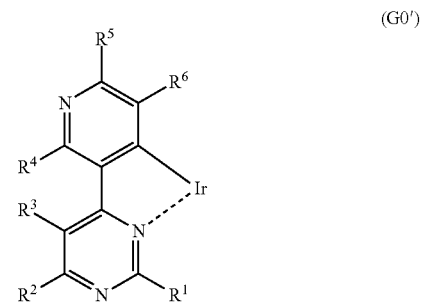

(G0')

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

In particular, a phosphorescent organometallic iridium complex having the structure which is represented by the general formula (G0') and in which the lowest triplet excited state is formed is preferable because phosphorescence can be efficiently emitted. To achieve such a mode, another skeleton (another ligand) which is included in the phosphorescent organometallic iridium complex may be selected such that the lowest triplet excitation energy of the structure is equal to or lower than the lowest triplet excitation energy of the another skeleton (the another ligand), for example. With such a structure, regardless of what a skeleton (ligand) other than the structure is, the lowest triplet excited state is formed by the structure at last, so that phosphorescence originating from the structure is obtained. Therefore, phosphorescence can be highly efficiently obtained. A typical example is vinyl polymer having the structure as a side chain.

Further, another embodiment of the present invention is a phosphorescent organometallic iridium complex having a structure represented by the following general formula (G1).

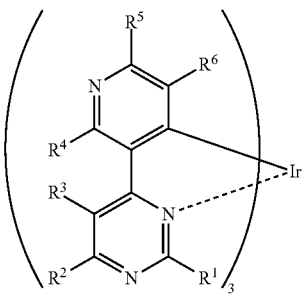

(G1)

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Further, another embodiment of the present invention is a phosphorescent organometallic iridium complex having a structure represented by the following general formula (G2).

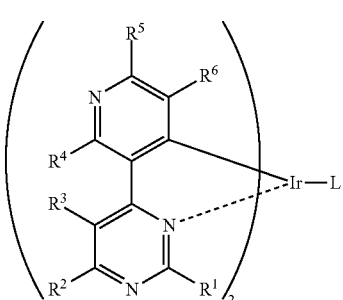

(G2)

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent. Further, L represents a monoanionic ligand.

Further, another embodiment of the present invention is a phosphorescent organometallic iridium complex having a structure represented by the following general formula (G3).

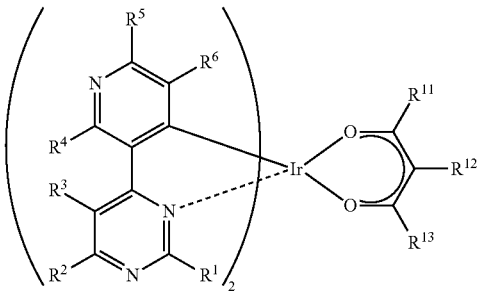

(G3)

Note that in the formula, $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent. Further, $R^{11}$ to $R^{13}$ separately represent hydrogen or an alkyl group having 1 to 6 carbon atoms.

Further, another embodiment of the present invention is a phosphorescent organometallic iridium complex represented by the following structural formula (100).

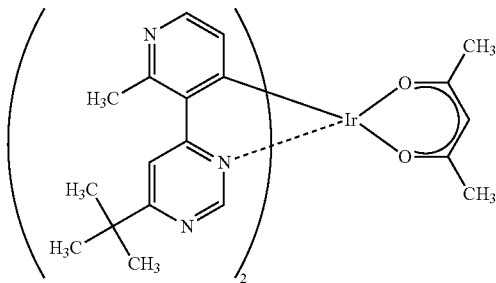

(100)

Further, another embodiment of the present invention is a phosphorescent organometallic iridium complex represented by the following structural formula (101).

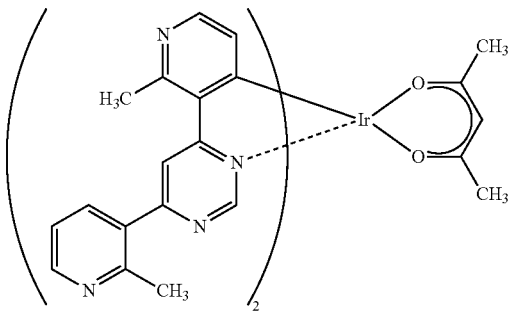

(101)

Further, another embodiment of the present invention is a phosphorescent organometallic iridium complex represented by the following structural formula (102).

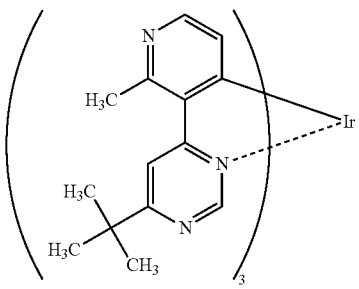

(102)

In the above-described phosphorescent organometallic iridium complexes according to embodiments of the present invention, a structure with a ligand having a pyridyl pyrimidine skeleton increases both molar absorption coefficient and quantum yield which determine the intensity of phosphorescence. Further, the structure with a ligand having a pyridyl pyrimidine skeleton increases the LUMO level in the negative direction. That is, electrons can be injected efficiently; accordingly, by using the phosphorescent organometallic iridium complex together with a material by which holes can be injected efficiently in a similar manner, the recombination probability of electrons and holes increases, and a light-emitting element with high emission efficiency can be obtained.

Further, by using the phosphorescent organometallic iridium complex according to one embodiment of the present invention for a light-emitting element, a highly efficient element can be fabricated. Thus, one embodiment of the present invention also includes a light-emitting element including the phosphorescent organometallic iridium complex according to one embodiment of the present invention.

Furthermore, one embodiment of the present invention includes not only a light-emitting device including the light-emitting element but also an electronic device and a lighting device each including the light-emitting device. Accordingly, a light-emitting device in this specification refers to an image display device or a light source (including a lighting device). The light-emitting device also includes the following modules in its category: a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting device by a chip on glass (COG) method.

One embodiment of the present invention can provide a novel phosphorescent organometallic iridium complex. According to one embodiment of the present invention, a phosphorescent organometallic iridium complex which keeps high quantum efficiency and emits phosphorescence in the blue green to red wavelength region can be obtained. In addition, according to one embodiment of the present invention, a light-emitting element, a light-emitting device, an electronic device, or a lighting device each including such a phosphorescent organometallic iridium complex and having high emission efficiency can be provided.

BRIEF DESCRIPTION OF THE DRAWINGS

In the accompanying drawings.

DETAILED DESCRIPTION OF THE INVENTION

Figure 1:
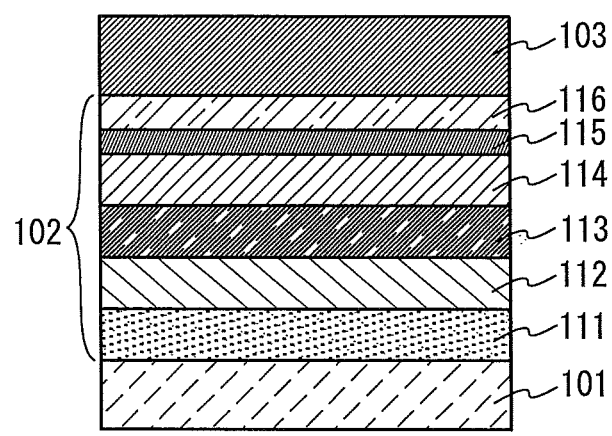
FIG. 1 illustrates a structure of a light-emitting element.

Hereinafter, embodiments of the present invention will be described with reference to the drawings. Note that the present invention is not limited to the following description, and various changes and modifications can be made without departing from the spirit and scope of the invention. Therefore, the present invention should not be construed as being limited to the description in the following embodiments.

Embodiment 1

In this embodiment, phosphorescent organometallic iridium complexes according to embodiments of the present invention are described.

One embodiment of the present invention is a phosphorescent organometallic iridium complex with a ligand having a pyridyl pyrimidine skeleton. As a specific example of the ligand, a ligand having a pyrimidine skeleton having a pyridyl group at the 4-position can be given, and more specifically, a ligand having a 4-(3-pyridyl)pyrimidine skeleton or a 4-(4-pyridyl)pyrimidine skeleton can be given.

Further, one embodiment of the present invention is a phosphorescent organometallic iridium complex with a ligand having a structure represented by the following general formula (G0).

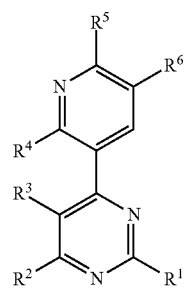

(G0)

In the general formula (G0), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Another embodiment of the present invention is a phosphorescent organometallic iridium complex having a structure represented by the following general formula (G0').

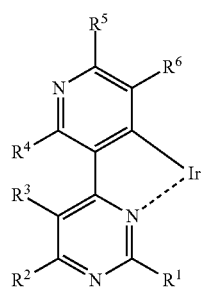

(G0')

In the general formula (G0'), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

In particular, a phosphorescent organometallic iridium complex having the structure which is represented by the general formula (G0') and in which the lowest triplet excited state is formed is preferable because phosphorescence can be efficiently emitted. To achieve such a mode, another skeleton (another ligand) which is included in the phosphorescent organometallic iridium complex may be selected such that the lowest triplet excitation energy of the structure is equal to or lower than the lowest triplet excitation energy of the another skeleton (the another ligand), for example. With such a structure, regardless of what a skeleton (ligand) other than the structure is, the lowest triplet excited state is formed by the structure at last, so that phosphorescence originating from the structure is obtained. Therefore, phosphorescence can be highly efficiently obtained. A typical example is vinyl polymer having the structure as a side chain.

Another embodiment of the present invention is a phosphorescent organometallic iridium complex having a structure represented by the following general formula (G1).

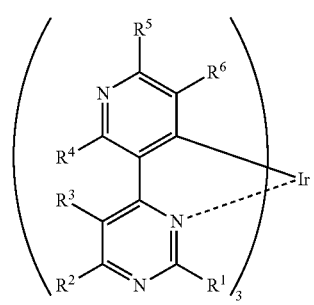

(G1)

In the general formula (G1), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Another embodiment of the present invention is a phosphorescent organometallic iridium complex having a structure represented by the following general formula (G2).

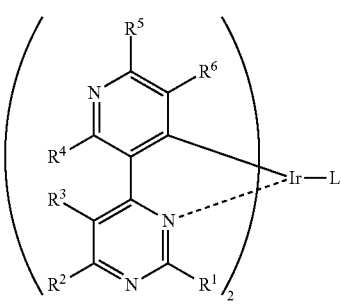

(G2)

In the general formula (G2), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent. Further, L represents a monoanionic ligand.

Here, it is preferable that L that is the monoanionic ligand be any of the following specific examples: a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable. A beta-diketone structure is preferably included because a solubility of a phosphorescent organometallic iridium complex in an organic solvent becomes higher and purification becomes easier. Further, a beta-diketone structure is preferably included because a phosphorescent organometallic iridium complex with high emission efficiency can be obtained. Furthermore, inclusion of a beta-diketone structure has advantages such as a higher sublimation property and excellent evaporativity.

Specifically, L that is the monoanionic ligand is preferably a ligand represented by any of the following general formulae (L1) to (L6).

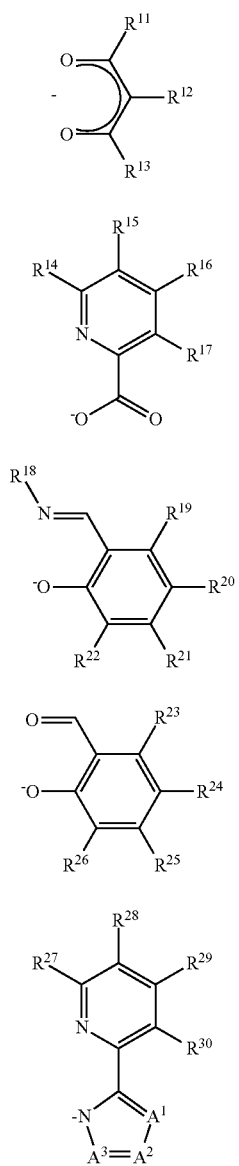

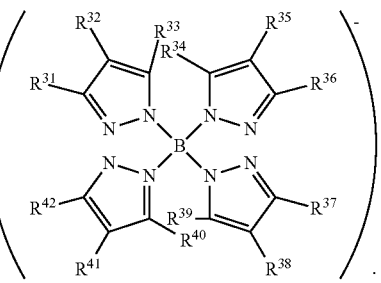

In the general formulae (L1) to (L6), $R^{11}$ to $R^{42}$ separately represent any of hydrogen, a substituted or unsubstituted alkyl group having 1 to 4 carbon atoms, a halogen group, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms. Further, $A^1$ to $A^3$ separately represent any of nitrogen, $sp^2$ hybridized carbon bonded to hydrogen, and $sp^2$ hybridized carbon bonded to any of an alkyl group having 1 to 4 carbon atoms, a halogen group, a haloalkyl group having 1 to 4 carbon atoms, and a phenyl group.

Another embodiment of the present invention is a phosphorescent organometallic iridium complex having a structure represented by the following general formula (G3).

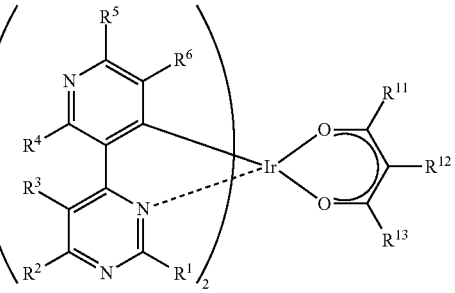

In the general formula (G3), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent. Further, $R^{11}$ to $R^{13}$ separately represent hydrogen or an alkyl group having 1 to 6 carbon atoms.

Note that specific examples of the alkyl group having 1 to 6 carbon atoms in $R^1$ to $R^6$ in the general formulas (G0), (G0'), (G1), (G2), and (G3) and in $R^{11}$ to $R^{13}$ in the general formula (G3) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group. In light of the steric structure and the synthesis yield of the complex, a methyl group, an ethyl group, an isopropyl group, and a tert-butyl group are preferable; a methyl group and a tert-butyl group are particularly preferable.

Here, in any of the above-described phosphorescent organometallic iridium complexes, the pyridyl group bonded to the 4-position of the pyrimidine skeleton preferably has a substituent at an ortho-position ($R^4$ in the general formulas (G1), (G2), and (G3)). Such a structure is preferable because orthometalation proceeds in a selective manner and thus the yield increases. In light of the steric structure and the synthesis yield of the complex, the substituent is preferably a methyl group, an ethyl group, or an isopropyl group, and a methyl group is particularly preferable.

Next, specific structural formulae of the above-described phosphorescent organometallic iridium complexes according to embodiments of the present invention will be shown (the following structural formulae (100) to (121)). Note that the present invention is not limited thereto.

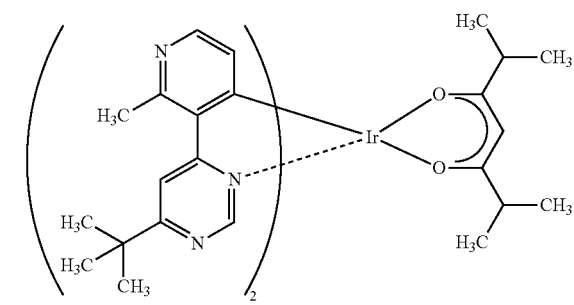

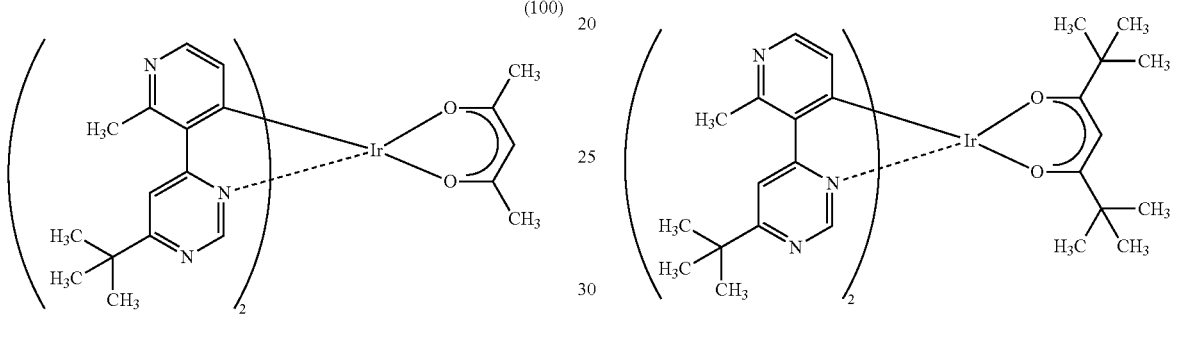

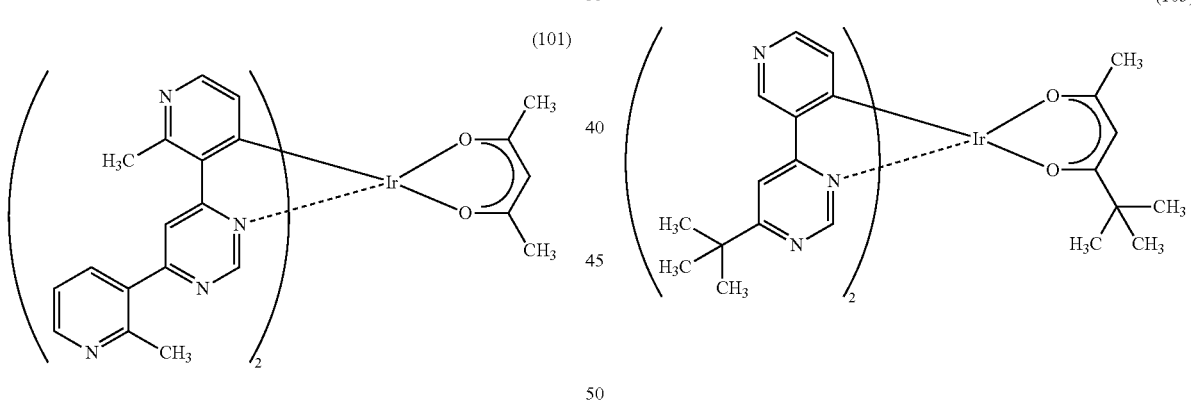

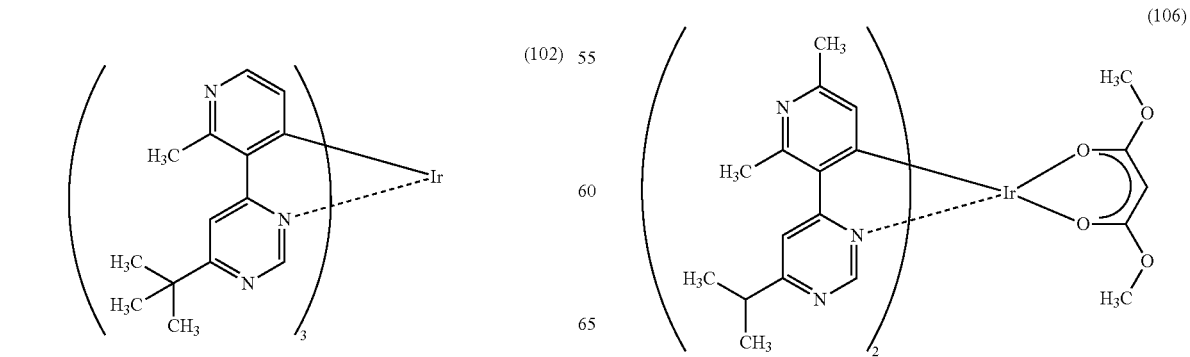

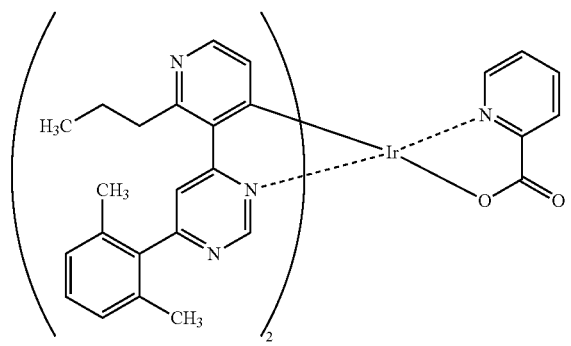
(107)
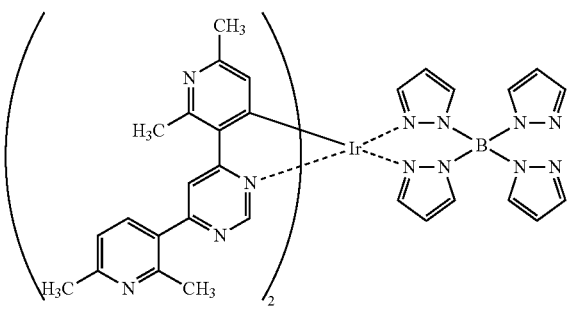
(111)
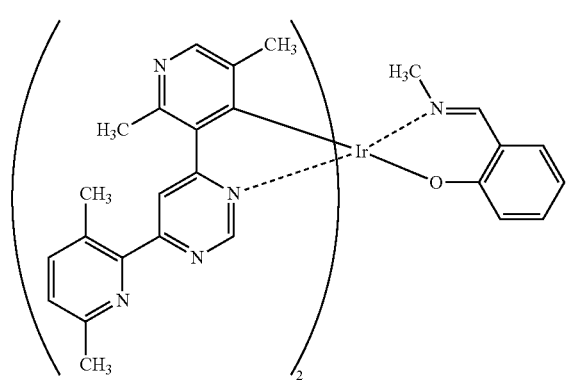
(108)
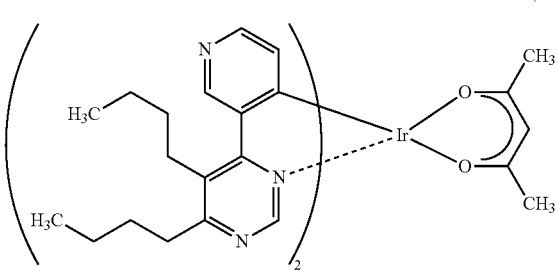
(112)
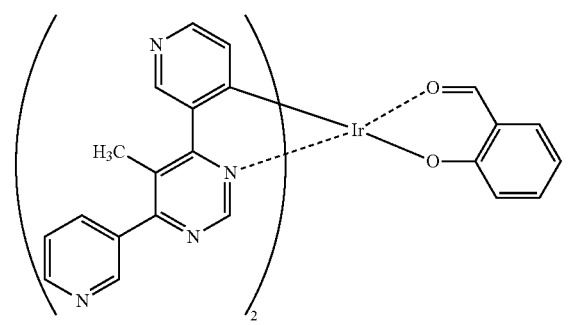
(109)
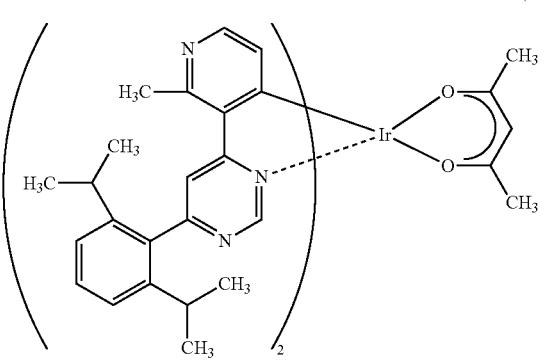
(113)
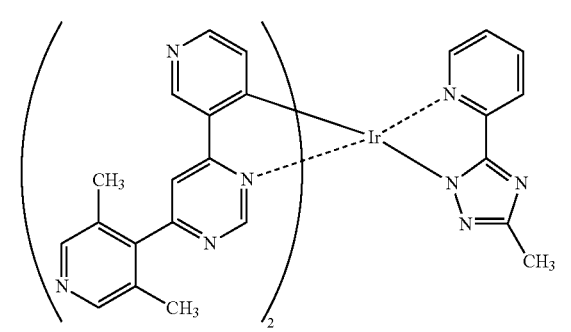
(110)
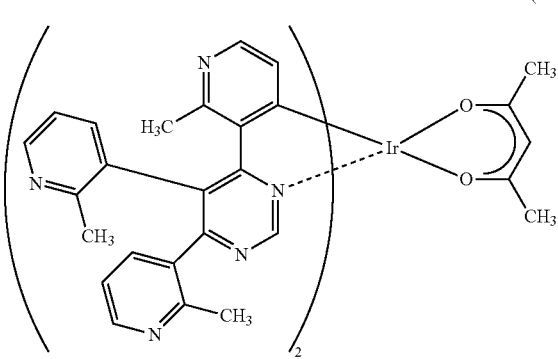
(114)

(115)

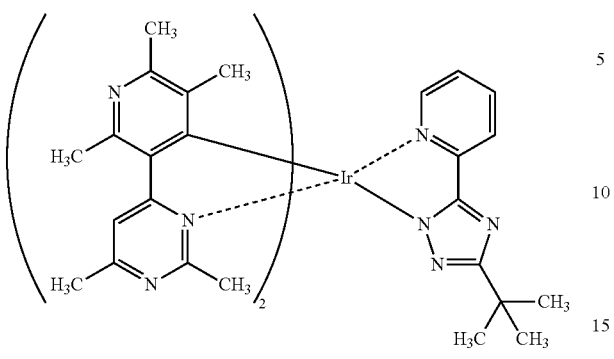

(116)

(117)

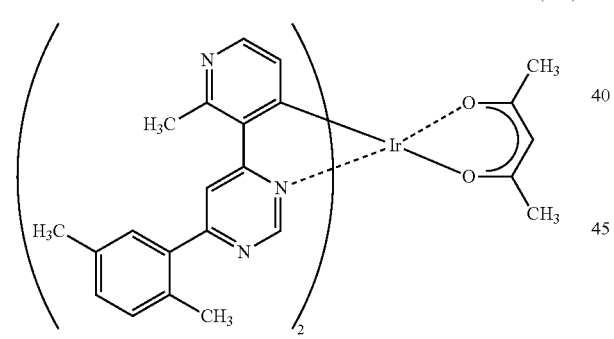

(118)

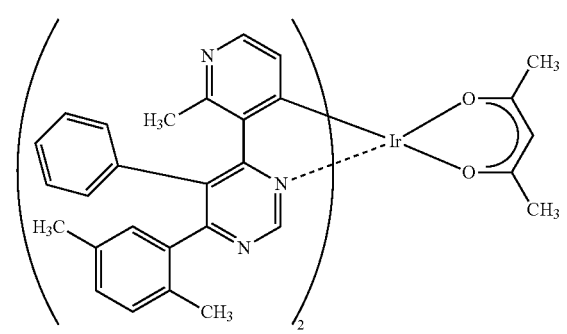

(119)

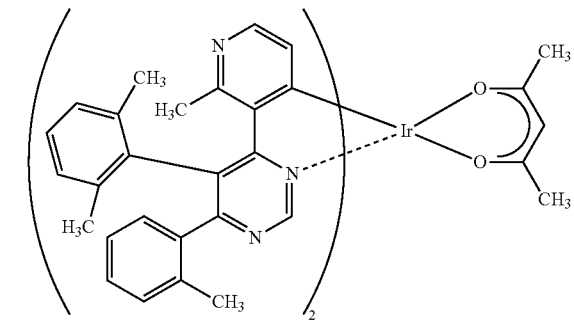

(120)

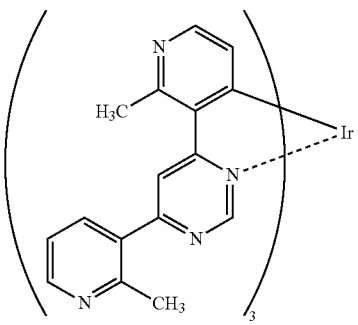

(121)

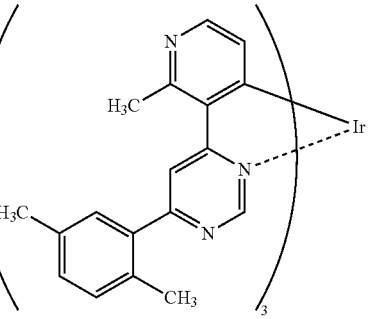

Note that phosphorescent organometallic iridium complexes represented by the structural formulae (100) to (121) are novel substances capable of emitting phosphorescence. Note that there can be geometrical isomers and stereoisomers of these substances depending on the type of the ligand. The phosphorescent organometallic iridium complex according to one embodiment of the present invention includes all of these isomers.

Next, an example of a method for synthesizing a phosphorescent organometallic iridium complex represented by the general formula (G1) is described.

(Method for Synthesizing Phosphorescent Organometallic Iridium Complex Represented by General Formula (G1))

Step 1: Method for Synthesizing 3-Pyridyl Pyrimidine Derivative

First, an example of a method for synthesizing a 3-pyridyl pyrimidine derivative represented by the following general formula (G0) is described.

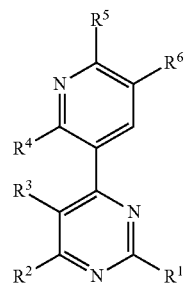

(G0)

In the general formula (G0), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

As illustrated in the following synthetic scheme (Q), the 3-pyridyl pyrimidine derivative represented by the general formula (G0) can be obtained by coupling a boronic acid, a boronate ester, or a cyclic-triolborate salt (A1) with a halogenated pyrimidine compound (A2). As the cyclic-triolborate salt, a lithium salt, a potassium salt, or a sodium salt may be used.

(Q)

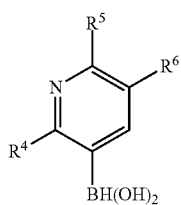

or

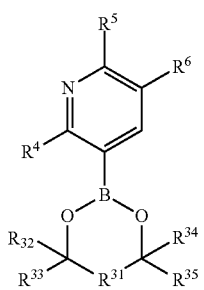 or 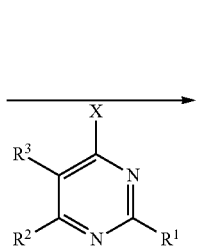 → 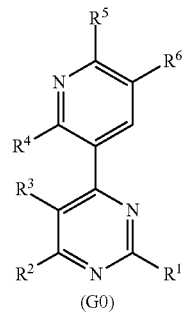

(A2) (G0)

or

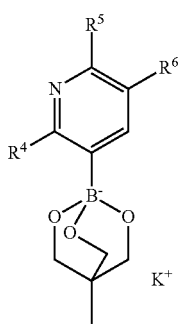

(A1)

In the synthetic scheme (Q), X represents halogen; $R^1$ and $R^4$ to $R^6$ separately represent hydrogen or an alkyl group having 1 to 6 carbon atoms; $R^2$ and $R^3$ separately represent any of hydrogen, an alkyl group having 1 to 6 carbon atoms, a phenyl group that may have a substituent, and a pyridyl group that may have a substituent; $R^{31}$ represents any of a single bond, a methylene group, an ethylidene group, a propylidene group, and an isopropylidene group; and $R^{32}$ to $R^{35}$ may be the same or different from one another, and represent a hydrogen atom or an alkyl group having 1 to 3 carbon atoms. $R^{33}$ and $R^{35}$ may be bonded to each other via a carbon chain to form a ring.

Alternatively, as illustrated in the following synthetic scheme (Q'), the 3-pyridyl pyrimidine derivative represented by the general formula (G0) can be obtained by reacting 1,3-diketone (A1') of pyridyl with amidine (A2').

mixing the 3-pyridyl pyrimidine derivative represented by the general formula (G0) obtained in the above Step 1 with an iridium compound containing halogen (e.g., iridium chloride, iridium bromide, or iridium iodide) or an iridium compound (e.g., an acetylacetonate complex or a diethylsulfide complex) and then by heating the mixture. Note that this heating process may be performed after the 3-pyridyl pyrimidine derivative represented by the general formula (G0) and the iridium compound containing halogen or the iridium compound are dissolved in an alcohol-based solvent (e.g., glycerol, ethylene glycol, 2-methoxyethanol, or 2-ethoxyethanol). There is no particular limitation on a heating means, and an oil bath, a sand bath, or an aluminum block may be used. Alternatively, microwaves can be used as a heating means.

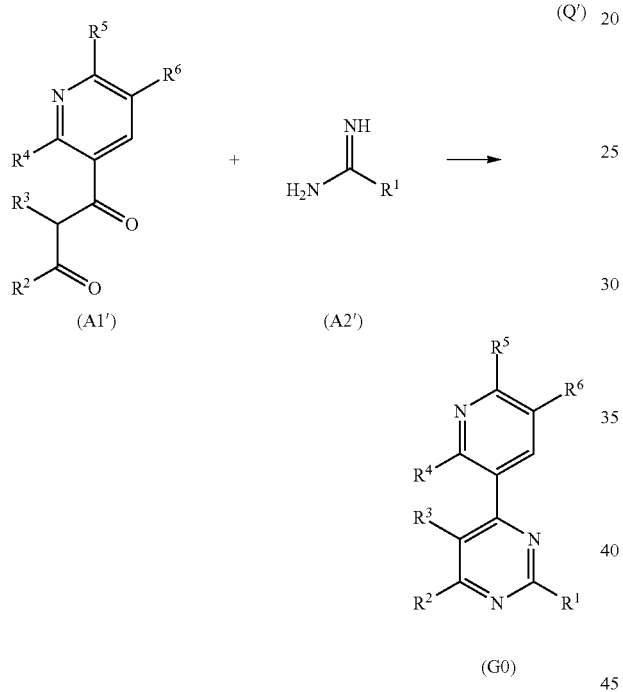

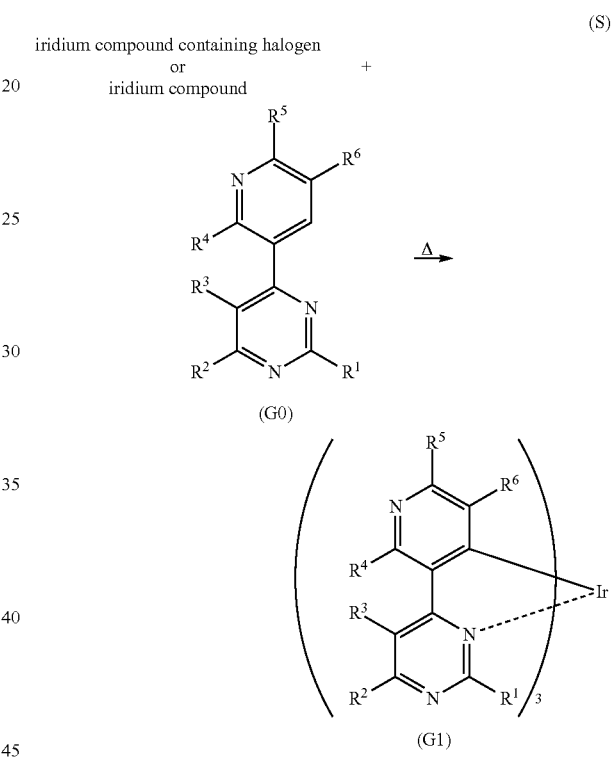

In the synthetic scheme (Q'), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Note that since a wide variety of compounds (A1), (A2), (A1'), and (A2') are commercially available or their synthesis is feasible, a great variety of the 3-pyridyl pyrimidine derivative represented by the general formula (G0) can be synthesized. Thus, one of features of the phosphorescent organometallic iridium complex according to one embodiment of the present invention is the abundance of ligand variation.

Step 2: Method for Synthesizing Phosphorescent Organometallic Iridium Complex Represented by General Formula (G1)

The phosphorescent organometallic iridium complex represented by the general formula (G1) according to one embodiment of the present invention can be synthesized by In a synthetic scheme (S), $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Next, an example of a method for synthesizing a phosphorescent organometallic iridium complex represented by the general formula (G2) is described.

(Method for Synthesizing Phosphorescent Organometallic Iridium Complex Represented by General Formula (G2))

Step 1: Method for Synthesizing 3-Pyridyl Pyrimidine Derivative

Step 1 here is the same as the above-described Step 1 in the method for synthesizing the phosphorescent organometallic iridium complex represented by the general formula (G1) and therefore the description is omitted.

Step 2: Method for Synthesizing Dinuclear Complex Represented by General Formula (P)

A dinuclear complex represented by a general formula (P), which is a novel type of an organometallic complex including a halogen-bridged structure, can be obtained in the following manner. As illustrated in a synthetic scheme (T) below, the 3-pyridyl pyrimidine derivative represented by a general formula (G0) obtained in the above Step 1 and an iridium compound containing halogen (e.g., iridium chloride, iridium bromide, or iridium iodide) are heated in an inert gas atmosphere in bulk, in an alcoholic solvent (e.g., glycerol, ethylene glycol, 2-methoxyethanol, or 2-ethoxyethanol) alone, or in a mixed solvent of water and one or more of the alcoholic solvents. There is no particular limitation on a heating means, and an oil bath, a sand bath, or an aluminum block may be used. Alternatively, microwaves can be used as a heating means.

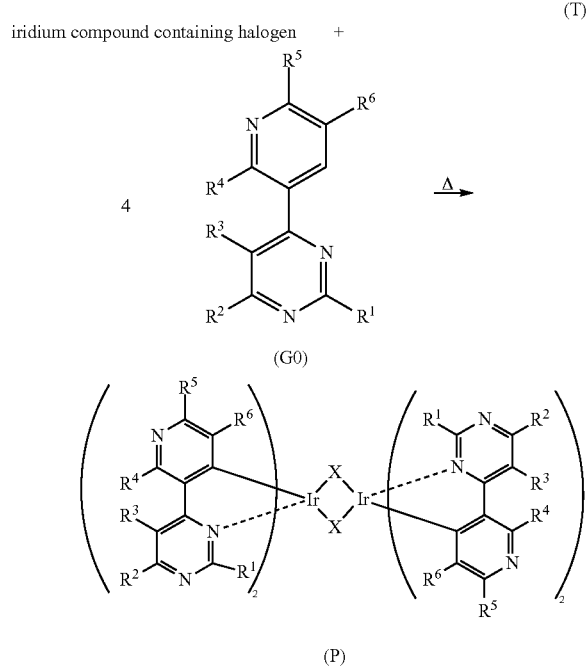

In the synthetic scheme (T), X represents halogen; $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

Step 3: Method for Synthesizing Phosphorescent Organometallic Iridium Complex Represented by General Formula (G2)

Next, as shown in the following synthetic scheme (U), the dinuclear complex represented by the general formula (P) obtained in the above synthetic scheme (T) is reacted with HL which is a material of a monoanionic ligand in an inert gas atmosphere, whereby a proton of HL is separated and L coordinates to the central metal Ir. Thus, the phosphorescent organometallic iridium complex represented by the general formula (G2) according to one embodiment of the present invention can be obtained. There is no particular limitation on a heating means, and an oil bath, a sand bath, or an aluminum block may be used. Alternatively, microwaves can be used as a heating means.

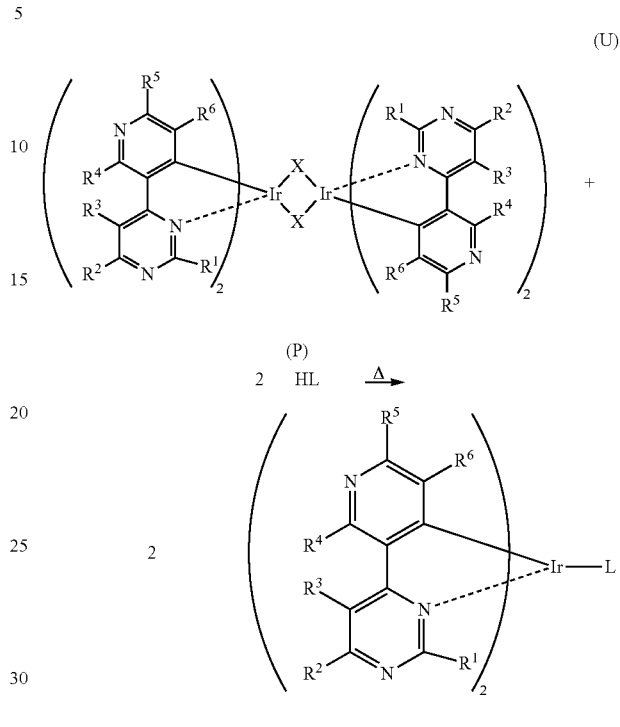

In the synthetic scheme (U), L represents a monoanionic ligand; X represents halogen; $R^1$ and $R^4$ to $R^6$ separately represent hydrogen or an alkyl group having 1 to 6 carbon atoms; and $R^2$ and $R^3$ separately represent any of hydrogen, an alkyl group having 1 to 6 carbon atoms, a phenyl group that may have a substituent, and a pyridyl group that may have a substituent.

The above is the description of the example of a method for synthesizing a phosphorescent organometallic iridium complex according to one embodiment of the present invention; however, the present invention is not limited thereto and any other synthetic method may be employed.

Note that the above-described phosphorescent organometallic iridium complex according to one embodiment of the present invention can emit phosphorescence and thus can be used as a light-emitting material or a light-emitting substance of a light-emitting element.

With the use of the phosphorescent organometallic iridium complex according to one embodiment of the present invention, a light-emitting element, a light-emitting device, an electronic device, or a lighting device with high emission efficiency can be obtained. Further, a light-emitting element, a light-emitting device, an electronic device, or a lighting device with low power consumption can be obtained.

Note that the structure described in this embodiment can be used in combination with any of the structures described in the other embodiments, as appropriate.

Embodiment 2

In this embodiment, a light-emitting element will be described with reference to FIG. 1. In the light-emitting element, the phosphorescent organometallic iridium complex described in Embodiment 1 as one embodiment of the present invention is used for a light-emitting layer.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113.

By voltage application to such a light-emitting element, holes injected from the first electrode 101 side and electrons injected from the second electrode 103 side recombine in the light-emitting layer 113 to raise the phosphorescent organometallic iridium complex to an excited state. Then, light is emitted when the phosphorescent organometallic iridium complex in the excited state relaxes to the ground state. Thus, the phosphorescent organometallic iridium complex in one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer (E) 116 contains a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is manufactured is described.

As the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (e.g., MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property used for the hole-injection layer 111, the hole-transport layer 112, and the charge-generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), [N-(3-methylphenyl)-N-phenylamino] triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Alternatively, the following carbazole derivative can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthryl)phenyl]-9H-carbazole (abbreviation: CzPA). The substances mentioned here are mainly ones that have a hole mobility of $10^{-6}$ cm$^2$/V·s or higher. However, a substance other than the above-described substances may also be used as long as the hole-transport property is higher than the electron-transport property.

Further, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge-generation layer (E) 116, a transition metal oxide or an oxide of a metal belonging to any of Group 4 to Group 8 of the periodic table can be given. Specifically, molybdenum oxide is particularly preferable.

The light-emitting layer 113 contains any of the phosphorescent organometallic iridium complexes described in Embodiment 1 as a guest material serving as a light-emitting substance and a substance that has higher triplet excitation energy than this phosphorescent organometallic iridium complex as a host material.

Preferable examples of the substance (i.e., host material) used for dispersing the phosphorescent organometallic iridium complex are as follows: compounds having an arylamine skeleton, such as 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 2,3-bis(4-diphenylaminophenyl)quinoxaline (abbreviation: TPAQn), and NPB; carbazole derivatives such as CBP and 4,4',4''-tris (N-carbazolyl)triphenylamine (abbreviation: TCTA); nitrogen-containing heteroaromatic compounds such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBIBPDBq-II), 2-[4-(3,6-diphenyl-9H-carbazol-9-yl) phenyl]dibenzo[f,h]quinoxaline (abbreviation: 2CzPDBq-III); and metal complexes such as bis[2-(2-hydroxyphenyl) pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato) aluminum (abbreviation: BAlq), and tris(8-quinolinolato) aluminum (abbreviation: Alq$_3$). Alternatively, a high molecular compound such as PVK can be used.

Note that in the case where the light-emitting layer 113 contains the above-described phosphorescent organometallic iridium complex (guest material) and the host material, phosphorescence with high emission efficiency can be obtained from the light-emitting layer 113.

The electron-transport layer 114 contains a substance having a high electron-transport property. For the electron-transport layer 114, it is possible to use a metal complex such as Alq₃, tris(4-methyl-8-quinolinolato)aluminum (abbreviation: Almq₃), bis(10-hydroxybenzo[h]quinolinato)beryllium (abbreviation: BeBq₂), BAlq, Zn(BOX)₂, or bis[2-(2-hydroxyphenyl)benzothiazolato]zinc (abbreviation: Zn(BTZ)₂). Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)](abbreviation: PF-Py) or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm²/V·s or higher. Note that any substance other than the above substances may be used for the electron-transport layer as long as the electron-transport property is higher than the hole-transport property.

Furthermore, the electron-transport layer is not limited to a single layer, and two or more layers made of the aforementioned substances may be stacked.

The electron-injection layer 115 contains a substance having a high electron-injection property. For the electron-injection layer 115, an alkali metal, an alkaline earth metal, magnesium (Mg), or a compound of any of the above metals such as lithium fluoride (LiF), cesium fluoride (CsF), calcium fluoride (CaF₂), or lithium oxide (LiO$_x$) can be used. Alternatively, a rare earth metal compound like erbium fluoride (ErF₃) can be used. Further alternatively, the above-described substances for forming the electron-transport layer 114 can be used.

Alternatively, a composite material in which an organic compound and an electron donor (donor) are mixed may be used for the electron-injection layer 115. The composite material is superior in an electron-injection property and an electron-transport property, since electrons are generated in the organic compound by the electron donor. In this case, the organic compound is preferably a material excellent in transporting the generated electrons. Specifically, the above-described substances for forming the electron-transport layer 114 (e.g., a metal complex and a heteroaromatic compound) or the like can be used. As the electron donor, any substance which shows an electron-donating property with respect to the organic compound may be used. Preferable examples are an alkali metal, an alkaline earth metal, and a rare earth metal. Specifically, lithium, cesium, calcium, erbium, ytterbium, and magnesium can be given. Further, an alkali metal oxide and an alkaline earth metal oxide are preferable, and a lithium oxide, a calcium oxide, a barium oxide, and the like can be given. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, electron-injection layer 115, and charge-generation layer (E) 116 can be formed by a method such as an evaporation method (e.g., a vacuum evaporation method), an inkjet method, or a coating method.

In the above-described light-emitting element, current flows due to a potential difference generated between the first electrode 101 and the second electrode 103 and holes and electrons recombine in the EL layer 102, so that light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the phosphorescent organometallic iridium complex and thus can have higher efficiency than a light-emitting element using a fluorescent compound.

Note that the light-emitting element described in this embodiment is an example of a light-emitting element manufactured using the phosphorescent organometallic iridium complex according to one embodiment of the present invention. Further, as a structure of a light-emitting device including the above light-emitting element, a passive matrix type light-emitting device and an active matrix type light-emitting device can be manufactured. It is also possible to manufacture a light-emitting device with a microcavity structure including a light-emitting element which is different from the above light-emitting elements as described in another embodiment. Each of the above light-emitting devices is included in the present invention.

Note that there is no particular limitation on a structure of the TFT in the case of manufacturing the active matrix type light-emitting device. For example, a staggered TFT or an inverted staggered TFT can be used as appropriate. Further, a driver circuit formed over a TFT substrate may be formed using both of an n-channel TFT and a p-channel TFT or only either an n-channel TFT or a p-channel TFT. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be used in combination with any of the structures described in the other embodiments, as appropriate.

Embodiment 3

In this embodiment, as one embodiment of the present invention, a light-emitting element in which two or more kinds of organic compounds as well as a phosphorescent organometallic iridium complex are used for a light-emitting layer will be described.

Figure 2:
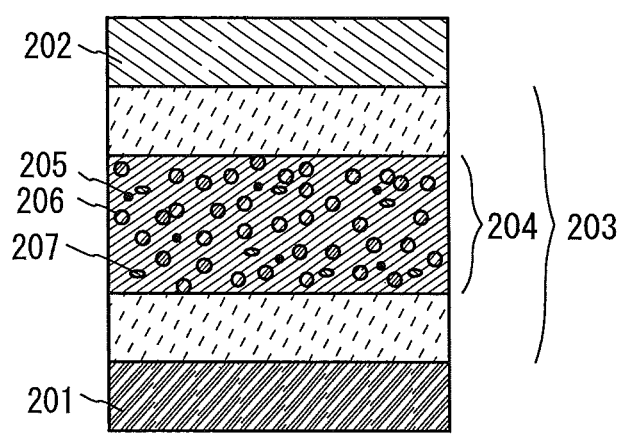
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer (E), and the like. Note that for the hole-injection layer, the hole-transport layer, the electron-transport layer, the electron-injection layer, and the charge-generation layer (E), the substances described in Embodiment 2 can be used.

The light-emitting layer 204 described in this embodiment contains a phosphorescent compound 205 using the phosphorescent organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in the efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound and the second organic compound preferably forms an exciplex (also referred to as excited complex). In this case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound and the second organic compound are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not from the host material, is assumed to occur.

For the phosphorescent compound 205, the phosphorescent organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As a compound which is likely to accept electrons, a π-electron deficient heteroaromatic compound such as a nitrogen-containing heteroaromatic compound is preferable. For example, a quinoxaline derivative and a dibenzoquinoxaline derivative can be given and examples thereof include 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and the like.

As a compound which is likely to accept holes, a π-electron rich heteroaromatic compound (e.g., a carbazole derivative or an indole derivative) or an aromatic amine compound is preferable. For example, the following can be given: 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that although the light-emitting element described in this embodiment is one structural example of a light-emitting element, a light-emitting element having another structure which is described in another embodiment can also be used for a light-emitting device according to one embodiment of the present invention. Further, as a light-emitting device including the above light-emitting element, a passive matrix type light-emitting device and an active matrix type light-emitting device can be manufactured. It is also possible to manufacture a light-emitting device with a microcavity structure including a light-emitting element which is different from the above light-emitting elements as described in another embodiment. Each of the above light-emitting devices is included in the present invention.

Note that there is no particular limitation on the structure of the TFT in the case of manufacturing the active matrix type light-emitting device. For example, a staggered TFT or an inverted staggered TFT can be used as appropriate. Further, a driver circuit formed over a TFT substrate may be formed using both of an n-channel TFT and a p-channel TFT or only either an n-channel TFT or a p-channel TFT. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be used in combination with any of the structures described in the other embodiments, as appropriate.

Embodiment 4

In this embodiment, as one embodiment of the present invention, a light-emitting element (hereinafter referred to as tandem light-emitting element) in which a plurality of EL layers are included so that a charge-generation layer is sandwiched therebetween will be described.

Figure 3A:
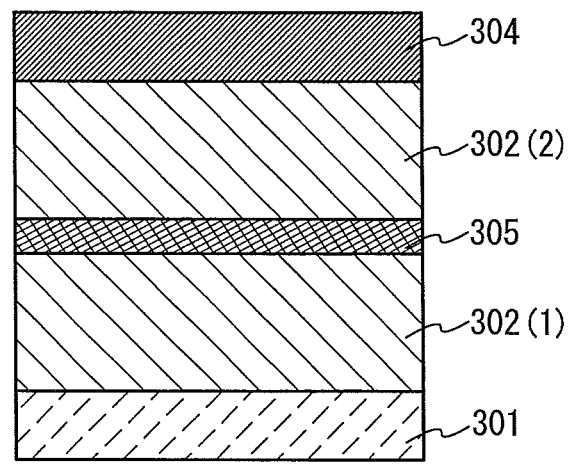
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have structures similar to that described in Embodiment 2, any of the EL layers may have a structure similar to that described in Embodiment 2. In other words, the structures of the first EL layer 302(1) and the second EL layer 302(2) may be the same or different from each other and can be similar to those described in Embodiment 2.

Further, a charge-generation layer (I) 305 is provided between the plurality of EL layers (the first EL layer 302(1) and the second EL layer 302(2)). The charge-generation layer (I) 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge-generation layer (I) 305 injects electrons into the first EL layer 302(1) and injects holes into the second EL layer 302(2).

Note that in terms of light extraction efficiency, the charge-generation layer (I) 305 preferably has a light-transmitting property with respect to visible light (specifically, the charge-generation layer (I) 305 has a visible light transmittance of 40% or more). Further, the charge-generation layer (I) 305 functions even if it has lower conductivity than the first electrode 301 or the second electrode 304.

The charge-generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/V·s or higher. However, substances other than the above substances may be used as long as they are organic compounds in which a hole-transport property is higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air, its hygroscopic property is low, and it is easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as $Zn(BOX)_2$ or $Zn(BTZ)_2$ can be used. Further alternatively, other than such a metal complex, PBD, OXD-7, TAZ, BPhen, BCP, or the like can be used. The substances mentioned here are mainly ones that have an electron mobility of $10^{-6}$ cm$^2$/V·s or higher. Note that any substance other than the above substances may be used as long as the electron-transport property is higher than the hole-transport property.

Further, as the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer (I) 305 by using any of the above materials can suppress an increase in drive voltage caused by the stack of the EL layers.

Figure 3B:
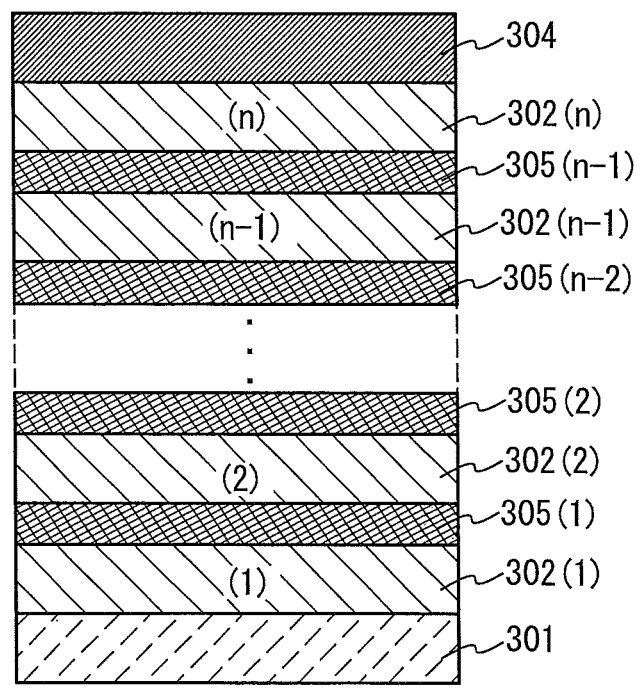

Although this embodiment shows the light-emitting element having two EL layers, the present invention can be similarly applied to a light-emitting element in which n EL layers (n is three or more) are stacked as illustrated in FIG. 3B. In the case where a plurality of EL layers are included between a pair of electrodes as in the light-emitting element according to this embodiment, by provision of a charge-generation layer (I) between the EL layers, light emission in a high luminance region can be obtained with current density kept low. Since the current density can be kept low, the element can have a long lifetime. When the light-emitting element is used for lighting, voltage drop due to resistance of an electrode material can be reduced, thereby achieving homogeneous light emission in a large area. Moreover, a light-emitting device of low power consumption, which can be driven at a low voltage, can be achieved.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. That is, white light emission can be obtained by mixture of light from substances, of which the light emission colors are complementary colors.

Further, the same can be applied to a light-emitting element having three EL layers. For example, the light-emitting element as a whole can provide white light emission when the emission color of a first EL layer is red, the emission color of a second EL layer is green, and the emission color of a third EL layer is blue.

Note that the structure described in this embodiment can be used in combination with any of the structures described in the other embodiments, as appropriate.

Embodiment 5

In this embodiment, as a light-emitting device utilizing phosphorescence according to one embodiment of the present invention, a light-emitting device using a phosphorescent organometallic iridium complex will be described.

Figure 4:
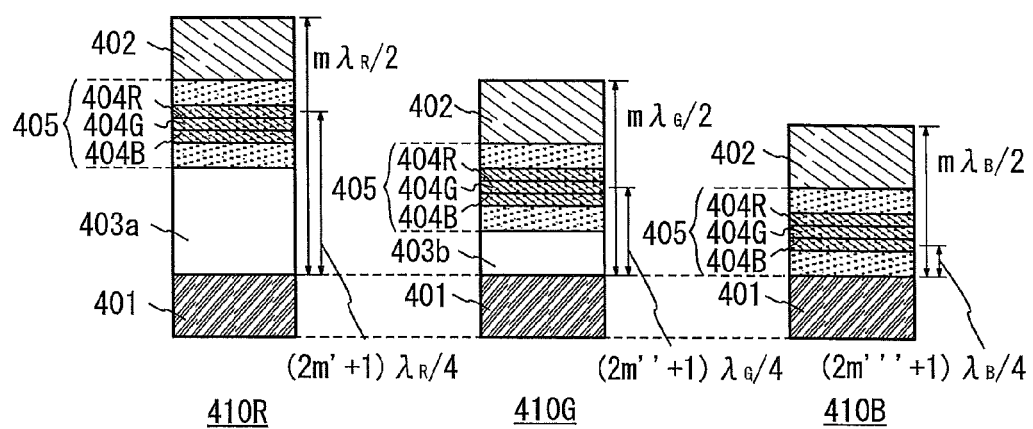
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge-generation layer (E), and the like. Note that the light-emitting layer 404 contains a phosphorescent organometallic iridium complex according to one embodiment of the present invention.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 41 OR has a structure in which a first transparent conductive layer 403a; an EL layer 405 including a first light-emitting layer (B) 404B, a second light-emitting layer (G) 404G, and a third light-emitting layer (R) 404R; and the semi-transmissive and semi-reflective electrode 402 are sequentially stacked over the reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength range from 420 nm to 480 nm. The second light-emitting layer (G) 404G emits light ($\lambda_G$) having a peak in a wavelength range from 500 nm to 550 nm. The third light-emitting layer (R) 404R emits light ($\lambda_R$) having a peak in a wavelength range from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1\times10^{-2}$ $\Omega$cm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1\times10^{-2}$ $\Omega$cm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness $((2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value $((2m'+1)\lambda_R/4$, where m' is a natural number), the phases of the first reflected light and the first incident light can be aligned with each other and the light emitted from the third light-emitting layer (R) 404R can be amplified.

Note that, strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R; therefore, it is assumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness $((2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value $((2m''+1)\lambda_G/4$, where m'' is a natural number), the phases of the second reflected light and the second incident light can be aligned with each other and the light emitted from the second light-emitting layer (G) 404G can be amplified.

Note that, strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is assumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that, strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is assumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided so that a charge-generation layer is sandwiched therebetween in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being used for a color display (image display device) including pixels of three or more colors but may also be used for lighting or the like.

Embodiment 6

In this embodiment, a light-emitting device including a light-emitting element in which the phosphorescent organometallic iridium complex that is one embodiment of the present invention is used in a light-emitting layer will be described.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix type light-emitting device is described with reference to FIGS. 5A and 5B.

Figure 5A:
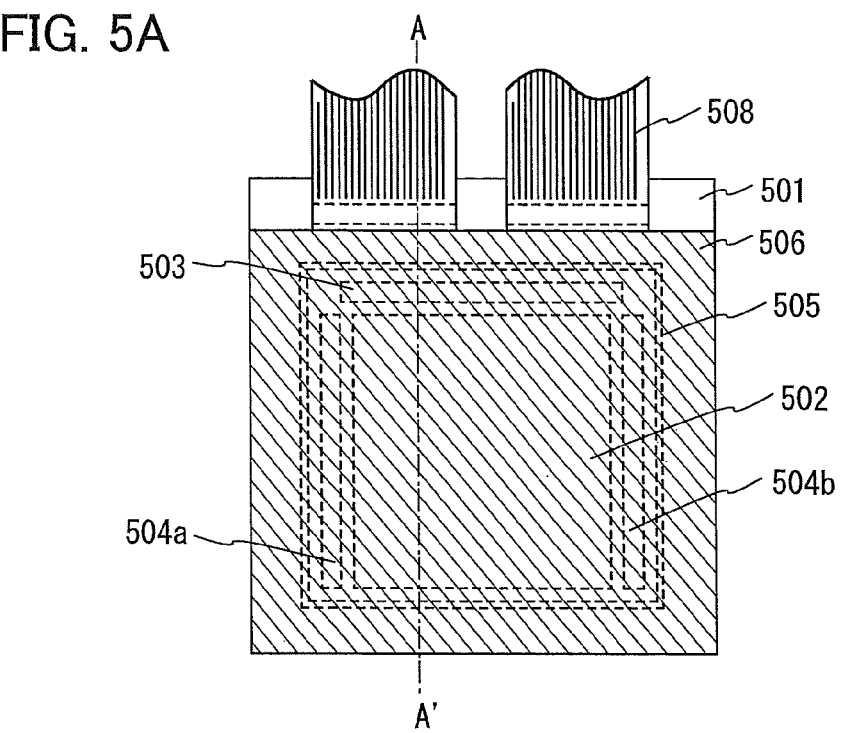
FIGS. 5A and 5B illustrate a light-emitting device.
Figure 5B:
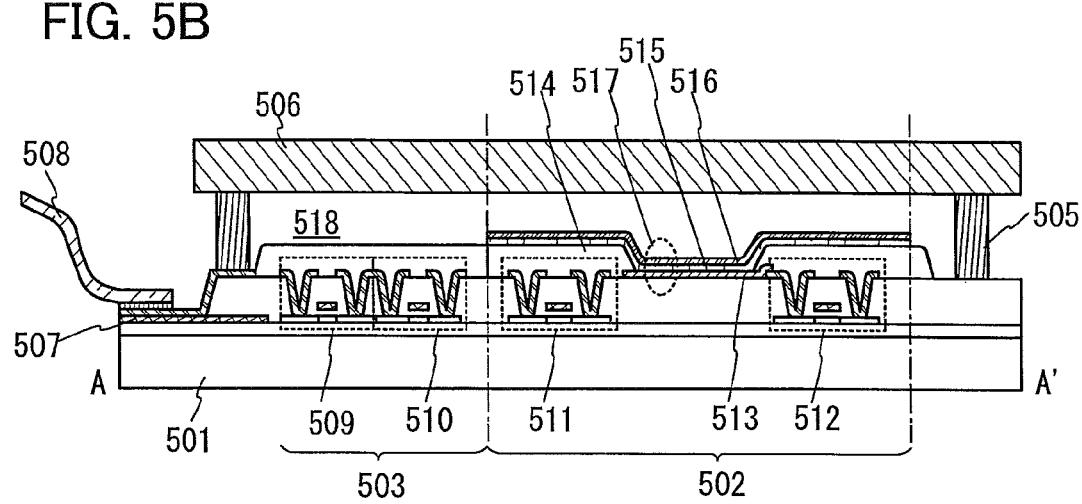

Note that FIG. 5A is a top view illustrating a light-emitting device and FIG. 5B is a cross-sectional view taken along chain line A-A' in FIG. 5A. The active matrix type light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portion 504, is provided. Here, an example is described in which a flexible printed circuit (FPC) 508 is provided as the external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 5B. The driver circuit portion and the pixel portion are formed over the element substrate 501; here are illustrated the driver circuit portion 503 which is the source line driver circuit and the pixel portion 502.

An example is illustrated in which a CMOS circuit which is a combination of an n-channel TFT 509 and a p-channel TFT 510 is formed as the driver circuit portion 503. Note that a circuit included in the driver circuit portion may be formed using various CMOS circuits, PMOS circuits, or NMOS circuits. Although a driver integrated type in which the driver circuit is formed over the substrate is described in this embodiment, the driver circuit is not necessarily formed over the substrate, and the driver circuit can be formed outside the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

In addition, in order to obtain favorable coverage by a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. The insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided which contains the phosphorescent organometallic iridium complex according to one embodiment of the present invention. Further, in the EL layer 515, a hole-injection layer, a hole-transport layer, an electron-transport layer, an electron-injection layer, a charge-generation layer, and the like can be provided as appropriate in addition to the light-emitting layer.

Note that a light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to an FPC 508 which is an external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, and B) are selectively formed in the pixel portion 502, so that a light-emitting device capable of full color display can be obtained. Alternatively, a light-emitting device which is capable of full color display may be manufactured by a combination with color filters.

Further, the sealing substrate 506 is attached to the element substrate 501 with the sealant 505, so that a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. A material used for these is desirably a material which does not transmit moisture or oxygen as much as possible. As the sealing substrate 506, a plastic substrate formed of fiber-glass-reinforced plastics (FRP), polyvinyl fluoride (PVF), polyester, acrylic, or the like can be used besides a glass substrate or a quartz substrate.

As described above, the active matrix type light-emitting device can be obtained.

Note that the structure described in this embodiment can be used in combination with any of the structures described in the other embodiments, as appropriate.

Embodiment 7

In this embodiment, examples of a variety of electronic devices which are completed using a light-emitting device will be described with reference to FIGS. 6A to 6D and FIGS. 7A to 7C. The phosphorescent organometallic iridium complex according to one embodiment of the present invention is used for the light-emitting devices.

Examples of the electronic devices in which the light-emitting device is used are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are shown in FIGS. 6A to 6D.

Figure 6A:
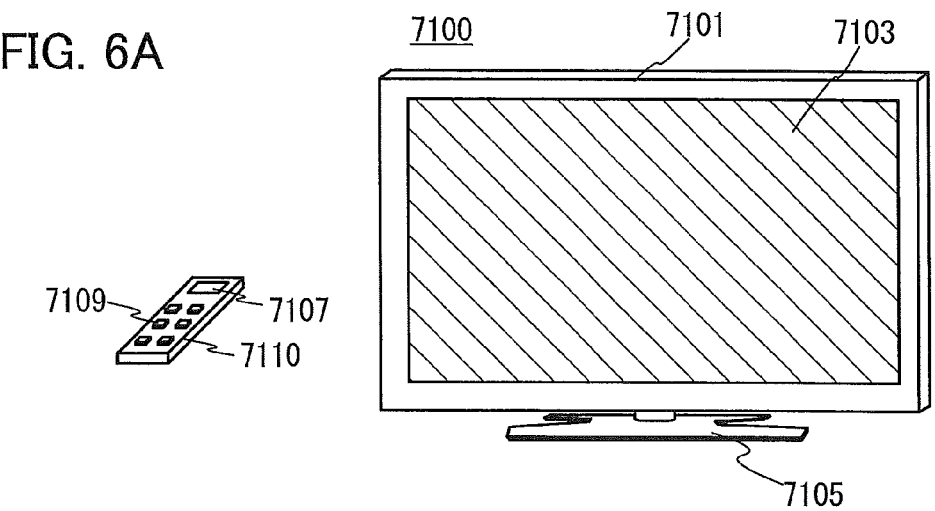
FIGS. 6A to 6D illustrate electronic devices.

FIG. 6A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
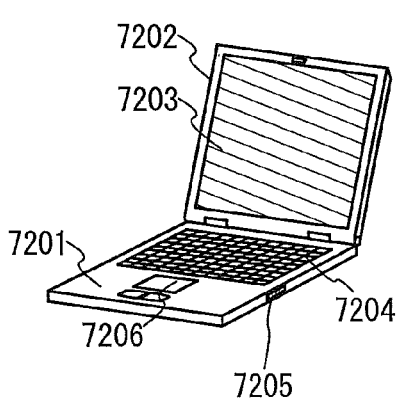

FIG. 6B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 6C:
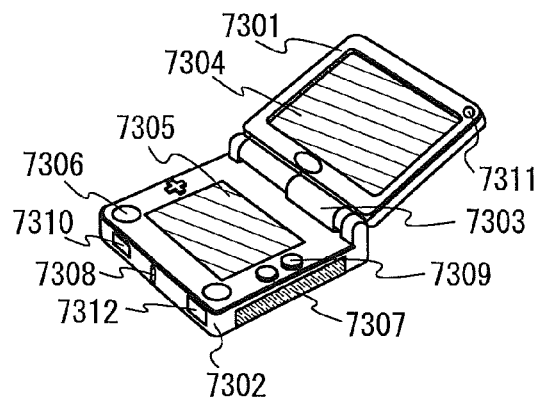

FIG. 6C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 6C has a function of reading a program or data stored in a recording medium to display it in the display portion, and a function of sharing information with another portable game machine by wireless communication. Note that the functions of the portable game machine illustrated in FIG. 6C are not limited to these functions, and the portable amusement machine can have various functions.

Figure 6D:
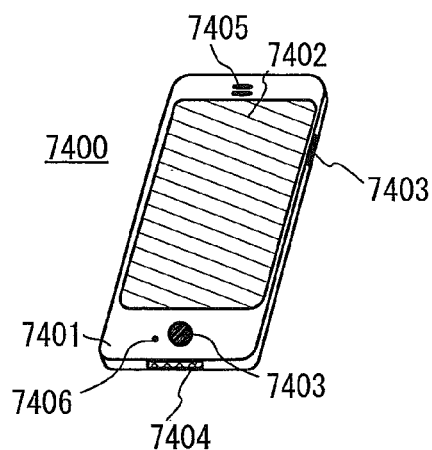

FIG. 6D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 6D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 7A:
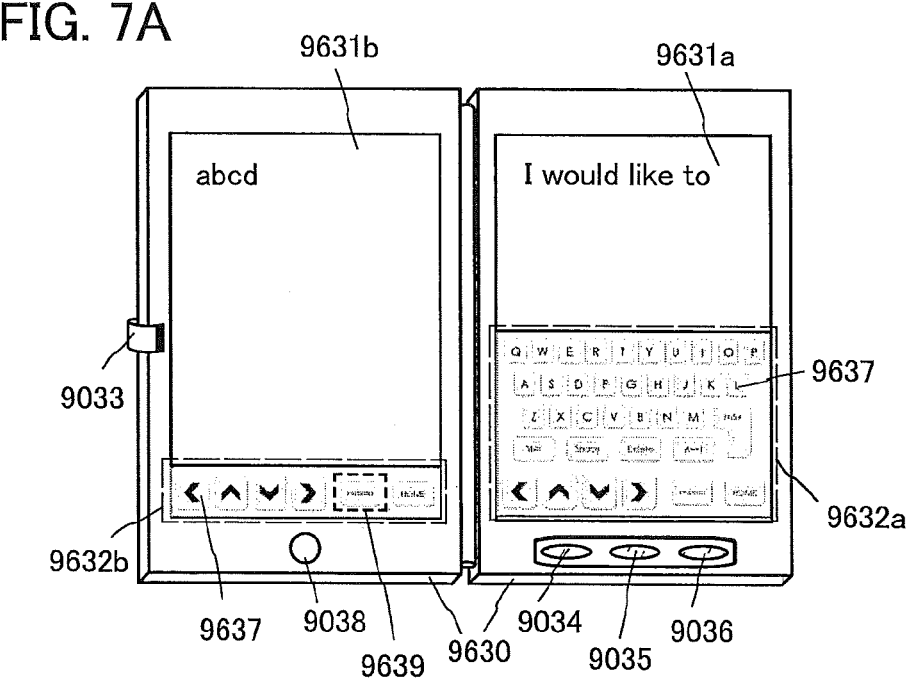
FIGS. 7A to 7C illustrate an electronic device.
Figure 7B:
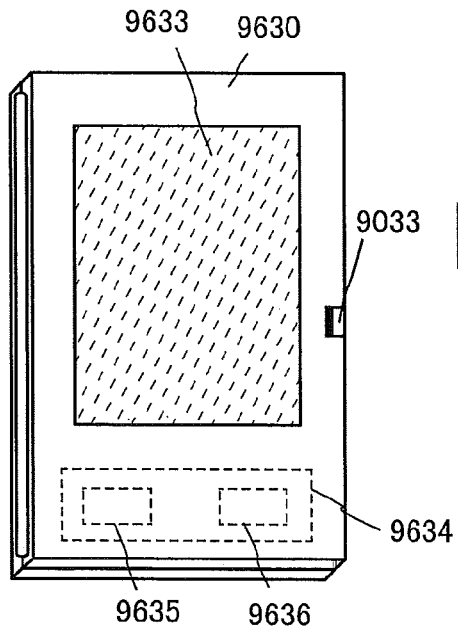

FIGS. 7A and 7B illustrate a tablet terminal that can be folded. In FIG. 7A, the tablet terminal is opened, and includes a housing 9630, a display portion 9631*a*, a display portion 9631*b*, a display-mode switching button 9034, a power button 9035, a power-saving-mode switching button 9036, a clip 9033, and an operation button 9038. The tablet terminal is manufactured using the light-emitting device for one or both of the display portion 9631*a* and the display portion 9631*b*.

A touch panel area 9632*a* can be provided in a part of the display portion 9631*a*, in which area, data can be input by touching displayed operation keys 9637. Note that FIG. 7A shows, as an example, that half of the area of the display portion 9631*a* has only a display function and the other half of the area has a touch panel function. However, the structure of the display portion 9631*a* is not limited to this, and all the area of the display portion 9631*a* may have a touch panel function. For example, all the area of the display portion 9631*a* can display keyboard buttons and serve as a touch panel while the display portion 9631*b* can be used as a display screen.

Like the display portion 9631*a*, part of the display portion 9631*b* can be a touch panel area 9632*b*. When a finger, a stylus, or the like touches the place where a keyboard-display switching button 9639 is displayed in the touch panel, keyboard buttons can be displayed on the display portion 9631*b*.

Touch input can be performed concurrently on the touch panel areas 9632*a* and 9632*b*.

The display-mode switching button 9034 can switch display orientation (e.g., between landscape mode and portrait mode) and select a display mode (switch between monochrome display and color display), for example. With the power-saving-mode switching button 9036, the luminance of display can be optimized in accordance with the amount of external light at the time when the tablet terminal is in use, which is detected with an optical sensor incorporated in the tablet terminal. The tablet terminal may include another detection device such as a sensor for detecting orientation (e.g., a gyroscope or an acceleration sensor) in addition to the optical sensor.

Although the display portion 9631*a* and the display portion 9631*b* have the same display area in FIG. 7A, one embodiment of the present invention is not limited to this example. The display portion 9631*a* and the display portion 9631*b* may have different areas or different display quality. For example, one of them may be a display panel that can display higher-definition images than the other.

FIG. 7B illustrates the tablet terminal folded, which includes the housing 9630, a solar battery 9633, a charge and discharge control circuit 9634, a battery 9635, and a DCDC converter 9636. Note that FIG. 7B shows an example in which the charge and discharge control circuit 9634 includes the battery 9635 and the DCDC converter 9636.

Since the tablet terminal can be folded in two, the housing 9630 can be closed when the tablet terminal is not in use. Thus, the display portions 9631*a* and 9631*b* can be protected, thereby providing a tablet terminal with high endurance and high reliability for long-term use.

The tablet terminal illustrated in FIGS. 7A and 7B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that the solar battery 9633 can be provided on one or both surfaces of the housing 9630, so that the battery 9635 can be charged efficiently, which is preferable. When a lithium ion battery is used as the battery 9635, there is an advantage of downsizing or the like.

Figure 7C:
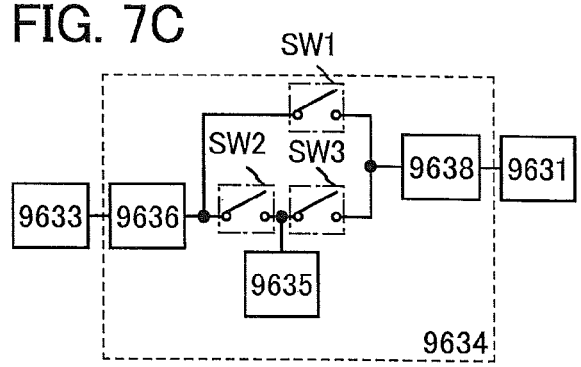

The structure and operation of the charge and discharge control circuit 9634 illustrated in FIG. 7B are described with reference to a block diagram of FIG. 7C. FIG. 7C illustrates the solar battery 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 in FIG. 7B.

First, an example of operation in the case where power is generated by the solar battery 9633 using external light is described. The voltage of power generated by the solar battery is raised or lowered by the DCDC converter 9636 so that the power has a voltage for charging the battery 9635. When the display portion 9631 is operated with the power from the solar battery 9633, the switch SW1 is turned on and the voltage of the power is raised or lowered by the converter 9638 to a voltage needed for operating the display portion 9631. In addition, when display on the display portion 9631 is not performed, the switch SW1 is turned off and a switch SW2 is turned on so that charge of the battery 9635 may be performed.

Here, the solar battery 9633 is shown as an example of a power generation means; however, there is no particular limitation on a way of charging the battery 9635, and the battery 9635 may be charged with another power generation means such as a piezoelectric element or a thermoelectric conversion element (Peltier element). For example, the battery 9635 may be charged with a non-contact power transmission module that transmits and receives power wirelessly (without contact) to charge the battery or with a combination of other charging means.

It is needless to say that one embodiment of the present invention is not limited to the electronic device illustrated in FIGS. 7A to 7C as long as the display portion described in the above embodiment is included.

As described above, the electronic devices can be obtained by using the light-emitting device according to one embodiment of the present invention. Application range of the light-emitting device is so wide that the light-emitting device can be applied to electronic devices in a variety of fields.

Note that the structure described in this embodiment can be used in combination with any of the structures described in the other embodiments, as appropriate.

Embodiment 8

In this embodiment, examples of a lighting device in which a light-emitting device including the phosphorescent organometallic iridium complex according to one embodiment of the present invention is used will be described with reference to FIG. 8.

Figure 8:
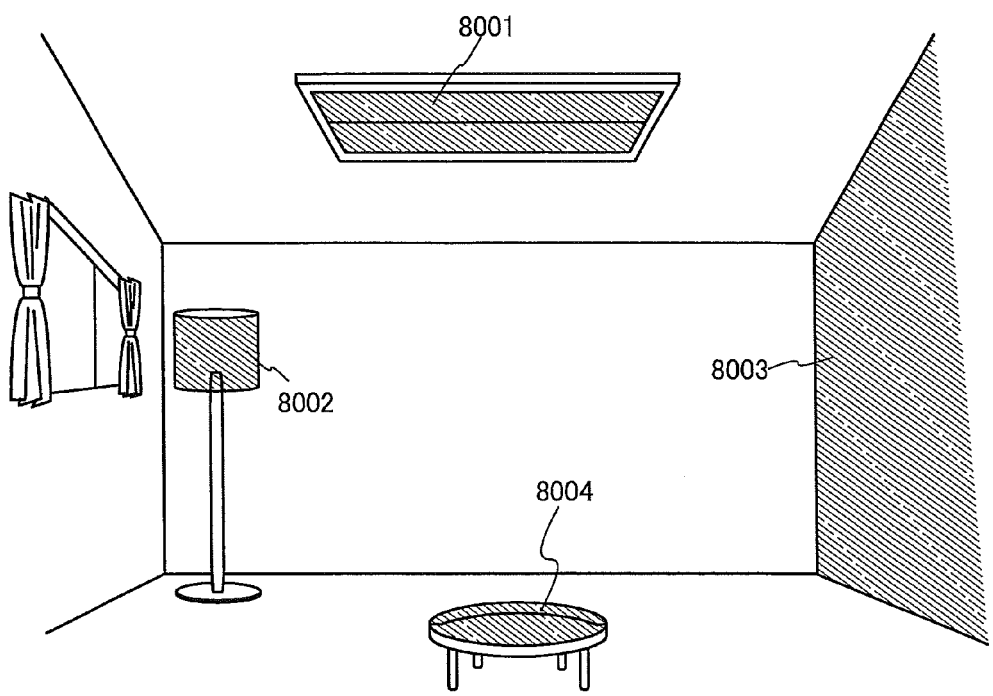
FIG. 8 illustrates lighting devices.

FIG. 8 illustrates an example in which the light-emitting device is used as an indoor lighting device 8001. Note that since the area of the light-emitting device can be increased, a lighting device having a large area can also be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices in which the light-emitting device is used can be obtained. Note that such lighting devices are also embodiments of the present invention.

Note that the structure described in this embodiment can be used in combination with any of the structures described in the other embodiments, as appropriate.

Example 1

Synthetic Example 1

This example shows a method for synthesizing the phosphorescent organometallic iridium complex bis[2-methyl-3-(6-tert-butyl-4-pyrimidinyl-κN3)pyridyl-κC4](2,4-pentanedionato-κ²O, O')iridium(III) (abbreviation: [Ir(tBumpypm)₂(acac)]) represented by the structural formula (100) in Embodiment 1 according to one embodiment of the present invention. A structure of [Ir(tBumpypm)₂(acac)] (abbreviation) is shown below.

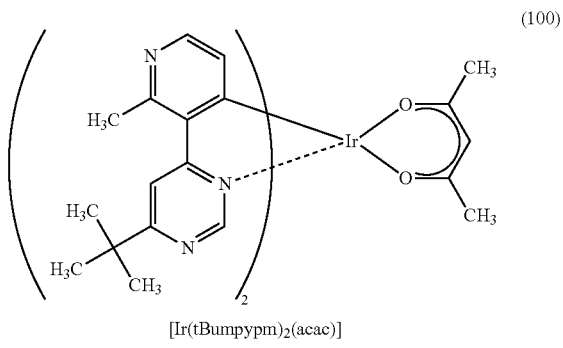

[Ir(tBumpypm)₂(acac)]

(100)

Step 1: Synthesis of 4-Hydroxy-6-tert-butylpyrimidine

First, 7.2 g of formamidine acetate, 7.5 g of sodium methoxide, and 70 mL of methanol were put in a 100 mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated brine, and anhydrate magnesium sulfate was added to the organic layer for drying. The obtained mixture was subjected to gravity filtration, and the filtrate was condensed to give a solid. This solid was washed with ethyl acetate to give 4-hydroxy-6-tert-butylpyrimidine (white solid, yield of 49%). A synthetic scheme of Step 1 is shown in (a-1) below.

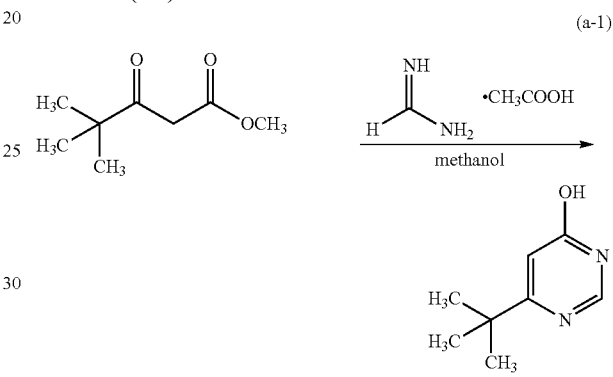

(a-1)

Step 2: Synthesis of 4-Chloro-6-tert-butylpyrimidine

Next, 4.7 g of 4-hydroxy-6-tert-butylpyrimidine obtained in Step 1 and 14 mL of phosphoryl chloride were put in a 50 mL three-neck flask, and the mixture was heated and refluxed for 1.5 hours. After the reflux, phosphoryl chloride was distilled off under reduced pressure. The obtained residue was dissolved in dichloromethane, and washed with water and then a saturated aqueous solution of sodium hydrogen carbonate. Anhydrate magnesium sulfate was added to the obtained organic layer for drying. This mixture was subjected to gravity filtration, and the filtrate was condensed to give a solid. This solid was purified by silica gel column chromatography. As a developing solvent, a mixed solvent of hexane and ethyl acetate in a ratio of 10:1 (v/v) was used. The obtained fraction was condensed to give 4-chloro-6-tert-butylpyrimidine (white solid, yield of 78%). A synthetic scheme of Step 2 is shown in (a-2) below.

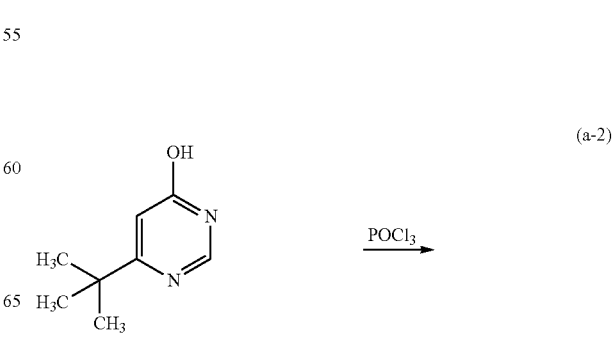

(a-2)

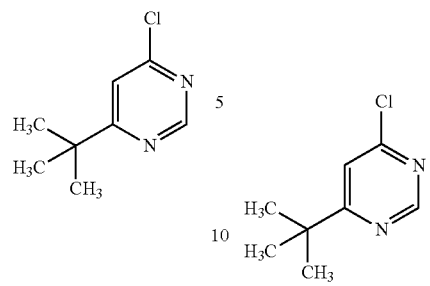

Step 3: Synthesis of 4-(2-Methylpyridin-3-yl)-6-tert-butylpyrimidine (abbreviation: HtBumpypm)

Next, 2.0 g of 4-chloro-6-tert-butylpyrimidine obtained in Step 2, 3.0 g of 2-methylpyridine-3-boronic acid pinacol ester, 17 mL of 1M aqueous solution of potassium acetate, 17 mL of 1M aqueous solution of sodium carbonate, and 40 mL of acetonitrile were put in a 100 mL round-bottom flask, and the air in the flask was replaced with argon. To this mixture, 0.78 g of tetrakis(triphenylphosphine)palladium(0) was added, and the mixture was irradiated with microwaves under conditions of 100° C. and 100 W for 1 hour to cause a reaction. This reaction mixture was extracted with ethyl acetate, and washing with saturated brine was performed. Anhydrous magnesium sulfate was added to the obtained solution of the extract for drying, and the resulting mixture was gravity-filtered to give a filtrate. The resulting filtrate was dissolved in a mixed solvent of ethyl acetate and hexane, and the mixture was filtered through Celite, alumina, and Celite. The resulting filtrate was purified by silica gel column chromatography. As a developing solvent, a mixed solvent of hexane and ethyl acetate in a ratio of 3:2 (v/v) was used. The obtained fractions were condensed to give an oily substance. This oily substance was dissolved in a mixed solvent of hexane and ethyl acetate, and the solution was filtered through a filter aid in which Celite, alumina, and Celite were stacked in this order. The resulting filtrate was condensed to give 4-(2-methylpyridin-3-yl)-6-tert-butylpyrimidine (abbreviation: HtBumpypm) (light-yellow oily substance, yield of 92%). A synthetic scheme of Step 3 is shown in (a-3) below.

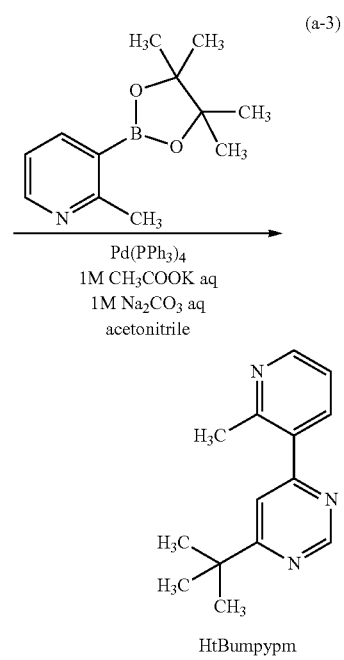

Step 4: Synthesis of Di-μ-chloro-tetrakis[2-methyl-3-(6-tert-butyl-4-pyrimidinyl-κN3)pyridyl-κC4]diiridium (III) (abbreviation: [Ir(tBumpypm)₂Cl]₂)

Next, 2.0 g of the ligand HtBumpypm obtained in the above Step 3, 1.1 g of iridium chloride, 21 mL of 2-ethoxyethanol, and 7 mL of water were put in a 50 mL recovery flask, and the air in the flask was replaced with argon. This reaction container was heated by irradiation with microwaves under conditions of 100° C. and 100 W for 1 hour to cause a reaction. After a predetermined time elapsed, the obtained reaction solution was condensed to give a dinuclear complex [Ir(tBumpypm)₂Cl]₂ (orange oily substance, yield of 100%). A synthetic scheme of Step 4 is shown in (a-4) below.

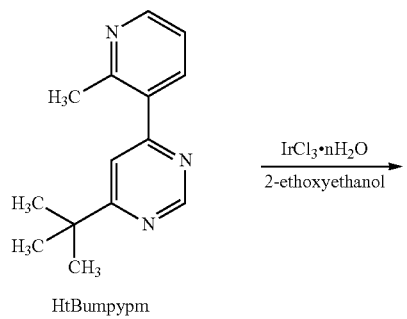

-continued

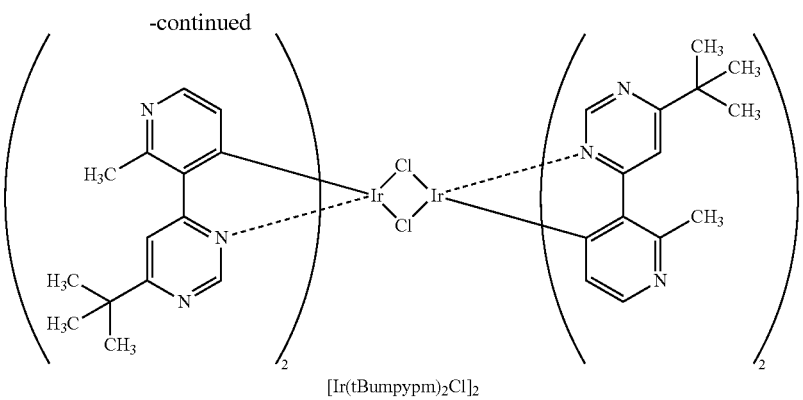

[Ir(tBumpypm)₂Cl]₂

Step 5: Synthesis of Bis[2-methyl-3-(6-tert-butyl-4-pyrimidinyl-κN3)pyridyl-κC4](2,4-pentanedionato-κ²O, O')iridium(III) (abbreviation: [Ir(tBumpypm)₂(acac)])

Next, 2.5 g of the dinuclear complex [Ir(tBumpypm)₂Cl]₂ obtained in the above Step 4, 1.9 g of sodium carbonate, 0.55 g of acetylacetone, and 20 mL of 2-ethoxyethanol were put in a 100 mL round-bottom flask, and the air in the flask was replaced with argon. This reaction container was irradiated with microwaves under conditions of 100° C. and 120 W for 1 hour to cause a reaction. After a predetermined time elapsed, the obtained reaction mixture was condensed, and ethanol was added thereto to give a sediment. This mixture was suction-filtered, and the resulting solid was washed with ethanol to give the phosphorescent organometallic iridium complex [Ir(tBumpypm)₂(acac)] according to one embodiment of the present invention (yellow powder, yield of 24%). A synthetic scheme of Step 5 is shown in (a-5) below.

(a-5)

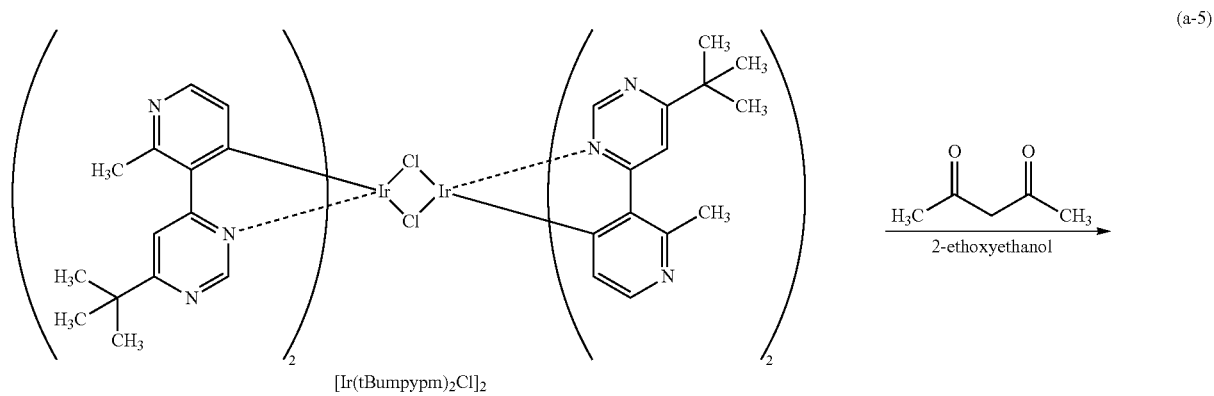

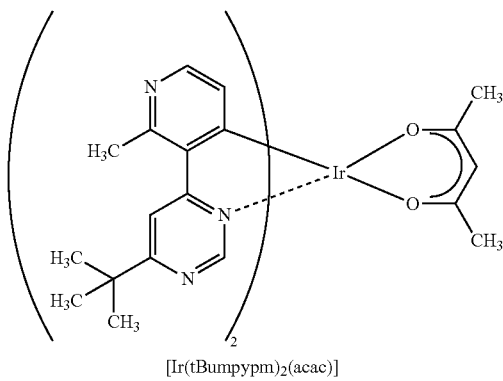

[Ir(tBumpypm)₂(acac)]

Figure 9:
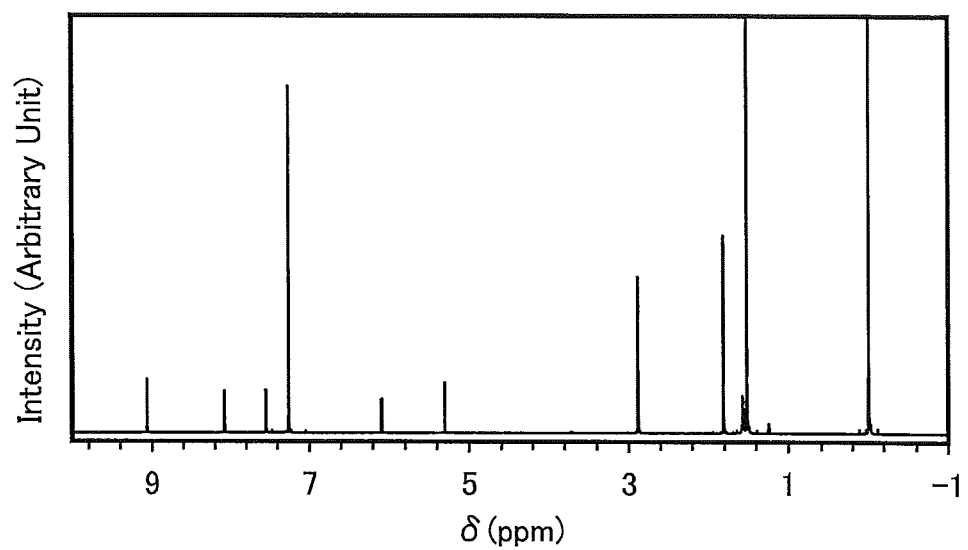
FIG. 9 shows a $^1$H-NMR chart of a phosphorescent organometallic iridium complex represented by a structural formula (100)

Results of analysis of the yellow powder obtained in the above Step 5 by nuclear magnetic resonance spectrometry ($^1$H-NMR) are shown below. The $^1$H-NMR chart is shown in FIG. 9. These results revealed that the phosphorescent organometallic iridium complex [Ir(tBumpypm)$_2$(acac)] (abbreviation) represented by the structural formula (100) according to one embodiment of the present invention was obtained in Synthetic Example 1.

$^1$H-NMR. δ (CDCl$_3$): 1.52 (s, 18H), 1.81 (s, 6H), 2.89 (s, 6H), 5.3 (s, 1H), 6.09 (d, 2H), 6.54 (d, 2H), 8.08 (s, 2H), 9.06 (d, 2H).

Figure 10:
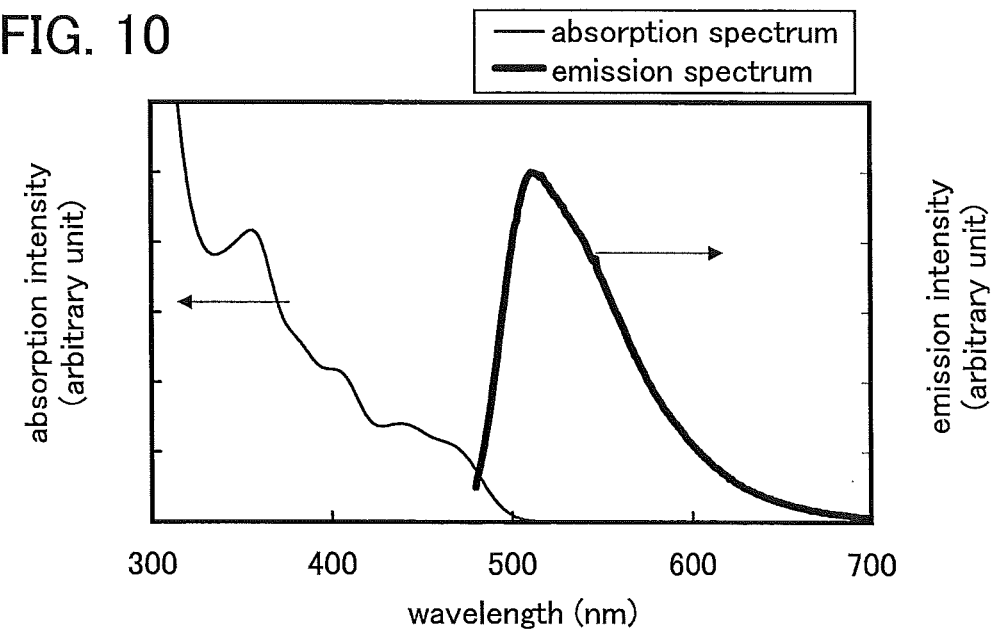
FIG. 10 shows an ultraviolet-visible absorption spectrum and an emission spectrum of the phosphorescent organometallic iridium complex represented by the structural formula (100)

Next, an analysis of [Ir(tBumpypm)$_2$(acac)] (abbreviation) was conducted by an ultraviolet-visible (UV) absorption spectrometry. The UV spectrum was measured with an ultraviolet-visible spectrophotometer (V-550, produced by JASCO Corporation) using a dichloromethane solution (0.083 mmol/L) at room temperature. Further, an emission spectrum of [Ir(tBumpypm)$_2$(acac)] (abbreviation) was measured. The emission spectrum was measured with a fluorescence spectrophotometer (FS920, produced by Hamamatsu Photonics K.K.) using a degassed dichloromethane solution (0.083 mmol/L) at room temperature. FIG. 10 shows the measurement results. In FIG. 10, the horizontal axis represents wavelength and the vertical axes represent absorption intensity and emission intensity.

As shown in FIG. 10, the phosphorescent organometallic iridium complex [Ir(tBumpypm)$_2$(acac)] (abbreviation) according to one embodiment of the present invention has an emission peak at 511 nm, and green light emission was observed from the dichloromethane solution.

Further, bis[2-methyl-3-(6-tert-butyl-4-pyrimidinyl-κN3)pyridyl-κC4](2,4-pentanedionato-κ$^2$O, O')iridium(III) (abbreviation: [Ir(tBumpypm)$_2$(acac)]) obtained in this example was analyzed by liquid chromatography mass spectrometry (LC/MS).

The LC/MS was carried out with Acquity UPLC (produced by Waters Corporation) and Xevo G2 Tof MS (produced by Waters Corporation).

In the MS, ionization was carried out by an electrospray ionization (ESI) method. Capillary voltage and sample cone voltage were set to 3.0 kV and 30 V, respectively. Detection was performed in a positive mode. A component with m/z of 745 which underwent the separation and the ionization under the above-mentioned conditions was collided with an argon gas in a collision cell to dissociate into fragment ions. Energy (collision energy) for the collision with argon was 30 eV. A mass range for the measurement was m/z=100-1200. The detection result of the dissociated fragment ions by time-of-flight (TOF) MS are shown in FIG. 24.

Figure 24:
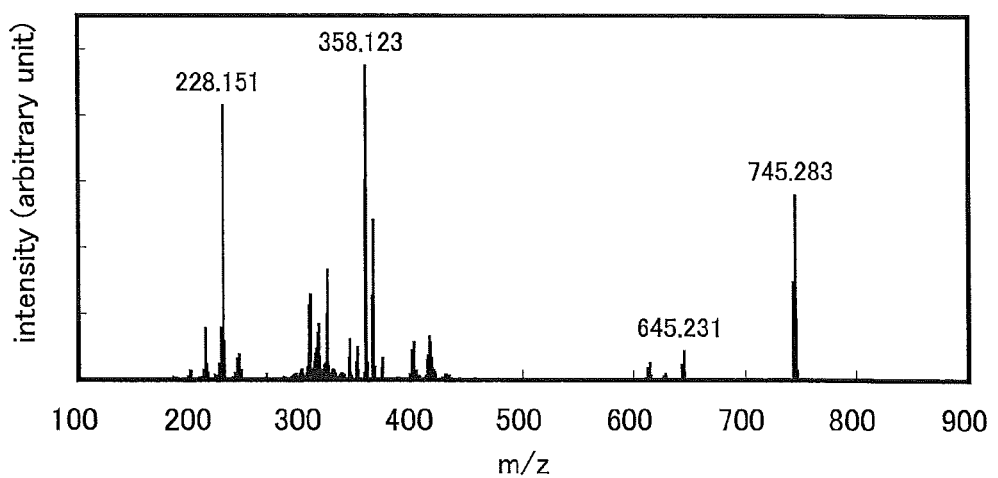
FIG. 24 shows LC/MS measurement results of the phosphorescent organometallic iridium complex represented by the structural formula (100)

The results in FIG. 24 show that product ions of the phosphorescent organometallic iridium complex [Ir(tBumpypm)$_2$(acac)] (abbreviation) represented by the structural formula (100) according to one embodiment of the present invention were detected mainly around m/z=645, around m/z=358, and around m/z=228. Note that the results in FIG. 24 shows characteristics derived from [Ir(tBumpypm)$_2$(acac)] (abbreviation) and therefore can be regarded as important data for identifying [Ir(tBumpypm)$_2$(acac)] (abbreviation) contained in the mixture.

Example 2

Synthetic Example 2

This example shows a method for synthesizing the phosphorescent organometallic iridium complex tris[2-methyl-3-(6-tert-butyl-4-pyrimidinyl-κN3)pyridyl-κC4]iridium(III) (abbreviation: [Ir(tBumpypm)$_3$]) represented by the structural formula (102) in Embodiment 1 according to one embodiment of the present invention. A structure of [Ir(tBumpypm)$_3$] is shown below.

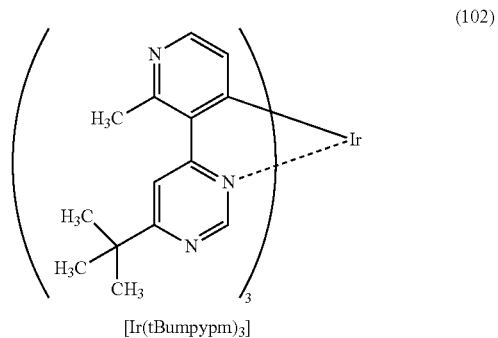

[Ir(tBumpypm)$_3$]

Step 1: Synthesis of 4-Hydroxy-6-tert-butylpyrimidine

First, 7.2 g of formamidine acetate, 7.5 g of sodium methoxide, and 70 mL of methanol were put in a 100 mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated brine, and anhydrate magnesium sulfate was added to the organic layer for drying. The obtained mixture was subjected to gravity filtration, and the filtrate was condensed to give a solid. This solid was washed with ethyl acetate to give 4-hydroxy-6-tert-butylpyrimidine (white solid, yield of 49%). A synthetic scheme of Step 1 is shown in (b-1) below.

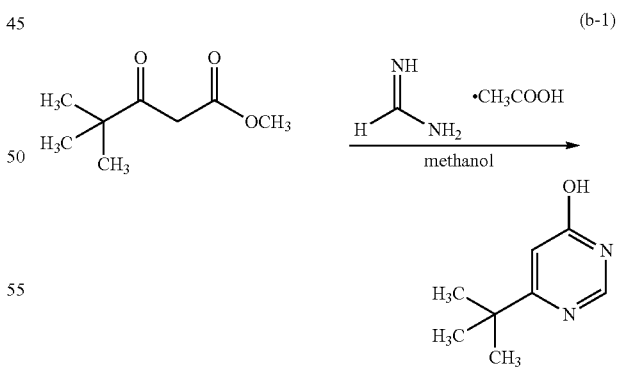

Step 2: Synthesis of 4-Chloro-6-tert-butylpyrimidine

Next, 4.7 g of 4-hydroxy-6-tert-butylpyrimidine obtained in Step 1 and 14 mL of phosphoryl chloride were put in a 50 mL three-neck flask, and the mixture was heated and refluxed for 1.5 hours. After the reflux, phosphoryl chloride was distilled off under reduced pressure. The obtained residue was dissolved in dichloromethane, and washed with water and then a saturated aqueous solution of sodium hydrogen carbonate. Anhydrate magnesium sulfate was added to the obtained organic layer for drying. This mixture was subjected to gravity filtration, and the filtrate was condensed to give a solid. This solid was purified by silica gel column chromatography. As a developing solvent, a mixed solvent of hexane and ethyl acetate in a ratio of 10:1 (v/v) was used. The obtained fraction was condensed to give 4-chloro-6-tert-butylpyrimidine (white solid, yield of 78%). A synthetic scheme of Step 2 is shown in (b-2) below.

(b-2)

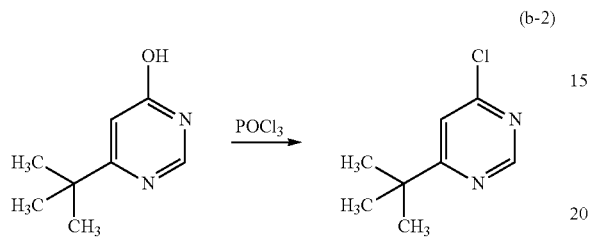

Step 3: Synthesis of 4-(2-Methylpyridin-3-yl)-6-tert-butylpyrimidine (abbreviation: HtBumpypm)

Next, 2.0 g of 4-chloro-6-tert-butylpyrimidine obtained in the above Step 2, 3.0 g of 2-methylpyridine-3-boronic acid pinacol ester, 17 mL of 1M aqueous solution of potassium acetate, 17 mL of 1M aqueous solution of sodium carbonate, and 40 mL of acetonitrile were put in a 100 mL round-bottom flask, and the air in the flask was replaced with argon. To this mixture, 0.78 g of tetrakis(triphenylphosphine)palladium(0) was added, and the mixture was irradiated with microwaves under conditions of 100° C. and 100 W for 1 hour to cause a reaction. This reaction mixture was subjected to extraction with ethyl acetate, and washing with saturated brine was performed. Anhydrous magnesium sulfate was added to the obtained solution of the extract for drying, and the resulting mixture was gravity-filtered to give a filtrate. The resulting filtrate was dissolved in a mixed solvent of ethyl acetate and hexane, and the mixture was filtered through Celite, alumina, and Celite. The resulting filtrate was purified by silica gel column chromatography. As a developing solvent, a mixed solvent of hexane and ethyl acetate in a ratio of 3:2 (v/v) was used. The obtained fractions were condensed to give an oily substance. This oily substance was dissolved in a mixed solvent of hexane and ethyl acetate, and the solution was filtered through a filter aid in which Celite, alumina, and Celite were stacked in this order. The resulting filtrate was condensed to give 4-(2-methylpyridin-3-yl)-6-tert-butylpyrimidine (abbreviation: HtBumpypm) (light-yellow oily substance, yield of 92%). A synthetic scheme of Step 3 is shown in (b-3) below.

(b-3)

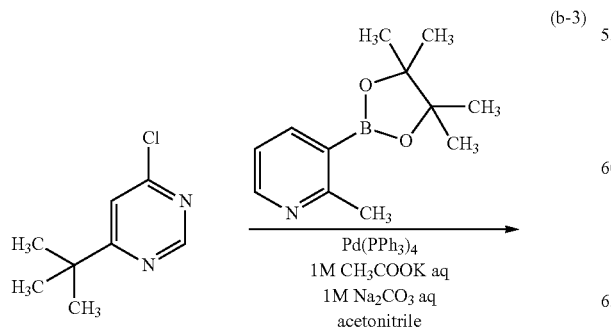

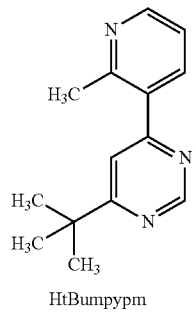

HtBumpypm

Step 4: Synthesis of Tris[2-methyl-3-(6-tert-butyl-4-pyrimidinyl-κN3)pyridyl-κC4]iridium(III) (abbreviation: [Ir(tBumpypm)₃])

Next, 3.31 g of the ligand HtBumpypm obtained in the above Step 3, and 1.42 g of tris(acetylacetonato)iridium(III) were put in a reaction container provided with a three-way cock, and the air in the reaction container was replaced with argon. After that, the mixture was heated at 250° C. for 50.5 hours to cause a reaction. The obtained residue was purified by flash column chromatography using ethyl acetate and methanol as a developing solvent in a ratio of 4:1. The solvent of the resulting fraction was distilled off to give a solid. The resulting solid was recrystallized twice from a mixed solvent of dichloromethane and hexane to give the phosphorescent organometallic iridium complex [Ir(tBumpypm)₃] according to one embodiment of the present invention (yellow-brown powder, yield of 22%). A synthetic scheme of Step 4 is shown in (b-4) below.

(b-4)

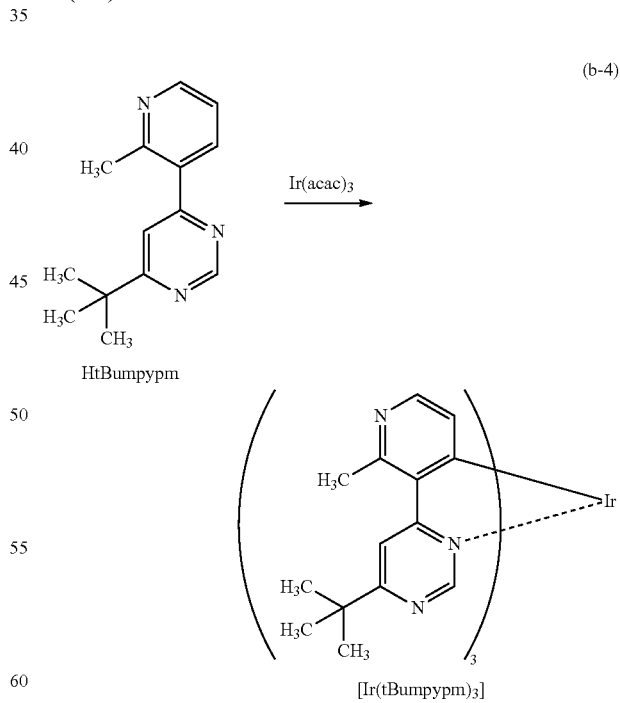

Figure 11:
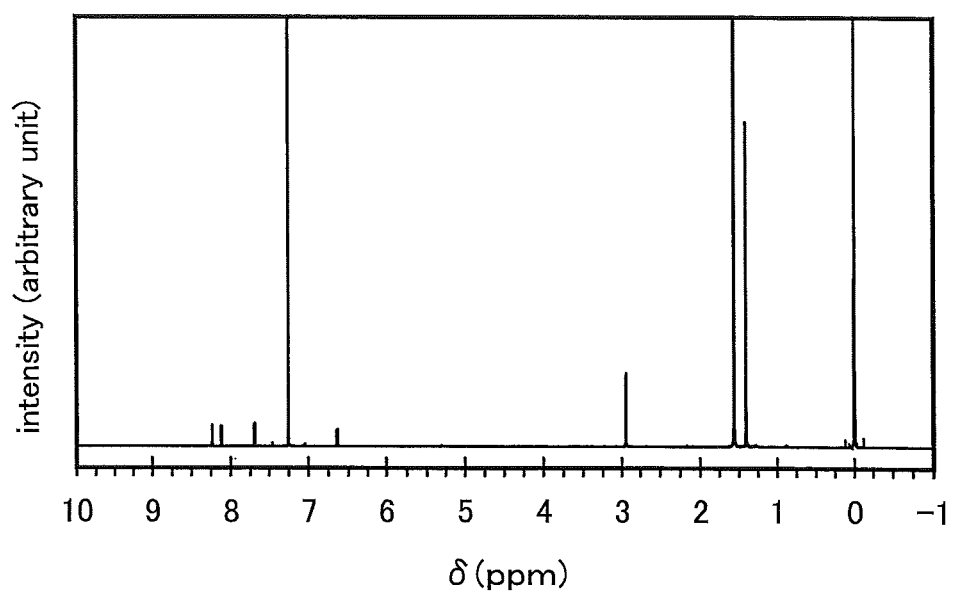
FIG. 11 shows a $^1$H-NMR chart of a phosphorescent organometallic iridium complex represented by a structural formula (102)

Results of analysis of the yellow-brown powder obtained in the above Step 4 by nuclear magnetic resonance spectrometry (¹H-NMR) are shown below. The ¹H-NMR chart is shown in FIG. 11. These results revealed that the phosphorescent organometallic iridium complex [Ir(tBumpypm)₃]

(abbreviation) represented by the structural formula (102) according to one embodiment of the present invention was obtained in Synthetic Example 2.

$^1$H-NMR. δ (CDCl$_3$): 1.41 (s, 27H), 2.94 (s, 9H), 6.64 (d, 3H), 7.70 (d, 3H), 8.12 (s, 3H), 8.24 (s, 3H).

Figure 12:
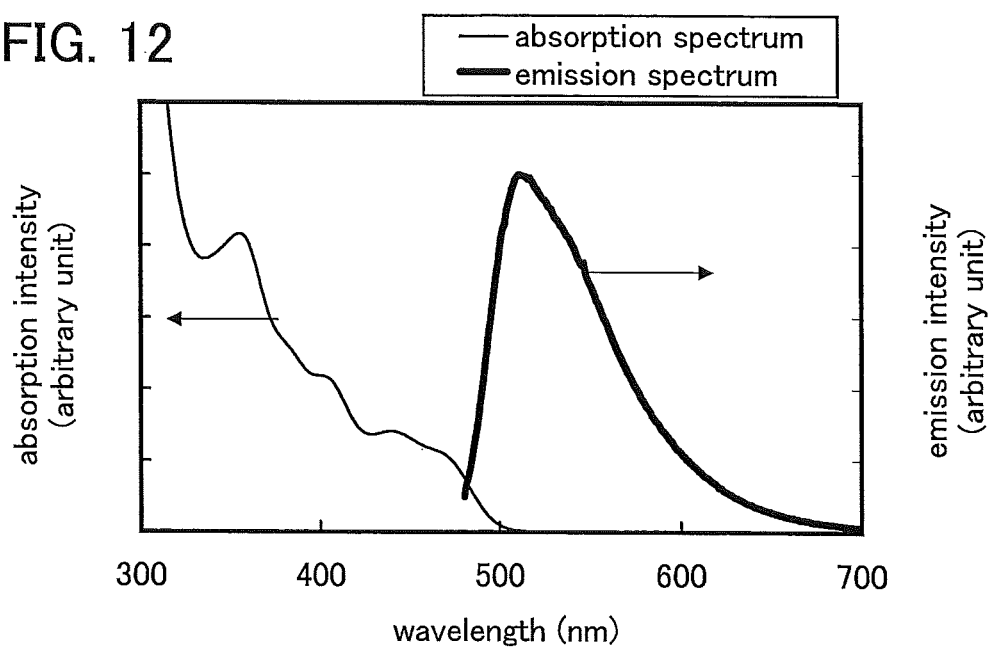
FIG. 12 shows an ultraviolet-visible absorption spectrum and an emission spectrum of the phosphorescent organometallic iridium complex represented by the structural formula (102)

Next, an analysis of [Ir(tBumpypm)$_3$] (abbreviation) was conducted by an ultraviolet-visible (UV) absorption spectrometry. The UV spectrum was measured with an ultraviolet-visible spectrophotometer (V-550, produced by JASCO Corporation) using a dichloromethane solution (0.080 mmol/L) at room temperature. Further, an emission spectrum of [Ir (tBumpypm)$_3$] (abbreviation) was measured. The emission spectrum was measured with a fluorescence spectrophotometer (FS920, produced by Hamamatsu Photonics K.K.) using a degassed dichloromethane solution (0.080 mmol/L) at room temperature. FIG. 12 shows the measurement results. In FIG. 12, the horizontal axis represents wavelength and the vertical axes represent absorption intensity and emission intensity.

As shown in FIG. 12, the phosphorescent organometallic iridium complex [Ir(tBumpypm)$_3$] (abbreviation) according to one embodiment of the present invention has an emission peak at 510 nm, and green light emission was observed from the dichloromethane solution.

Further, tris[2-methyl-3-(6-tert-butyl-4-pyrimidinyl-κN3) pyridyl-κC4]iridium(III) (abbreviation: [Ir(tBumpypm)$_3$]) obtained in this example was analyzed by liquid chromatography mass spectrometry (LC/MS).

The LC/MS was carried out with Acquity UPLC (produced by Waters Corporation) and Xevo G2 Tof MS (produced by Waters Corporation).

In the MS, ionization was carried out by an electrospray ionization (ESI) method. Capillary voltage and sample cone voltage were set to 3.0 kV and 30 V, respectively. Detection was performed in a positive mode. A component with m/z of 872 which underwent the separation and the ionization under the above-mentioned conditions was collided with an argon gas in a collision cell to dissociate into fragment ions. Energy (collision energy) for the collision with argon was 30 eV. A mass range for the measurement was m/z=100-1200. The detection result of the dissociated fragment ions by time-of-flight (TOF) MS are shown in FIG. 25.

Figure 25:
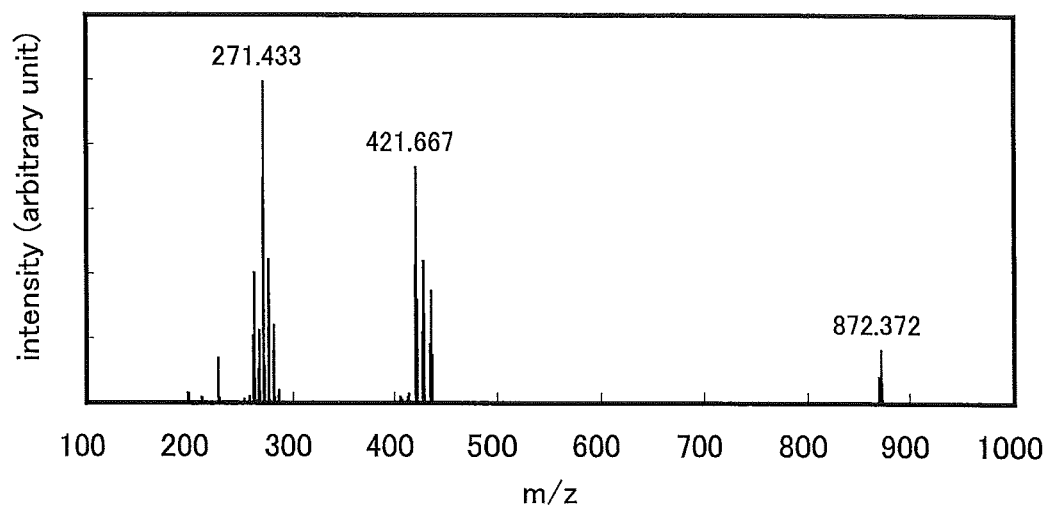
FIG. 25 shows LC/MS measurement results of the phosphorescent organometallic iridium complex represented by the structural formula (102)

The results in FIG. 25 show that product ions of the phosphorescent organometallic iridium complex [Ir (tBumpypm)$_3$] (abbreviation) represented by the structural formula (102) according to one embodiment of the present invention were detected mainly around m/z=421 and around m/z=271. Note that the results in FIG. 25 shows characteristics derived from [Ir(tBumpypm)$_3$] (abbreviation) and therefore can be regarded as important data for identifying [Ir (tBumpypm)$_3$] (abbreviation) contained in the mixture.

Example 3

Synthetic Example 3

This example shows a method for synthesizing the phosphorescent organometallic iridium complex bis{3-[6-(2-methylpyridin-3-yl)-4-pyrimidinyl-κN3]-2-methylpyridyl-κC4}(2,4-pentane dionato-κ$^2$O,O')iridium(III) (abbreviation: [Ir(dmpypm)$_2$(acac)]) represented by the structural formula (101) in Embodiment 1 according to one embodiment of the present invention. A structure of [Ir (dmpypm)$_2$(acac)] (abbreviation) is shown below.

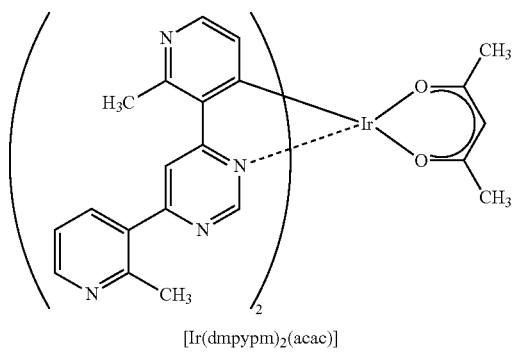

[Ir(dmpypm)$_2$(acac)]

Step 1: Synthesis of 4-Chloro-6-(2-methylpyridin-3-yl)pyrimidine

First, 3.01 g of 4,6-dichloropyrimidine, 10.9 g of 2-methylpyridine-3-boronic acid pinacol ester, 60 mL of 1M aqueous solution of potassium acetate, 60 mL of 1M aqueous solution of sodium carbonate, and 60 mL of acetonitrile were put in a 300 mL three-neck flask, and the air in the flask was replaced with argon. To this mixture, 1.40 g of tetrakis(triphenylphosphine)palladium(0) was added, and the mixture was irradiated with microwaves under conditions of 70° C. and 400 W and for 2 hours to cause a reaction. This reaction mixture was extracted with ethyl acetate, and washing with saturated brine was performed. Anhydrous magnesium sulfate was added to the obtained solution of the extract for drying, and the resulting mixture was gravity-filtered to give a filtrate. A residue obtained by condensing the filtrate was purified by flash column chromatography using ethyl acetate as a developing solvent. A solid obtained by condensing the fraction was purified by flash column chromatography using hexane and ethyl acetate in a ratio of 1:1 as a developing solvent, so that 4-chloro-6-(2-methylpyridin-3-yl)pyrimidine was obtained (a yellow white solid, yield of 24%). A synthetic scheme of Step 1 is shown in (c-1) below.

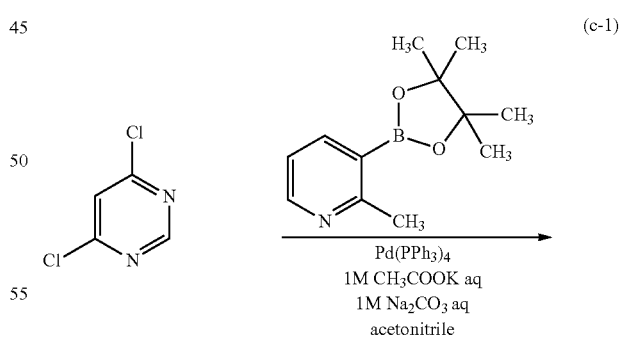

Step 2: Synthesis of 4,6-Bis(2-methylpyridin-3-yl)pyrimidine

Next, 0.99 g of 4-chloro-6-(2-methylpyridin-3-yl)pyrimidine obtained in the above Step 1, 1.34 g of 2-methylpyridine-3-boronic acid pinacol ester, 7.2 mL of 1M aqueous solution of potassium acetate, 7.2 mL of 1M aqueous solution of sodium carbonate, and 15 mL of acetonitrile were put in a 100 mL round-bottom flask, and the air in the flask was replaced with argon. To this mixture, 0.33 g of tetrakis(triphenylphosphine)palladium(0) was added, and the reaction container was heated by being irradiated with microwaves (2.45 GHz, 100 W) for 60 minutes. This reaction mixture was extracted with ethyl acetate, and washing with saturated brine was performed. Anhydrous magnesium sulfate was added to the obtained solution of the extract for drying, and the resulting mixture was gravity-filtered to give a filtrate. A residue obtained by condensing the filtrate was purified by flash column chromatography using ethyl acetate and methanol in a ratio of 4:1 as a developing solvent, so that 4,6-bis(2-methylpyridin-3-yl)pyrimidine (abbreviation: Hdmpypm) was obtained (a yellow solid, yield of 93%). A synthetic scheme of Step 2 is shown in (c-2) below.

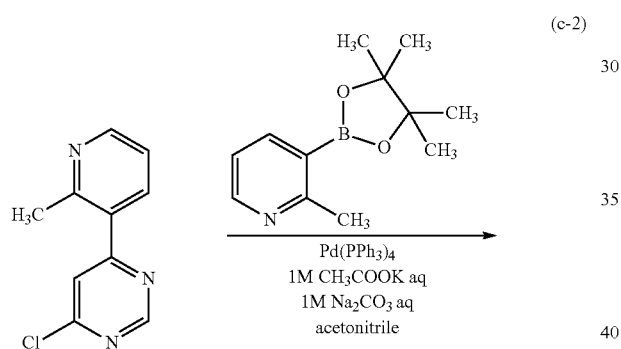

(c-2)

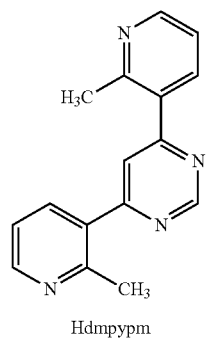

Hdmpypm

Step 3: Synthesis of Di-μ-chloro-tetrakis{3-[6-(2-methylpyridin-3-yl)-4-pyrimidinyl-κN3]-2-methylpyridyl-κC4}diiridium(III) (abbreviation: [Ir(dmpypm)$_2$Cl]$_2$)

Next, 15 mL of 2-ethoxyethanol, 5 mL of water, 1.22 g of the ligand Hdmpypm obtained in the above Step 2, and 0.66 g of iridium chloride hydrate (IrCl$_3$.H$_2$O) were put in a recovery flask equipped with a reflux pipe, and the air in the flask was replaced with argon. Then, microwave irradiation (2.45 GHz, 100 W) was performed for 1 hour to cause a reaction. The solvent was distilled off, and then the obtained residue was suction-filtered and washed, so that a dinuclear complex [Ir(dmpypm)$_2$Cl]$_2$ was obtained (a brown solid, yield of 72%). A synthetic scheme of Step 3 is shown in (c-3) below.

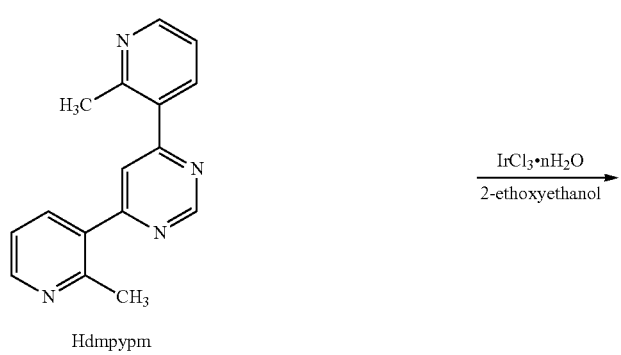

(c-3)

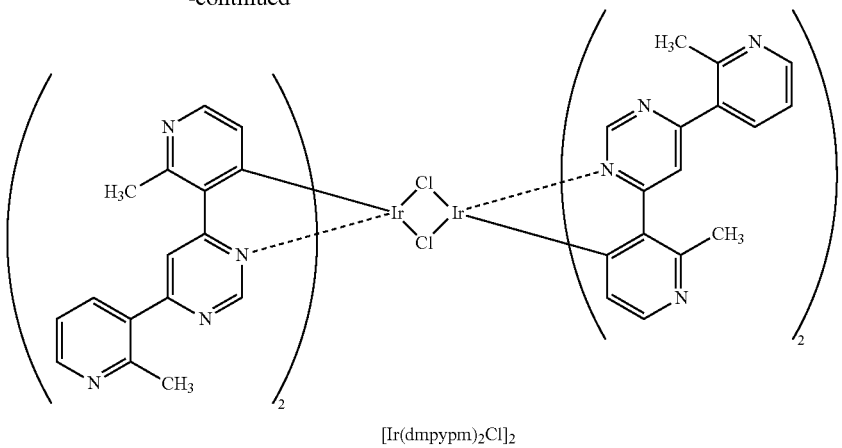

[Ir(dmpypm)₂Cl]₂

Step 4: Synthesis of Bis{3-[6-(2-methylpyridin-3-yl)-4-pyrimidinyl-κN3]-2-methylpyridyl-κC4}(2,4-pentanedionato-κ²O,O')iridium(III) (abbreviation: [Ir(dmpypm)₂(acac)])

Next, 1.18 g of the dinuclear complex [Ir(dmpypm)₂Cl]₂ obtained in the above Step 3, 0.85 g of sodium carbonate, 0.24 g of acetylacetone, and 30 mL of 2-ethoxyethanol were put in a 100 mL round-bottom flask, and the air in the flask was replaced with argon. This reaction container was irradiated with microwaves under conditions of 110° C. and 120 W for 1 hour. Further, 0.24 g of acetylacetone was added, and the reaction container was irradiated with microwaves under conditions of 110° C. and 120 W for 1 hour to cause a reaction. The solvent was distilled off, and the obtained residue was suction-filtered with ethanol. The obtained solid was washed with water and ethanol. The obtained solid was purified by flash column chromatography using ethyl acetate as a developing solvent. The fraction was condensed and the obtained solid was recrystallized from a mixed solvent of dichloromethane and hexane to give the phosphorescent organometallic iridium complex [Ir(dmpypm)₂(acac)] according to one embodiment of the present invention (yellow orange powder, yield of 11%). A synthetic scheme of Step 4 is shown in (c-4) below.

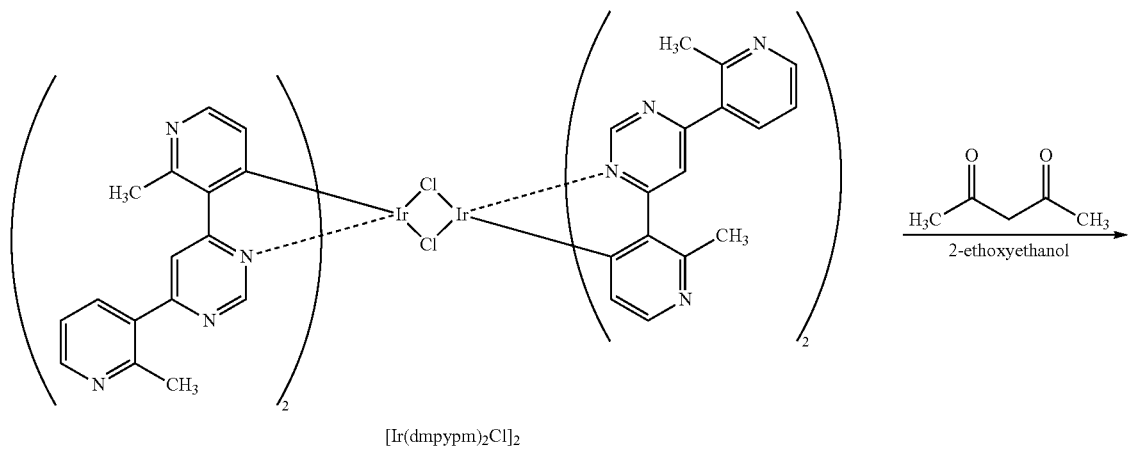

(c-4)

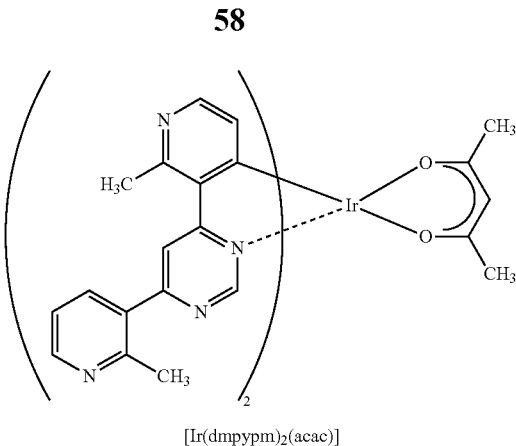

[Ir(dmpypm)₂(acac)]

Figure 13:
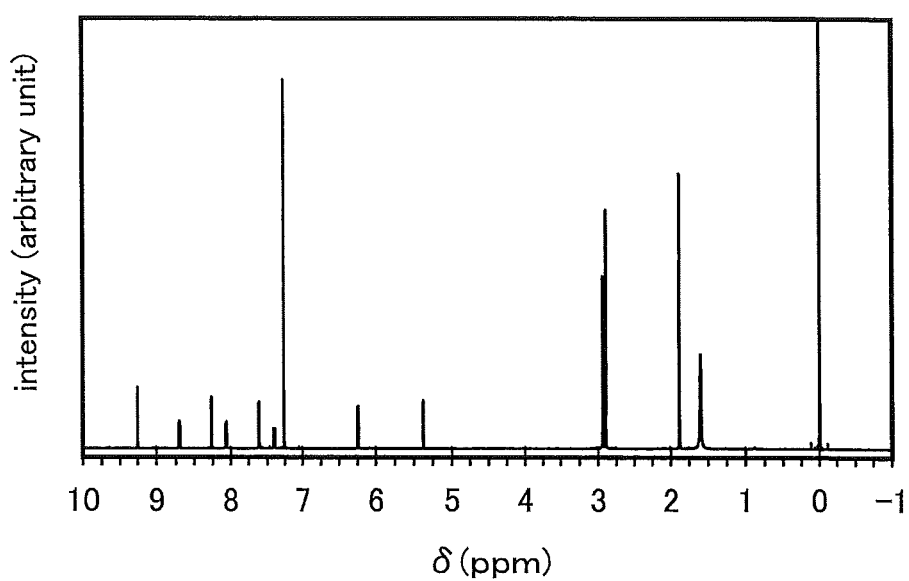
FIG. 13 shows a $^1$H-NMR chart of a phosphorescent organometallic iridium complex represented by a structural formula (101)

Results of analysis of the yellow orange powder obtained in the above Step 4 by nuclear magnetic resonance spectrometry (¹H-NMR) are shown below. The ¹H-NMR chart is shown in FIG. 13. These results revealed that the phosphorescent organometallic iridium complex [Ir(dmpypm)₂(acac)] (abbreviation) represented by the structural formula (101) according to one embodiment of the present invention was obtained in Synthetic Example 3.

¹H-NMR. δ (CDCl₃): 1.88 (s, 6H), 2.89 (s, 6H), 2.94 (s, 6H), 5.38 (s, 1H), 6.25 (d, 2H), 7.40 (dd, 2H), 7.62 (d, 2H), 8.06 (d, 2H), 8.27 (d, 2H), 8.70 (d, 2H), 9.25 (d, 2H).

Figure 14:
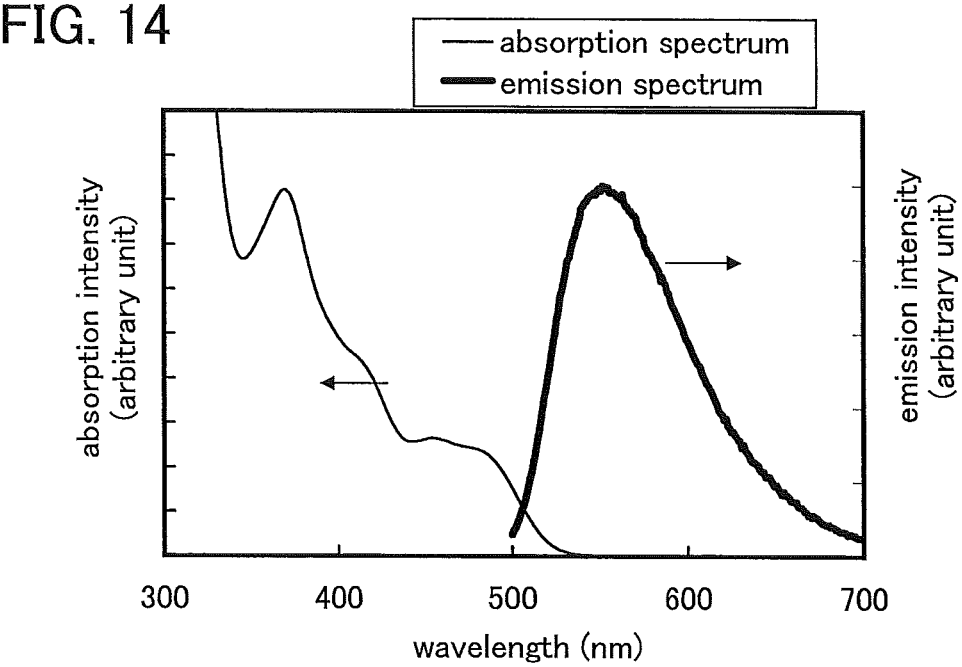
FIG. 14 shows an ultraviolet-visible absorption spectrum and an emission spectrum of the phosphorescent organometallic iridium complex represented by the structural formula (101)

Next, an analysis of [Ir(dmpypm)₂(acac)] (abbreviation) was conducted by an ultraviolet-visible (UV) absorption spectrometry. The UV spectrum was measured with an ultraviolet-visible spectrophotometer (V-550, produced by JASCO Corporation) using a dichloromethane solution (0.086 mmol/L) at room temperature. Further, an emission spectrum of [Ir(dmpypm)₂(acac)] (abbreviation) was measured. The emission spectrum was measured with a fluorescence spectrophotometer (FS920, produced by Hamamatsu Photonics K.K.) using a degassed dichloromethane solution (0.086 mmol/L) at room temperature. FIG. 14 shows the measurement results. In FIG. 14, the horizontal axis represents wavelength and the vertical axes represent absorption intensity and emission intensity.

As shown in FIG. 14, the phosphorescent organometallic iridium complex [Ir(dmpypm)₂(acac)] (abbreviation) according to one embodiment of the present invention has an emission peak at 551 nm, and yellow light emission was observed from the dichloromethane solution.

Further, bis{3-[6-(2-methylpyridin-3-yl)-4-pyrimidinyl-κN3]-2-methylpyridyl-κC4}(2,4-pentane dionato-κ²O,O') iridium(III) (abbreviation: [Ir(dmpypm)₂(acac)]) obtained in this example was analyzed by liquid chromatography mass spectrometry (LC/MS).

The LC/MS was carried out with Acquity UPLC (produced by Waters Corporation) and Xevo G2 Tof MS (produced by Waters Corporation).

Figure 26:
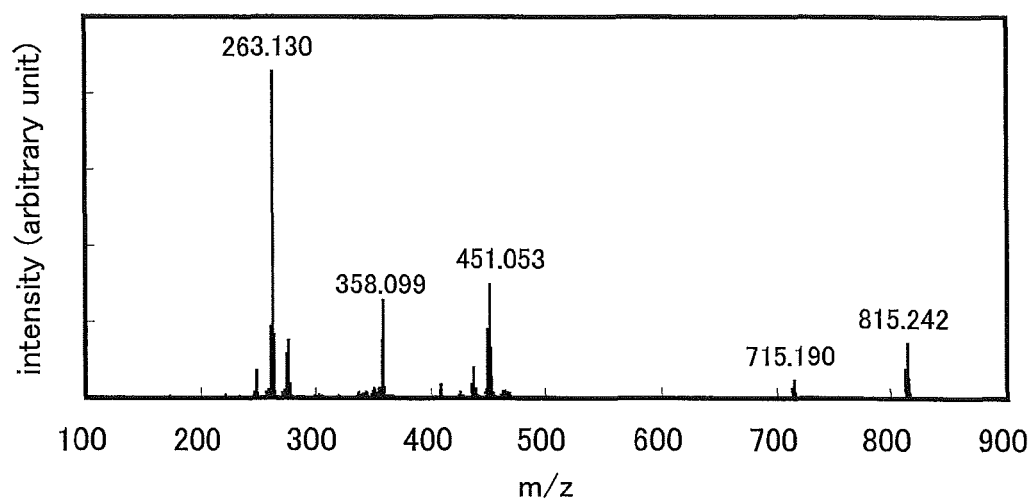
FIG. 26 shows LC/MS measurement results of the phosphorescent organometallic iridium complex represented by the structural formula (101)

In the MS, ionization was carried out by an electrospray ionization (ESI) method. Capillary voltage and sample cone voltage were set to 3.0 kV and 30 V, respectively. Detection was performed in a positive mode. A component with m/z of 814 which underwent the ionization under the above-mentioned conditions was collided with an argon gas in a collision cell to dissociate into product ions. Energy (collision energy) for the collision with argon was 30 eV. A mass range for the measurement was m/z=100-1200. The detection result of the dissociated fragment ions by time-of-flight (TOF) MS are shown in FIG. 26.

The results in FIG. 24 show that product ions of the phosphorescent organometallic iridium complex [Ir(dmpypm)₂(acac)] (abbreviation) represented by the structural formula (101) according to one embodiment of the present invention were detected mainly around m/z=715, around m/z=451, around m/z=358, and around m/z=263. Note that the results in FIG. 26 shows characteristics derived from [Ir(dmpypm)₂(acac)] (abbreviation) and therefore can be regarded as important data for identifying [Ir(dmpypm)₂(acac)] (abbreviation) contained in the mixture.

Example 4

Figure 15:
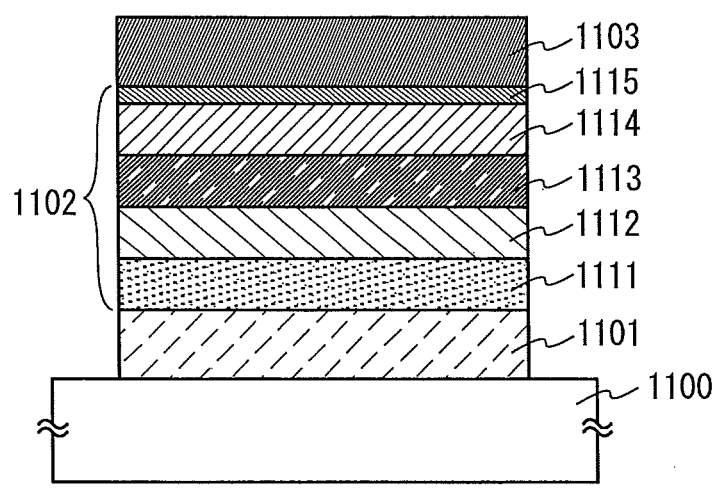
FIG. 15 illustrates a light-emitting element.

In this example, a light-emitting element 1 in which the phosphorescent organometallic iridium complex bis[2-methyl-3-(6-tert-butyl-4-pyrimidinyl-κN3)pyridyl-κC4](2,4-pentanedionato-κ²O, O')iridium(III) (abbreviation: [Ir(tBumpypm)₂(acac)]) (the structural formula (100)) was used for a light-emitting layer will be described with reference to FIG. 15. Further, as a comparative element, a comparative light-emitting element 1 was also fabricated in which a phosphorescent organometallic iridium complex different from that in the light-emitting element 1 was used for a light-emitting layer. Chemical formulae of materials used in this example are shown below.

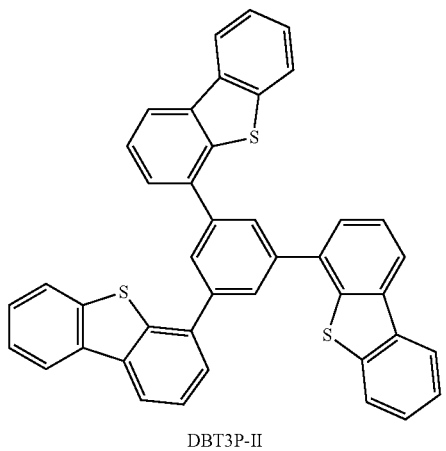

DBT3P-II

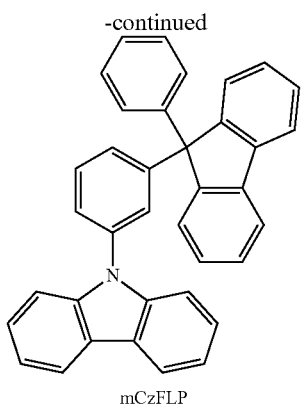

mCzFLP

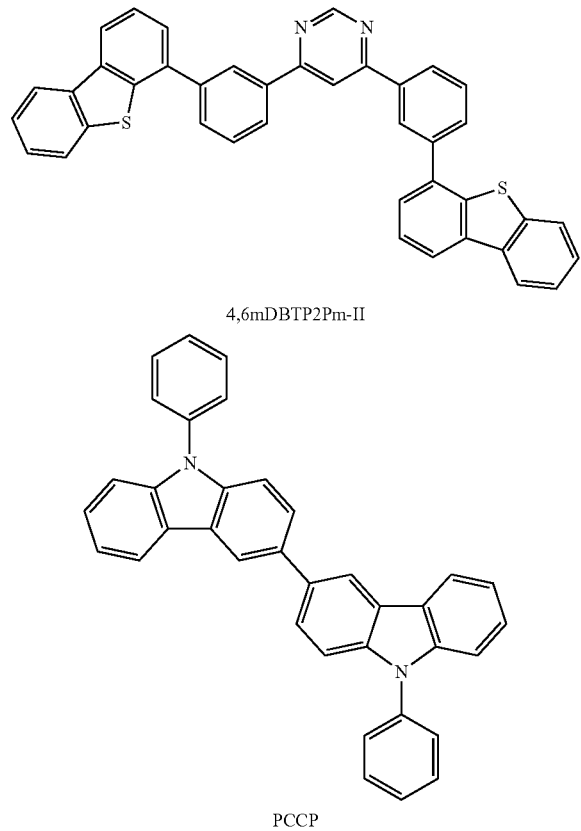

4,6mDBTP2Pm-II

PCCP

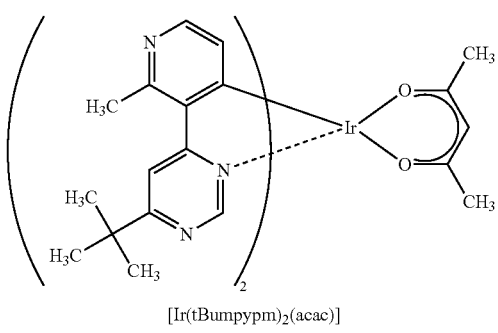

[Ir(tBumpypm)₂(acac)]

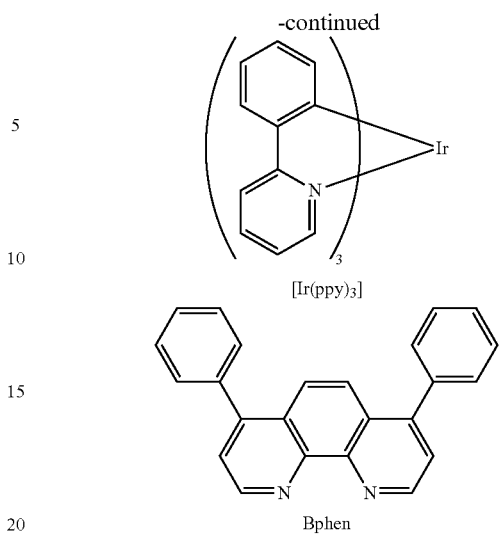

[Ir(ppy)₃]

Bphen (Fabrication of Light-Emitting Element 1 and Comparative Light-Emitting Element 1)

First, indium tin oxide containing silicon oxide (ITSO) was deposited over a glass substrate 1100 by a sputtering method, so that a first electrode 1101 which serves as an anode was formed. The thickness was 110 nm and the electrode area was 2 mm×2 mm.

Next, as pretreatment for forming the light-emitting element over the substrate 1100, the surface of the substrate was washed, baked at 200° C. for 1 hour, and subjected to UV ozone treatment for 370 seconds.

After that, the substrate 1100 was transferred into a vacuum evaporation apparatus where the pressure was reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100, over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of 4:2 (=DBT3P-II (abbreviation):molybdenum oxide), so that the hole-injection layer 1111 was formed over the first electrode 1101. The thickness of the hole-injection layer 1111 was 40 nm. Note that a co-evaporation method is an evaporation method in which a plurality of different substances is concurrently vaporized from respective different evaporation sources.

Next, 9-[3-(9-phenyl-9H-fluoren-9-yl)phenyl]-9H-carbazole (abbreviation: mCzFLP) was evaporated to a thickness of 20 nm, so that the hole-transport layer 1112 was formed.

Next, the light-emitting layer 1113 was formed over the hole-transport layer 1112. In the case of the light-emitting element 1, the light-emitting layer 1113 was formed by co-evaporation of 4,6-bis[3-(4-dibenzothienyl)phenyl]pyrimidine (abbreviation: 4,6mDBTP2Pm-II), 9-phenyl-9H-3-(9-phenyl-9H-carbazol-3-yl)carbazole (abbreviation: PCCP), and bis[2-methyl-3-(6-tert-butyl-4-pyrimidinyl-κN3)pyridyl-κC](2,4-pentanedionato-κ²O,O')iridium(III) (abbreviation: [Ir(tBumpypm)₂(acac)]) with a mass ratio of 0.8:0.2:0.025 (=4,6mDBTP2Pm-II (abbreviation):PCCP (abbreviation):[Ir(tBumpypm)$_2$(acac)] (abbreviation)) to a thickness of 40 nm. In the case of the comparative light-emitting element 1, using tris(2-phenylpyridinato)iridium (III) (abbreviation: [Ir(ppy)$_3$]) instead of [Ir(tBumpypm)$_2$(acac)] (abbreviation), the light-emitting layer 1113 was formed by co-evaporation of 4,6mDBTP2Pm-II (abbreviation), PCCP (abbreviation), and [Ir(ppy)$_3$] (abbreviation) with a mass ratio of 0.8:0.2:0.05 (=4,6mDBTP2Pm-II (abbreviation):PCCP (abbreviation): [Ir(ppy)$_3$] (abbreviation)) to a thickness of 40 nm Then, 4,6mDBTP2Pm-II (abbreviation) was evaporated to a thickness of 10 nm over the light-emitting layer 1113 and bathophenanthroline (abbreviation: Bphen) was evaporated to a thickness of 20 nm, so that the electron-transport layer 1114 was formed. Furthermore, lithium fluoride was evaporated to a thickness of 1 nm over the electron-transport layer 1114, so that the electron-injection layer 1115 was formed.

Finally, aluminum was evaporated to a thickness of 200 nm over the electron-injection layer 1115 to form a second electrode 1103 serving as a cathode; thus, the light-emitting element 1 and the comparative light-emitting element 1 were obtained. Note that, in the above evaporation process, evaporation was all performed by a resistance heating method.

Figure 16:
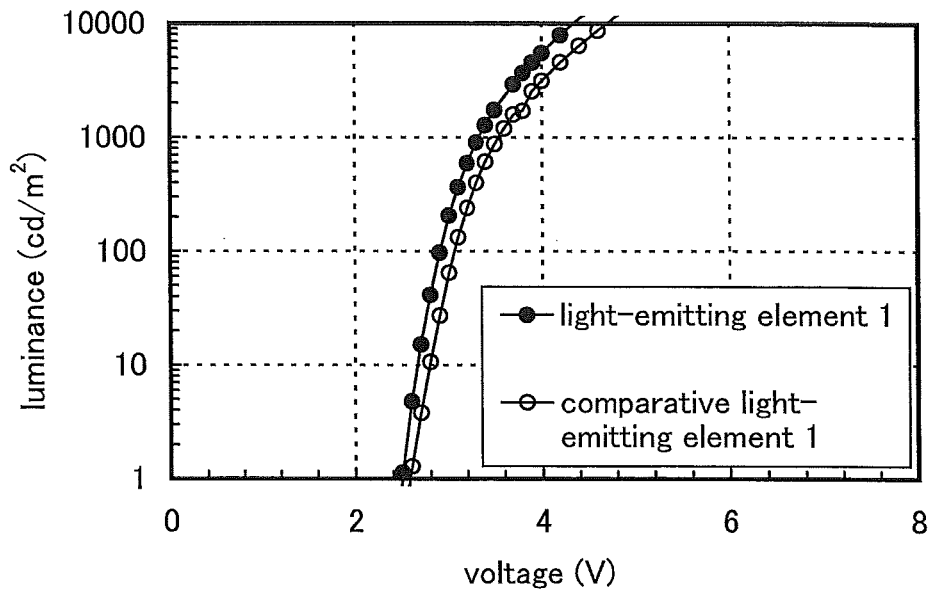
FIG. 16 shows voltage-luminance characteristics of a light-emitting element 1 and a comparative light-emitting element 1.
Figure 17:
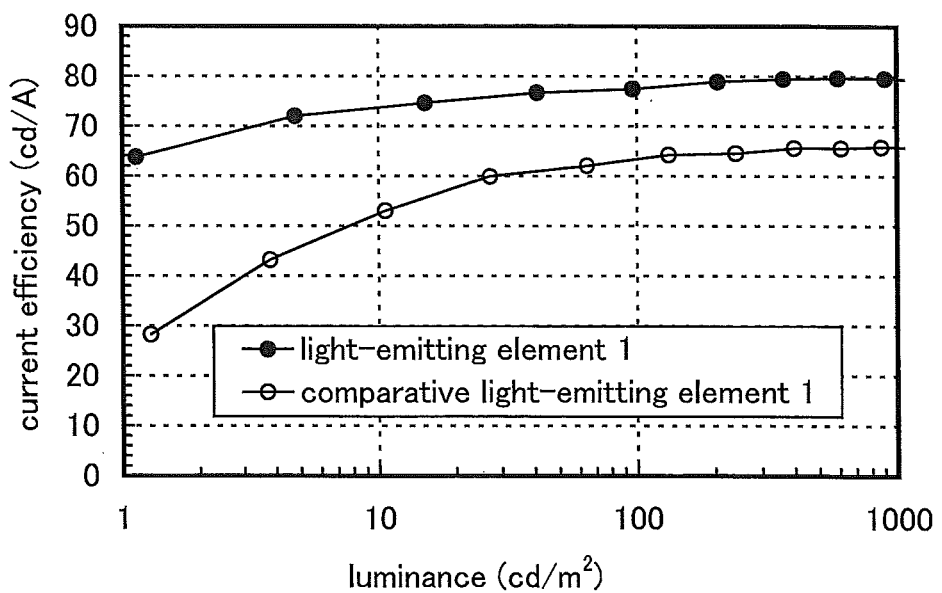
FIG. 17 shows luminance-current efficiency characteristics of the light-emitting element 1 and the comparative light-emitting element 1.
Figure 18:
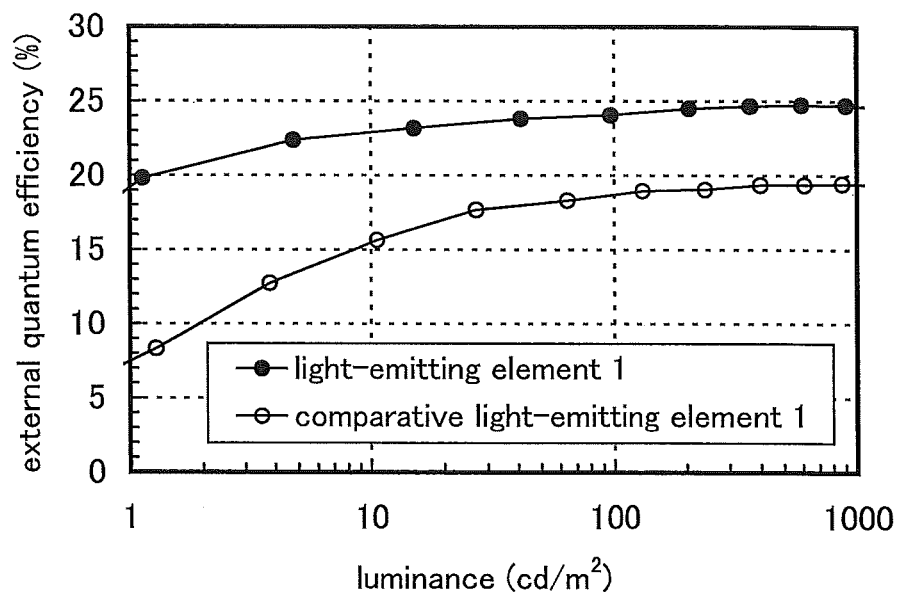
FIG. 18 shows luminance-external quantum efficiency characteristics of the light-emitting element 1 and the comparative light-emitting element 1.

Element structures of the light-emitting element 1 and the comparative light-emitting element 1 obtained as described above are shown in Table 1.

element 1. In FIG. 16, the vertical axis represents luminance (cd/m$^2$) and the horizontal axis represents voltage (V). Further, FIG. 17 shows luminance-current efficiency characteristics of the light-emitting element 1 and the comparative light-emitting element 1. In FIG. 17, the vertical axis represents current efficiency (cd/A) and the horizontal axis represents luminance (cd/m$^2$). Further, FIG. 18 shows luminance-external quantum efficiency characteristics of the light-emitting element 1 and the comparative light-emitting element 1. In FIG. 18, the vertical axis represents external quantum efficiency (%) and the horizontal axis represents luminance (cd/m$^2$).

From FIG. 18, it is found that the light-emitting element 1 in which the phosphorescent organometallic iridium complex [Ir(tBumpypm)$_2$(acac)] (abbreviation) according to one embodiment of the present invention was used in part of the light-emitting layer has higher efficiency than the comparative light-emitting element 1 in which [Ir(ppy)$_3$] (abbreviation) was used in part of the light-emitting layer. In addition, Table 2 below shows initial values of main characteristics of the light-emitting element 1 and the comparative light-emitting element 1 at a luminance of about 900 cd/m$^2$.

TABLE 1

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO (110 nm) | * | mCzFLP (20 nm) | ** | 4,6 mDBTP2Pm-II (10 nm) | Bphen (20 nm) | LiF (1 rim) | Al (200 nm) |
| Comparative Light-emitting Element 1 | ITSO (110 nm) | * | mCzFLP (20 nm) | *** | 4,6 mDBTP2Pm-II (10 nm) | Bphen (20 nm) | LiF (1 nm) | Al (200 nm) |

* DBT3P-II:MoOx (4:2, 40 nm)
** 4,6 mDBTP2Pm-II:PCCP:[Ir(tBum pypm)$_2$(acac)] (0.8:0.2:0.025, 40 nm)
*** 4,6 mDBTP2Pm-II:PCCP:[Ir(ppy)$_3$] (0.8:0.2:0.05, 40 nm)

Further, after fabrication, each of the light-emitting element 1 and the comparative light-emitting element 1 was sealed in a glove box containing a nitrogen atmosphere so as not to be exposed to the air (specifically, a sealant was applied onto an outer edge of the element and heat treatment was performed at 80° C. for 1 hour at the time of sealing).

TABLE 2

| | Voltge (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 1 | 3.3 | 0.045 | 1.1 | (0.29, 0.60) | 900 | 80 | 76 | 25 |
| Comparative Light-emitting Element 1 | 3.5 | 0.053 | 1.3 | (0.34, 0.60) | 870 | 66 | 59 | 19 |

(Operation Characteristics of Light-Emitting Element 1 and Comparative Light-Emitting Element 1)

Operation characteristics of the fabricated light-emitting element 1 and comparative light-emitting element 1 were measured. Note that the measurement was carried out at room temperature (in an atmosphere kept at 25° C.).

FIG. 16 shows voltage-luminance characteristics of the light-emitting element 1 and the comparative light-emitting From the above results, it is found that the light-emitting element 1 fabricated in this example has higher external quantum efficiency (higher emission efficiency) than the comparative light-emitting element 1. Note that from the chromaticity, it is found that the light-emitting element 1 emits green light.

Figure 19:
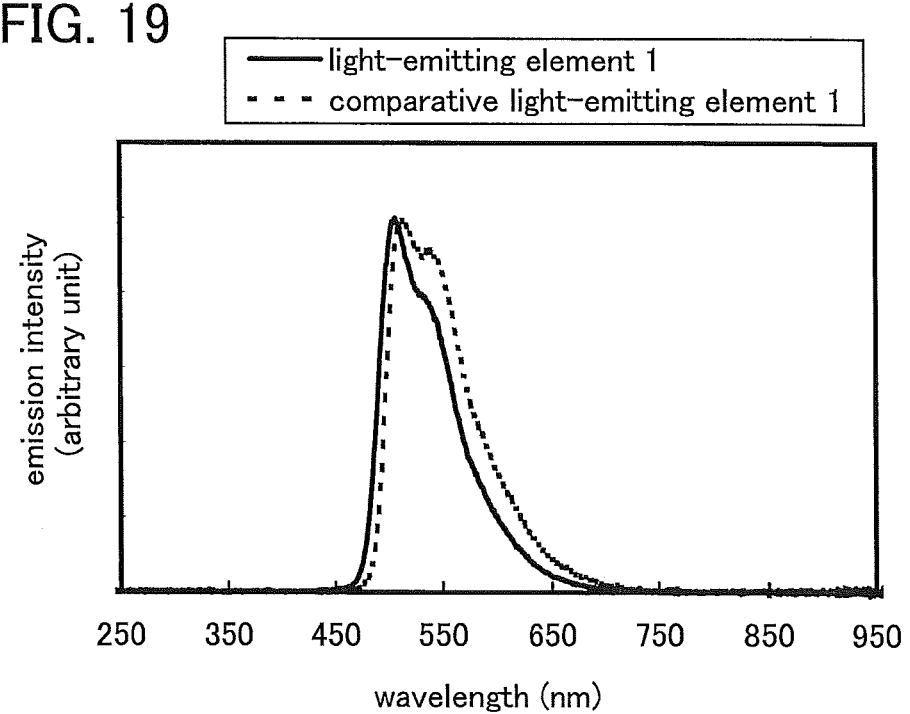
FIG. 19 shows emission spectra of the light-emitting element 1 and the comparative light-emitting element 1.

FIG. 19 shows emission spectra of the light-emitting element 1 and the comparative light-emitting element 1 when a current at a current density of 0.1 mA/cm$^2$ was supplied thereto. As shown in FIG. 19, the emission spectrum of the light-emitting element 1 has a peak around 510 nm and it is indicated that the peak is derived from emission of the phosphorescent organometallic iridium complex [Ir(tBumpypm)$_2$(acac)] (abbreviation). On the other hand, the emission spectrum of the comparative light-emitting element 1 has a peak around 516 nm and it is suggested that the peak is derived from emission of the phosphorescent organometallic iridium complex [Ir(ppy)$_3$] (abbreviation).

Example 5

In this example, a light-emitting element 2 in which the phosphorescent organometallic iridium complex tris[2-methyl-3-(6-tert-butyl-4-pyrimidinyl-κN3)pyridyl-κC]iridium (III) (abbreviation: [Ir(tBumpypm)$_3$]) (the structural formula (102)) was used for a light-emitting layer will be described. Further, a comparative light-emitting element 2 in which a phosphorescent organometallic iridium complex different from that in the light-emitting element 2 was used for a light-emitting layer will be described. Note that in the description of the light-emitting element 2 and the comparative light-emitting element 2 in this example, FIG. 15 which is used in the description of the light-emitting element 1 and the comparative light-emitting element 1 in Example 4 is to be referred to. Chemical formulae of materials used in this example are shown below.

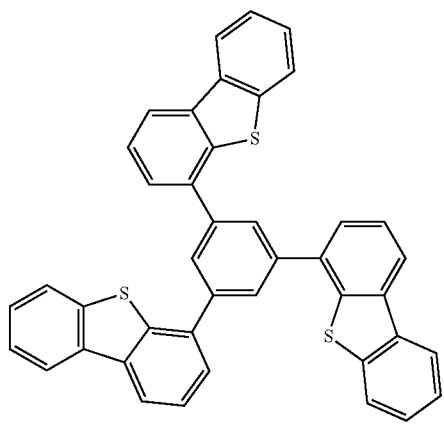

DBT3P-II

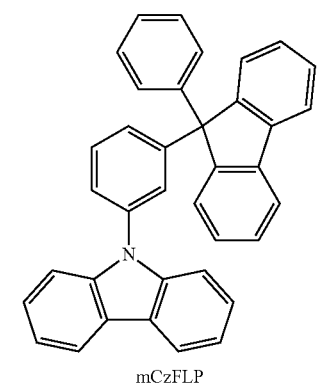 [SMILES: c1ccc(C2(c3cccc(-n4c5ccccc5c5ccccc54)c3)c3ccccc3-c3ccccc32)cc1]

mCzFLP

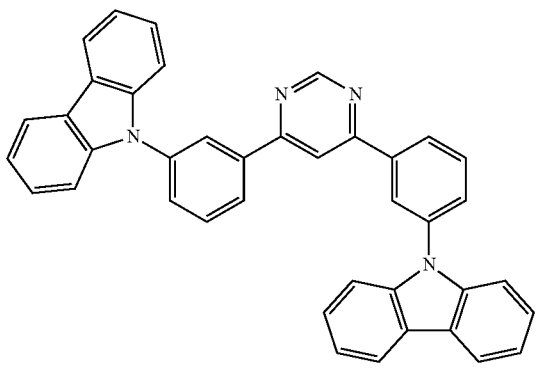

4,6mCzP2Pm

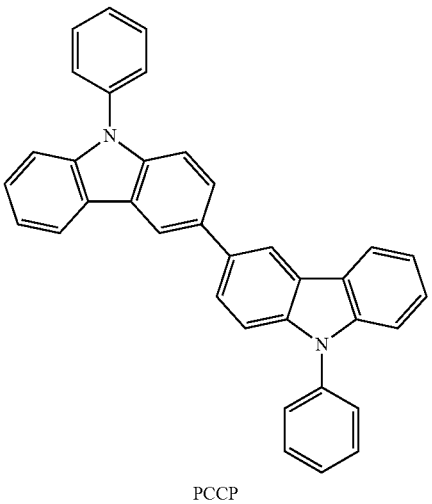

PCCP

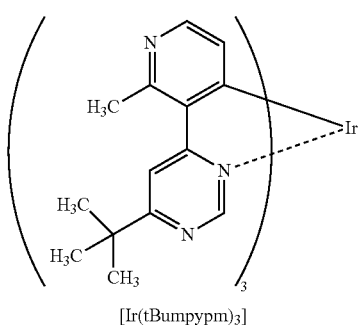

[Ir(tBumpypm)$_3$]

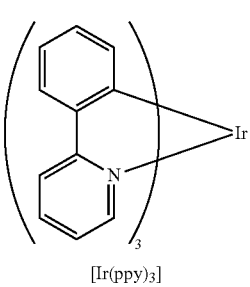

[Ir(ppy)$_3$]

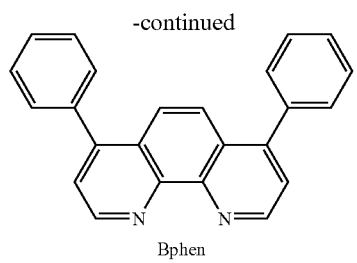

Bphen (Fabrication of Light-Emitting Element 2 and Comparative Light-Emitting Element 2)

First, indium tin oxide containing silicon oxide (ITSO) was deposited over the glass substrate 1100 by a sputtering method, so that the first electrode 1101 which serves as an anode was formed. The thickness was 110 nm and the electrode area was 2 mm×2 mm.

Next, as pretreatment for forming the light-emitting element over the substrate 1100, the surface of the substrate was washed, baked at 200° C. for 1 hour, and subjected to UV ozone treatment for 370 seconds.

After that, the substrate 1100 was transferred into a vacuum evaporation apparatus where the pressure was reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of 4:2 (=DBT3P-II (abbreviation):molybdenum oxide), so that the hole-injection layer 1111 was formed over the first electrode 1101. The thickness of the hole-injection layer 1111 was 40 nm. Note that a co-evaporation method is an evaporation method in which a plurality of different substances is concurrently vaporized from respective different evaporation sources.

Next, 9-[3-(9-phenyl-9H-fluoren-9-yl)phenyl]-9H-carbazole (abbreviation: mCzFLP) was evaporated to a thickness of 20 nm, so that the hole-transport layer 1112 was formed.

Next, the light-emitting layer 1113 was formed over the hole-transport layer 1112. In the case of the light-emitting element 2, the light-emitting layer 1113 having a stacked structure was formed in the following manner. First, 4,6-bis [3-(9H-carbazol-9-yl)phenyl]pyrimidine (abbreviation: 4,6mCzP2Pm), 9-phenyl-9H-3-(9-phenyl-9H-carbazol-3-yl) carbazole (abbreviation: PCCP), and tris[2-methyl-3-(6-tert-butyl-4-pyrimidinyl-κN3)pyridyl-κC]iridium(III) (abbreviation: [Ir(tBumpypm)$_3$]) were co-evaporated with a mass ratio of 0.5:0.5:0.05 (=4,6mCzP2Pm (abbreviation):PCCP (abbreviation):[Ir(tBumpypm)$_3$] (abbreviation)) to a thickness of 20 nm, and then 4,6mCzP2Pm (abbreviation), PCCP (abbreviation), and [Ir(tBumpypm)$_3$] (abbreviation) were co-evaporated with a mass ratio of 0.8:0.2:0.05 (=4,6mCzP2Pm (abbreviation):PCCP (abbreviation): [Ir(tBumpypm)$_3$] (abbreviation)) to a thickness of 20 nm. In the case of the comparative light-emitting element 2, using tris(2-phenylpyridinato)iridium(III) (abbreviation: [Ir(ppy)$_3$]) instead of [Ir(tBumpypm)$_3$] (abbreviation), the light-emitting layer 1113 was formed by co-evaporation of 4,6mCzP2Pm (abbreviation), PCCP (abbreviation), and [Ir(ppy)$_3$] (abbreviation) with a mass ratio of 0.8:0.2:0.05 (=4,6mCzP2Pm (abbreviation):PCCP (abbreviation): [Ir(ppy)$_3$] (abbreviation)) to a thickness of 40 nm.

Then, 4,6mCzP2Pm (abbreviation) was evaporated to a thickness of 10 nm over the light-emitting layer 1113 and bathophenanthroline (abbreviation: Bphen) was evaporated to a thickness of 20 nm, so that the electron-transport layer 1114 was formed. Furthermore, lithium fluoride was evaporated to a thickness of 1 nm over the electron-transport layer 1114, so that the electron-injection layer 1115 was formed.

Finally, aluminum was evaporated to a thickness of 200 nm over the electron-injection layer 1115 to form the second electrode 1103 serving as a cathode; thus, the light-emitting element 2 and the comparative light-emitting element 2 were obtained. Note that, in the above evaporation process, evaporation was all performed by a resistance heating method.

Element structures of the light-emitting element 2 and the comparative light-emitting element 2 obtained as described above are shown in Table 3.

TABLE 3

| | First Electrode | Hole-injection Layer | Hole-transport Layer | Light-emitting Layer | Electron-transport Layer | | Electron-injection Layer | Second Electrode |
|---|---|---|---|---|---|---|---|---|
| Light-emitting Element 2 | ITSO (110 nm) | * | mCzFLP (20 nm) | ** | 4,6 mCzP2Pm (10 nm) | Bphen (20 nm) | LiF (1 nm) | Al (200 nm) |
| Comparative Light-emitting Element 2 | ITSO (110 nm) | * | mCzFLP (20 nm) | *** | 4,6 mCzP2Pm (10 nm) | Bphen (20 nm) | LiF (1 nm) | Al (200 nm) |

* DBT3P-II:MoOx (4:2, 40 nm)
** 4,6 mCzP2Pm:PCCP:[Ir(tBum pypm)$_3$] (0.5:0.5:0.05 20 nm\0.8:0.2 :0.05, 20 nm)
*** 4,6 mCzP2Pm:PCCP:[Ir(ppy)$_3$] (0.8:0.2:0.05, 40 nm)

Further, after fabrication, each of the light-emitting element 2 and the comparative light-emitting element 2 was sealed in a glove box containing a nitrogen atmosphere so as not to be exposed to the air (specifically, a sealant was applied onto an outer edge of the element and heat treatment was performed at 80° C. for 1 hour at the time of sealing).

(Operation Characteristics of Light-Emitting Element 2 and Comparative Light-Emitting Element 2)

Operation characteristics of the fabricated light-emitting element 2 and comparative light-emitting element 2 were measured. Note that the measurement was carried out at room temperature (in an atmosphere kept at 25° C.).

Figure 20:
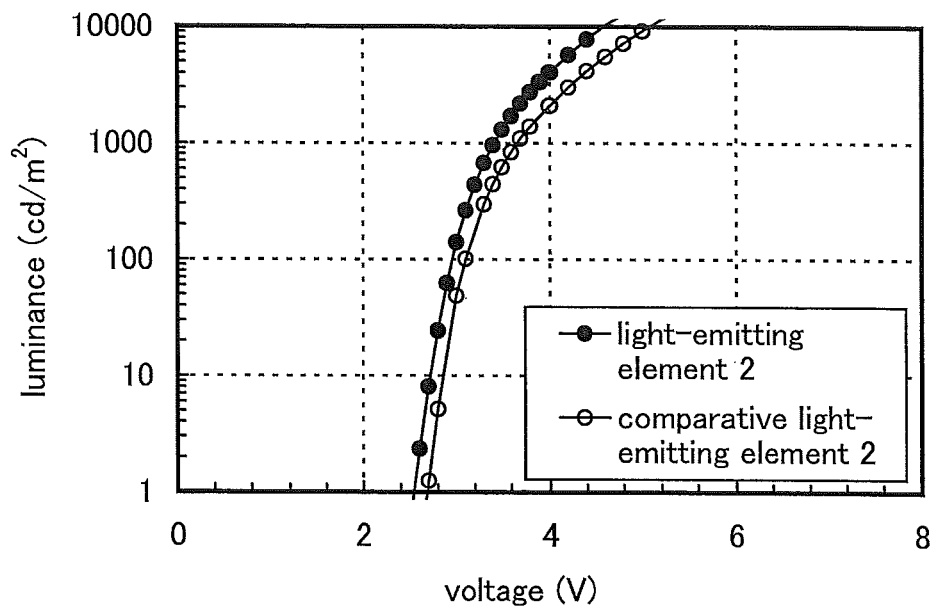
FIG. 20 shows voltage-luminance characteristics of a light-emitting element 2 and a comparative light-emitting element 2.
Figure 21:
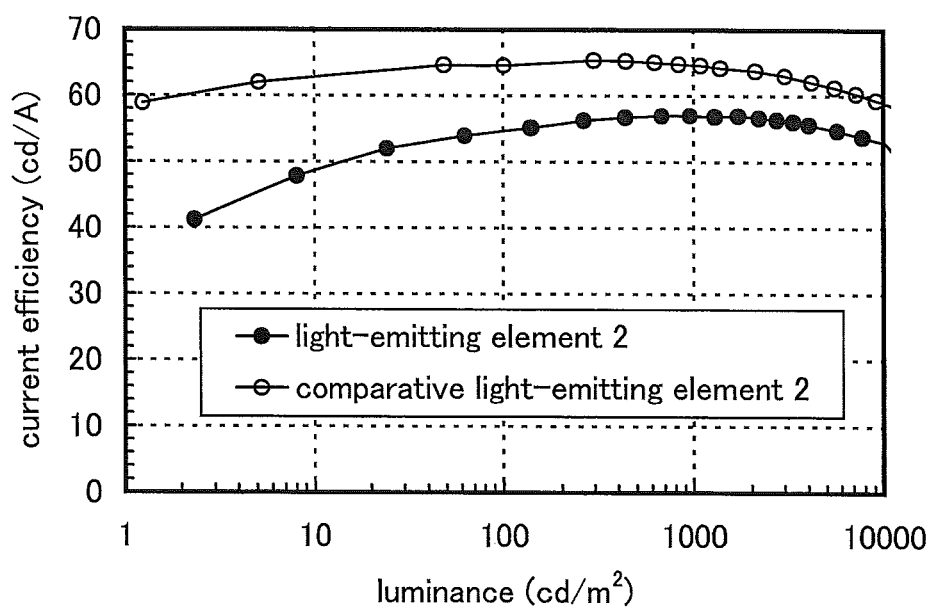
FIG. 21 shows luminance-current efficiency characteristics of the light-emitting element 2 and the comparative light-emitting element 2.
Figure 22:
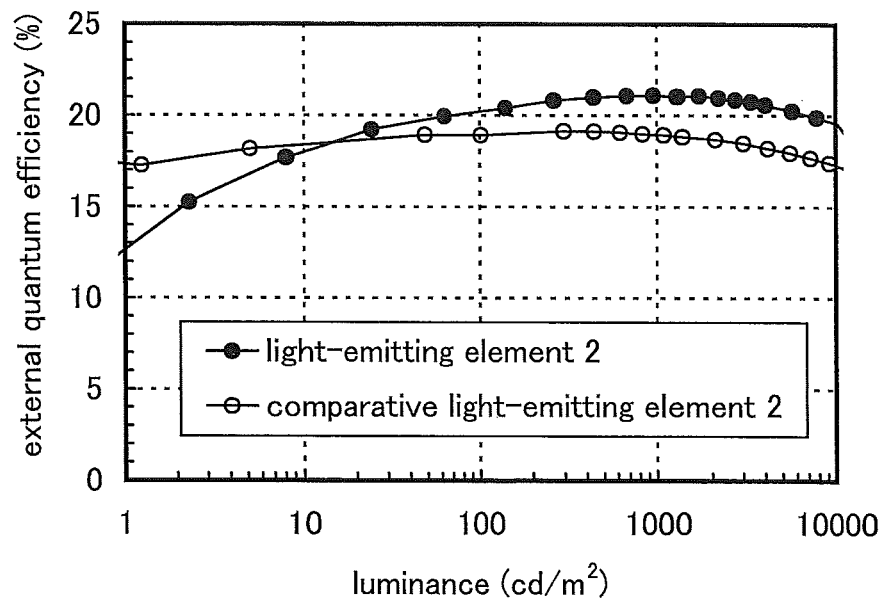
FIG. 22 shows luminance-external quantum efficiency characteristics of the light-emitting element 2 and the comparative light-emitting element 2.

FIG. 20 shows voltage-luminance characteristics of the light-emitting element 2 and the comparative light-emitting element 2. In FIG. 20, the vertical axis represents luminance (cd/m$^2$) and the horizontal axis represents voltage (V). Further, FIG. 21 shows luminance-current efficiency characteristics of the light-emitting element 2 and the comparative light-emitting element 2. In FIG. 21, the vertical axis represents current efficiency (cd/A) and the horizontal axis represents luminance (cd/m$^2$). Further, FIG. 22 shows luminance-external quantum efficiency characteristics of the light-emitting element 2 and the comparative light-emitting element 2. In FIG. 22, the vertical axis represents external quantum efficiency (%) and the horizontal axis represents luminance (cd/m$^2$).

From FIG. 22, it is found that the light-emitting element 2 in which the phosphorescent organometallic iridium complex [Ir(tBumpypm)$_3$] (abbreviation) according to one embodiment of the present invention was used in part of the light-emitting layer has higher efficiency than the comparative light-emitting element 2 in which [Ir(ppy)$_3$] (abbreviation) was used in part of the light-emitting layer. In addition, Table 4 below shows initial values of main characteristics of the light-emitting element 2 and the comparative light-emitting element 2 at a luminance of about 1000 cd/m$^2$.

Synthetic Method of 9-[3-(9-Phenyl-9H-fluoren-9-yl)phenyl]-9H-carbazole (abbreviation: mCzFLP)

A structure of mCzFLP (abbreviation) is shown below.

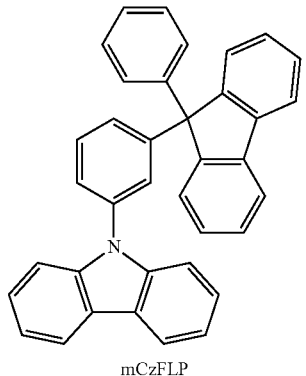

mCzFLP

In a 100 mL three-neck flask, 4.9 g (12.4 mmol) of 9-(3-bromophenyl)-9-phenylfluorene, 2.1 g (12.4 mmol) of carbazole, and 3.6 g (37.2 mmol) of sodium tert-butoxide were put, and the air in the flask was replaced with nitrogen. To this mixture, 31.0 mL of xylene, 0.2 mL of a 10% hexane solution

TABLE 4

| | Voltge (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 2 | 3.4 | 0.067 | 1.7 | (0.24, 0.50) | 960 | 57 | 53 | 21 |
| Comparative Light-emitting Element 2 | 3.7 | 0.068 | 1.7 | (0.34, 0.61) | 1100 | 65 | 55 | 19 |

From the above results, it is found that the light-emitting element 2 fabricated in this example has higher external quantum efficiency (higher emission efficiency) than the comparative light-emitting element 2. Note that from the chromaticity, it is found that the light-emitting element 2 emits blue green light whereas the comparative light-emitting element 2 emits green light.

Figure 23:
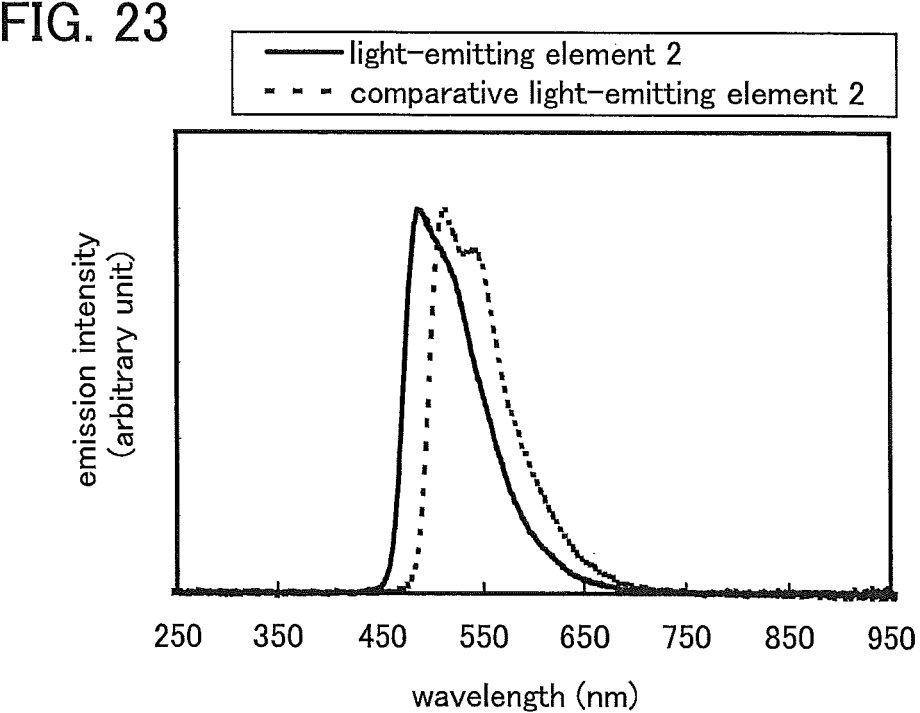
FIG. 23 shows emission spectra of the light-emitting element 2 and the comparative light-emitting element 2.

FIG. 23 shows emission spectra of the light-emitting element 2 and the comparative light-emitting element 2 when a current at a current density of 0.1 mA/cm$^2$ was supplied thereto. As shown in FIG. 23, the emission spectrum of the light-emitting element 2 has a peak around 490 nm and it is indicated that the peak is derived from emission of the phosphorescent organometallic iridium complex [Ir(tBumpypm)$_3$] (abbreviation). On the other hand, the emission spectrum of the comparative light-emitting element 2 has a peak around 514 nm and it is suggested that the peak is derived from emission of the phosphorescent organometallic iridium complex [Ir(ppy)$_3$] (abbreviation).

Reference Synthetic Example

A method for synthesizing 9-[3-(9-phenyl-9H-fluoren-9-yl)phenyl]-9H-carbazole (abbreviation: mCzFLP) used in part of the light-emitting elements fabricated in Examples 4 and 5 will be described.

of tri(tert-butyl)phosphine, and 48.1 mg (0.1 mmol) of bis(dibenzylideneacetone)palladium(0) were added, and the obtained mixture was stirred at 140° C. for 3.5 hours. After the stirring, 47.7 mg (0.1 mmol) of bis(dibenzylideneacetone)palladium(0) and 0.6 mL of a 10% hexane solution of tri(tert-butyl)phosphine were added, and the obtained mixture was stirred for 1.5 hours.

After the stirring, 70 mL of ethyl acetate and 150 mL of toluene were added, heating was performed, and suction filtration through Florisil, Celite, and alumina was performed to give a filtrate. The resulting filtrate was condensed to give a solid. The resulting solid was purified by silica gel column chromatography (a developing solvent: hexane and toluene in a 7:3 ratio) to give a target white solid. The resulting white solid was recrystallized from a mixed solvent of toluene and hexane to give 2.7 g of a target white solid in a yield of 46%.

Then, 1.5 g of the resulting white solid was purified by a train sublimation method. In the purification by sublimation, the white solid was heated at 186° C. under a pressure of 2.7 Pa with an argon flow rate of 5.0 mL/min. After the purification by sublimation, 1.4 g of a white solid which was a target substance was obtained at a collection rate of 93%. The reaction scheme of the synthetic method is shown in (D-1) below.

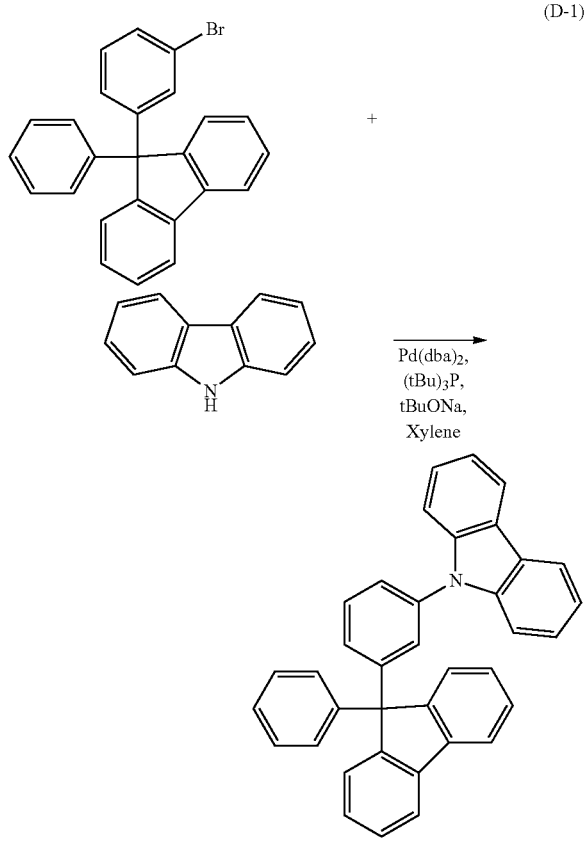

(D-1)

The compound obtained by the above synthetic scheme (D-1) was measured by a nuclear magnetic resonance method ($^1$H NMR). The measurement data are shown below.

$^1$H NMR (CDCl$_3$, 500 MHz): δ=7.19-7.49 (m, 21H), 7.77 (d, J=7.5 Hz, 2H), 8.10 (d, J=7.0 Hz, 2H).

Example 6

Synthetic Example 4

This example shows a method for synthesizing the phosphorescent organometallic iridium complex bis{2-methyl-3-[6-(2,5-dimethylphenyl)-4-pyrimidinyl-κN3]pyridyl-κC4} (2,4-pentaned ionato-κ$^2$O,O')iridium(III) (abbreviation: [Ir(dmpmpypm)$_2$(acac)]) represented by the structural formula (117) in Embodiment 1 according to one embodiment of the present invention. A structure of [Ir(dmpmpypm)$_2$(acac)] (abbreviation) is shown below.

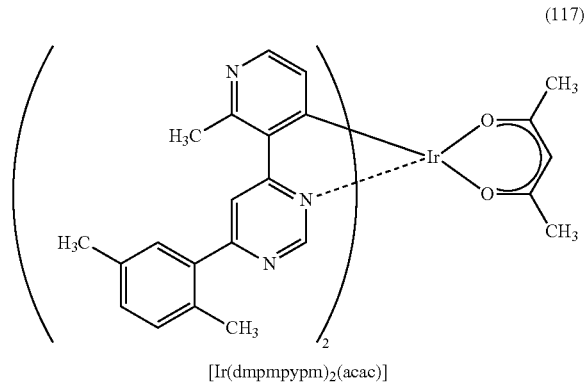

(117)

[Ir(dmpmpypm)$_2$(acac)]

Step 1: Synthesis of 4-Chloro-6-(2,5-dimethylphenyl)pyrimidine

First, 4.97 g of 4,6-dichloropyrimidine, 5.02 g of 2,5-dimethylphenylboronic acid, 3.55 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile were put in a recovery flask equipped with a reflux pipe, and the air in the flask was replaced with argon. This reaction container was heated by being irradiated with microwaves (2.45 GHz, 100 W) for 30 minutes. Further, 1.25 g of 2,5-dimethylphenylboronic acid, 0.89 g of sodium carbonate, and 0.073 g of Pd(PPh$_3$)$_2$Cl$_2$ were put in the flask, and the reaction container was heated again by being irradiated with microwaves (2.45 GHz, 100 W) for 30 minutes. Then, water was added to this solution and an organic layer was extracted with dichloromethane. The obtained organic layer was washed with water and saturated brine, and was dried with magnesium sulfate. After the drying, the solution was filtered. The solvent of this solution was distilled off, and then the obtained residue was purified by flash column chromatography using hexane and ethyl acetate in a ratio of 5:1 as a developing solvent, so that the target pyrimidine derivative was obtained (pale yellow oily substance, yield of 64%). A synthetic scheme of Step 1 is shown in (d-1) below.

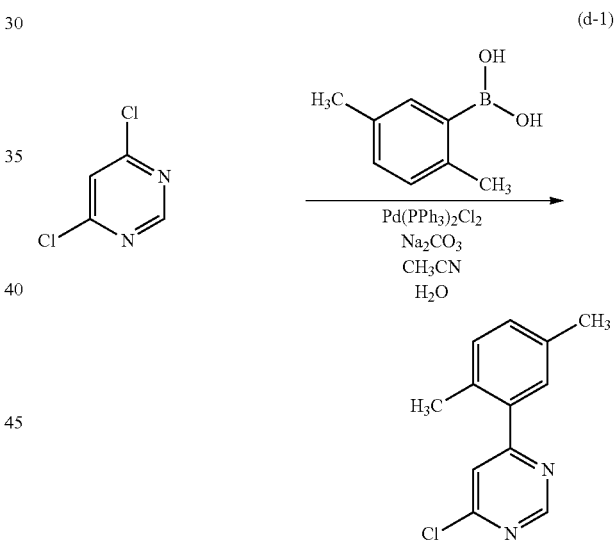

(d-1)

Step 2: Synthesis of 4-(2,5-Dimethylphenyl)-6-(2-methylpyridin-3-yl)pyrimidine (abbreviation: Hdmpmpypm)

Next, 1.98 g of 4-chloro-6-(2,5-dimethylphenyl)pyrimidine obtained in the above Step 1, 2.41 g of 2-methylpyridine-3-boronic acid pinacol ester, 14 mL of 1M aqueous solution of potassium acetate, 14 mL of 1M aqueous solution of sodium carbonate, and 30 mL of acetonitrile were put in a 100 mL round-bottom flask, and the air in the flask was replaced with argon. Then, 0.63 g of tetrakis(triphenylphosphine)palladium(0) was added to this mixture, and the reaction container was heated by being irradiated with microwaves (2.45 GHz, 100 W) for 60 minutes. This reaction mixture was extracted with ethyl acetate, and washing with saturated brine was performed. Anhydrous magnesium sulfate was added to the obtained solution of the extract for drying, and the resulting mixture was gravity-filtered to give a filtrate. The residue obtained by condensing the filtrate was purified by flash column chromatography using hexane and ethyl acetate in a ratio of 1:1 as a developing solvent. The fraction was condensed and the obtained oily substance was dissolved in dichloromethane. Then, filtration was performed through a filter aid in which Celite, alumina, and Celite were stacked in this order, so that the target pyrimidine derivative Hdmpmpypm (abbreviation) was obtained (orange oily substance, a yield of 87%). A synthetic scheme of Step 2 is shown in (d-2) below.

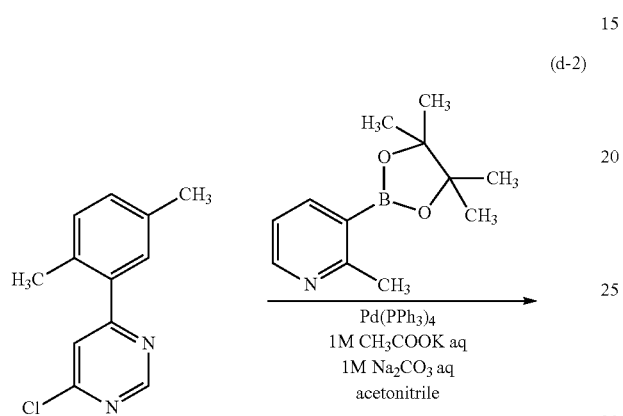

(d-2)

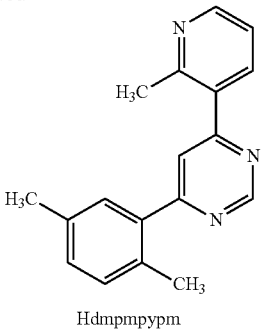

Hdmpmpypm

Step 3: Synthesis of Di-μ-chloro-tetrakis{2-methyl-3-[6-(2,5-dimethylphenyl)-4-pyrimidinyl-κN3]pyridyl-κC4}diiridium(III) (abbreviation: [Ir(dmpmpypm)$_2$Cl]$_2$)

Next, 15 mL of 2-ethoxyethanol, 5 mL of water, 2.23 g of the ligand Hdmpmpypm obtained in the above Step 2, and 1.13 g of iridium chloride hydrate (IrCl$_3$.H$_2$O) (produced by Sigma-Aldrich Corp.) were put in a recovery flask equipped with a reflux pipe, and the air in the flask was replaced with argon. Then, microwave irradiation (2.45 GHz, 100 W) was performed for 1 hour to cause a reaction. The solvent was distilled off, and then the obtained residue was suction-filtered and washed, so that the target dinuclear complex [Ir(dmpmpypm)$_2$Cl]$_2$ (abbreviation) was obtained (reddish brown solid, yield of 80%). A synthetic scheme of Step 3 is shown in (d-3) below.

(d-3)

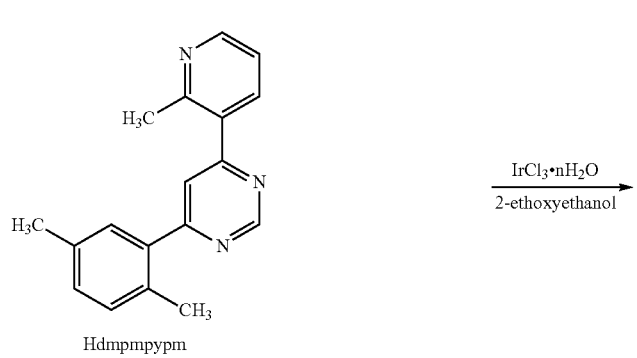

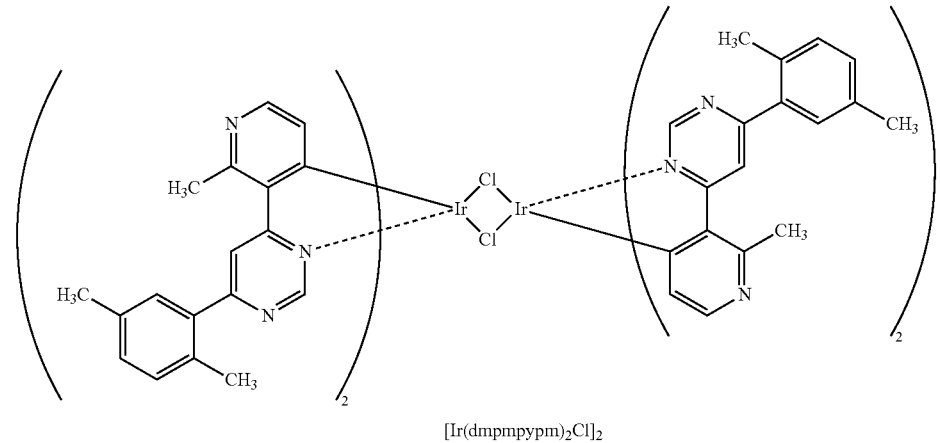

[Ir(dmpmpypm)$_2$Cl]$_2$

Step 4: Synthesis of Bis{2-methyl-3-[6-(2,5-dimethylphenyl)-4-pyrimidinyl-κN3]pyridyl-κC4}(2,4-pentane dionato-κ²O,O')iridium(III) (abbreviation: [Ir(dmpmpypm)₂(acac)])

Next, 2.24 g of the dinuclear complex [Ir(dmpmpypm)₂Cl]₂ obtained in the above Step 3, 1.50 g of sodium carbonate, 0.42 g of acetylacetone, and 40 mL of 2-ethoxyethanol were put in a 100 mL round-bottom flask, and the air in the flask was replaced with argon. Then, heating was performed by irradiation with microwaves (2.45 GHz, 100 W) for 1 hour. Further, 0.42 g of acetylacetone was put in the flask, and heating was again performed by irradiation with microwaves (2.45 GHz, 100 W) for 1 hour. The solvent was distilled off, the obtained residue was dissolved in dichloromethane, and washing was performed with water and saturated brine. The obtained organic layer was dried with magnesium sulfate. After the drying, the solution was filtered. The solvent of this solution was distilled off, and the obtained residue was purified by flash column chromatography using ethyl acetate and methanol in a ratio of 4:1 as a developing solvent. The fraction was condensed, and the obtained solid was purified by flash column chromatography using ethyl acetate as a developing solvent. Then, recrystallization was performed with a mixed solvent of ethyl acetate and hexane, so that the phosphorescent organometallic iridium complex [Ir(dmpmpypm)₂(acac)] (abbreviation) according to one embodiment of the present invention was obtained (yellow orange powder, yield of 8%). A synthetic scheme of Step 4 is shown in (d-4) below.

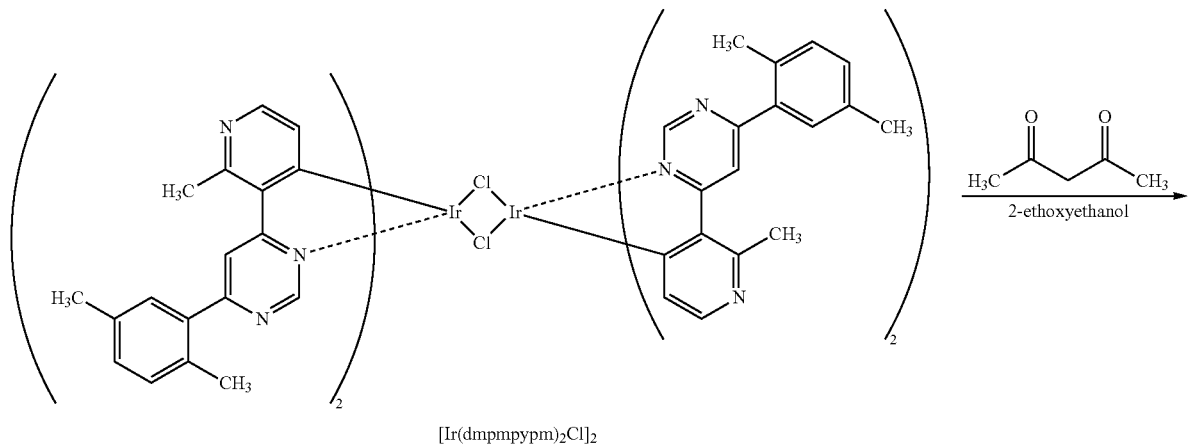

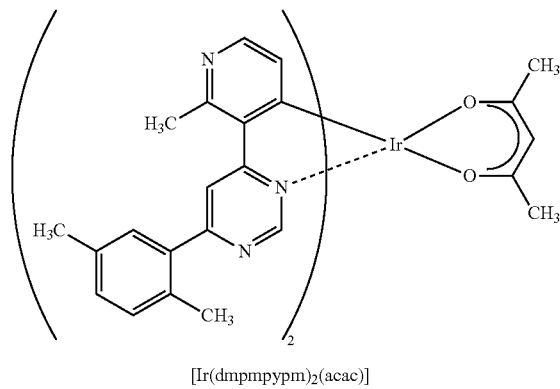

Figure 27:
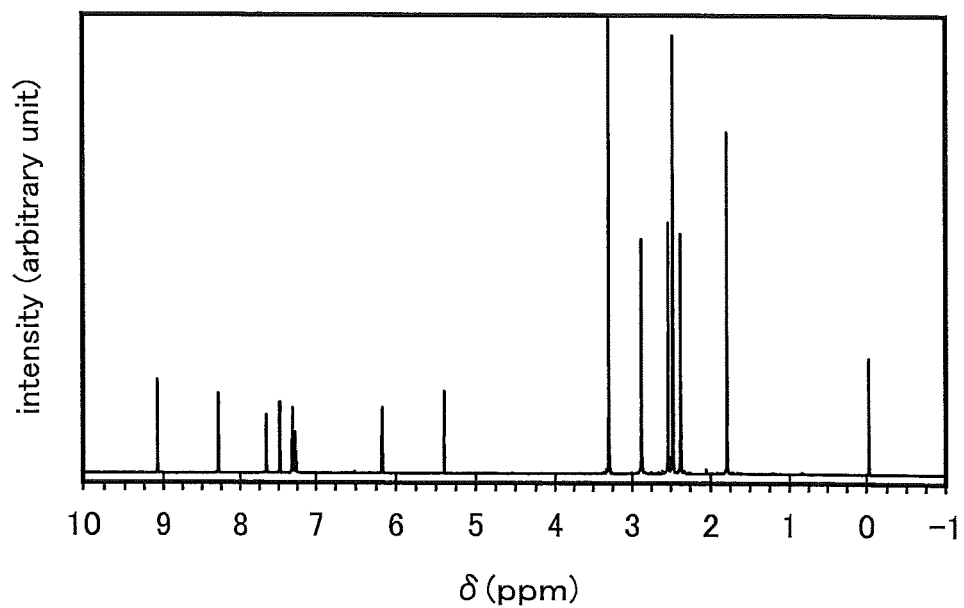
FIG. 27 shows a $^1$H-NMR chart of a phosphorescent organometallic iridium complex represented by a structural formula (117)

Results of analysis of the yellow orange powder obtained in the above Step 4 by nuclear magnetic resonance spectrometry ($^1$H-NMR) are shown below. The $^1$H-NMR chart is shown in FIG. 27. These results revealed that the phosphorescent organometallic iridium complex [Ir(dmpmpypm)$_2$(acac)] (abbreviation) represented by the structural formula (117) according to one embodiment of the present invention was obtained in Synthetic Example 4.

$^1$H-NMR. δ (DMSO-d6): 1.82 (s, 6H), 2.40 (s, 6H), 2.56 (s, 6H), 2.91 (s, 6H), 5.43 (s, 1H), 6.20 (d, 2H), 7.30 (d, 2H), 7.35 (d, 2H), 7.51 (d, 2H), 7.69 (s, 2H), 8.32 (s, 2H), 9, 11 (s, 2H).

Figure 28:
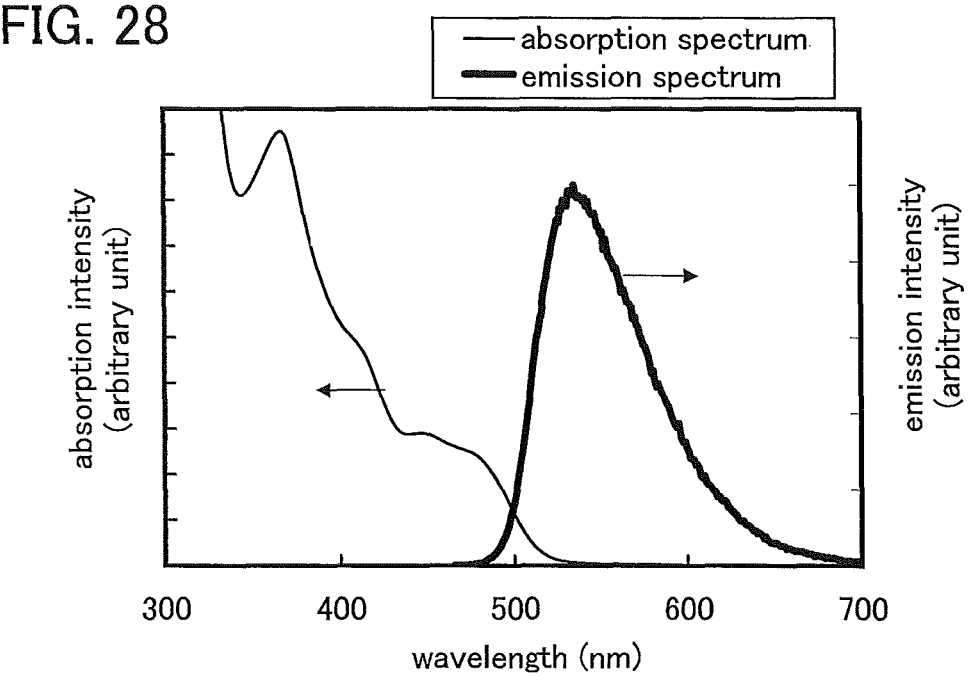
FIG. 28 shows an ultraviolet-visible absorption spectrum and an emission spectrum of the phosphorescent organometallic iridium complex represented by the structural formula (117).

Next, an ultraviolet-visible absorption spectrum (hereinafter, simply referred to as an "absorption spectrum") of a dichloromethane solution of [Ir(dmpmpypm)$_2$(acac)] (abbreviation) and an emission spectrum thereof were measured. The absorption spectrum was measured with an ultraviolet-visible spectrophotometer (V-550, produced by JASCO Corporation) using a dichloromethane solution (0.083 mmol/L) put in a quartz cell at room temperature. Further, the emission spectrum was measured with a fluorescence spectrophotometer (FS920, produced by Hamamatsu Photonics K.K.) using a degassed dichloromethane solution (0.083 mmol/L) put in a quartz cell at room temperature. FIG. 28 shows measurement results of the absorption spectrum and emission spectrum. In FIG. 28, the horizontal axis represents wavelength and the vertical axes represent absorption intensity and emission intensity. In FIG. 28, two solid lines are shown; a thin line represents the absorption spectrum, and a thick line represents the emission spectrum. The absorption spectrum in FIG. 28 is the results obtained in such a way that the absorption spectrum measured by putting only dichloromethane in a quartz cell was subtracted from the absorption spectrum measured by putting the dichloromethane solution (0.083 mmol/L) in a quartz cell.

As shown in FIG. 28, the phosphorescent organometallic iridium complex [Ir(dmpmpypm)$_2$(acac)] (abbreviation) according to one embodiment of the present invention has an emission peak at 535 nm, and yellow green light emission was observed from the dichloromethane solution.

This application is based on Japanese Patent Application serial no. 2012-096275 filed with Japan Patent Office on Apr. 20, 2012 and Japanese Patent Application serial no. 2013-049025 filed with Japan Patent Office on Mar. 12, 2013, the entire contents of which are hereby incorporated by reference.

What is claimed is:

1. A compound comprising a structure represented by a formula (G0')

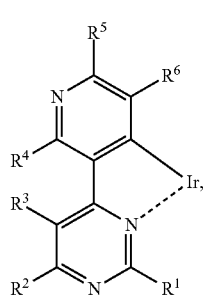

(G0')

wherein:
R$^1$ and R$^4$ to R$^6$ separately represent hydrogen or an alkyl group having 1 to 6 carbon atoms, and
R$^2$ and R$^3$ separately represent any of hydrogen, an alkyl group having 1 to 6 carbon atoms, a substituted or unsubstituted phenyl group, and a substituted or unsubstituted pyridyl group.

2. A compound represented by a formula (G1)

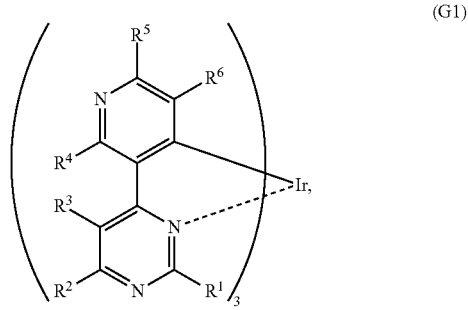

(G1)

wherein:
R$^1$ and R$^4$ to R$^6$ separately represent hydrogen or an alkyl group having 1 to 6 carbon atoms, and
R$^2$ and R$^3$ separately represent any of hydrogen, an alkyl group having 1 to 6 carbon atoms, a substituted or unsubstituted phenyl group, and a substituted or unsubstituted pyridyl group.

3. The compound according to claim 2, wherein the compound is represented by a formula (102)

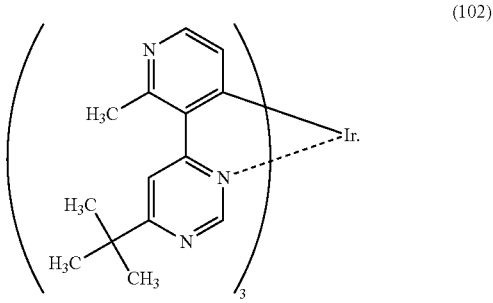

(102)

4. A compound represented by a formula (G2)

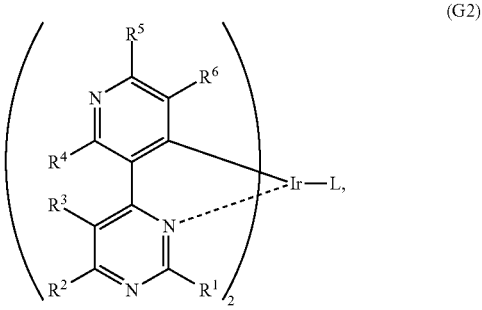

(G2)

wherein:
R$^1$ and R$^4$ to R$^6$ separately represent hydrogen or an alkyl group having 1 to 6 carbon atoms, R² and R³ separately represent any of hydrogen, an alkyl group having 1 to 6 carbon atoms, a substituted or unsubstituted phenyl group, and a substituted or unsubstituted pyridyl group, and L represents a monoanionic ligand.

5. The compound according to claim 4, wherein:

the monoanionic ligand is represented by one of formulas (L1) to (L6)

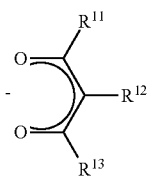
(L1)

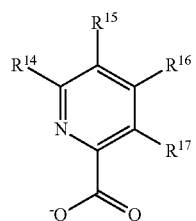
(L2)

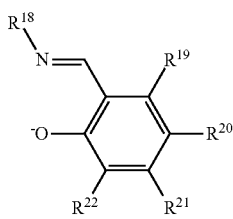
(L3)

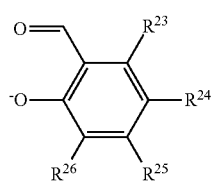
(L4)

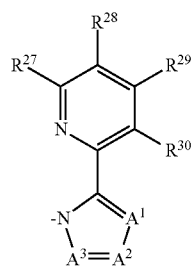
(L5)

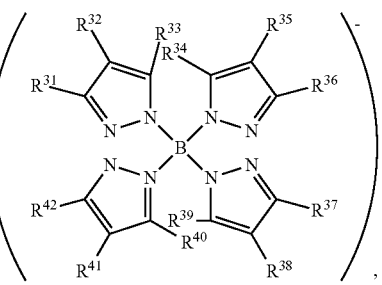
(L6)

$R^{11}$ to $R^{42}$ separately represent any of hydrogen, a substituted or unsubstituted alkyl group having 1 to 4 carbon atoms, halogen, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms, and $A^1$ to $A^3$ separately represent any of nitrogen, sp2 hybridized carbon bonded to hydrogen, and sp2 hybridized carbon bonded to any of an alkyl group having 1 to 4 carbon atoms, halogen, a haloalkyl group having 1 to 4 carbon atoms, and a phenyl group.

6. The compound according to claim 4, wherein the compound is represented by a formula (100)

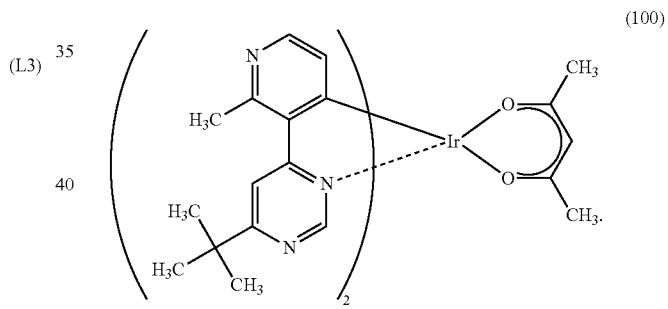
(100)

7. The compound according to claim 4, wherein the compound is represented by a formula (101)

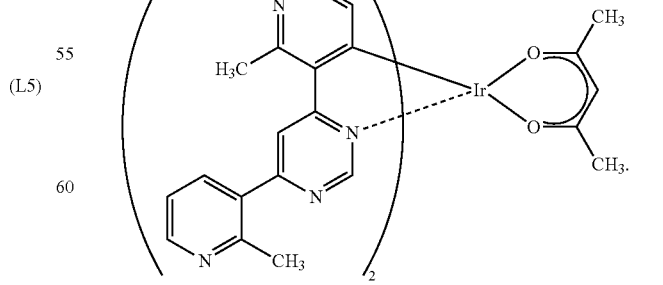
(101)

8. The compound according to claim 4, wherein the compound is represented by a formula (117)

(117)

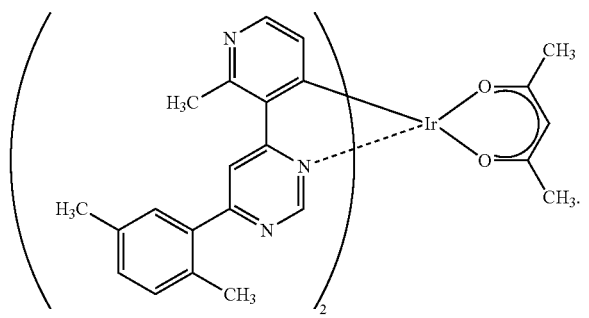

9. A light-emitting element comprising the compound according to claim 1.

10. A light-emitting device comprising the light-emitting element according to claim 9.

11. An electronic device comprising the light-emitting device according to claim 10.

12. A lighting device comprising the light-emitting device according to claim 10.

13. A light-emitting element comprising the compound according to claim 2.

14. A light-emitting device comprising the light-emitting element according to claim 13.

15. An electronic device comprising the light-emitting device according to claim 14.

16. A lighting device comprising the light-emitting device according to claim 14.

* * * * *